US007220402B1

(12) United States Patent
Andersen et al.

(10) Patent No.: US 7,220,402 B1
(45) Date of Patent: May 22, 2007

(54) ALPHA-FETOPROTEIN PEPTIDES AND USES FOR IMAGING

(75) Inventors: Thomas T. Andersen, Albany, NY (US); James A. Bennett, Delmar, NY (US); Herbert I. Jacobson, Albany, NY (US); Fassil B. Mesfin, Albany, NY (US)

(73) Assignee: Ordway Research Institute, Inc., Clifton Park, NY (US)

( * ) Notice: Subject to any disclaimer, the term of this patent is extended or adjusted under 35 U.S.C. 154(b) by 338 days.

(21) Appl. No.: 10/300,531

(22) Filed: Nov. 20, 2002

Related U.S. Application Data

(60) Provisional application No. 60/409,109, filed on Sep. 9, 2002, provisional application No. 60/397,012, filed on Jul. 19, 2002, provisional application No. 60/340,926, filed on Dec. 7, 2001, provisional application No. 60/331,841, filed on Nov. 20, 2001, provisional application No. 60/397,373, filed on Jul. 19, 2002.

(51) Int. Cl.
*A61K 5/055* (2006.01)
(52) U.S. Cl. ............ 424/9.341; 424/9.1; 424/9.3; 424/9.34; 424/9.4
(58) Field of Classification Search ............ 424/9.1, 424/9.3, 9.34, 9.341, 9.4
See application file for complete search history.

(56) References Cited

U.S. PATENT DOCUMENTS

| 5,674,842 A | 10/1997 | Mizejewski | 514/12 |
| 5,707,963 A | 1/1998 | Mizejewski | 514/12 |
| 6,306,832 B1 | 10/2001 | Pietras | 514/44 |

FOREIGN PATENT DOCUMENTS

| WO | 96/13581 | * | 5/1996 |
| WO | 03/007978 A1 | * | 1/2003 |

OTHER PUBLICATIONS

Gura Science vol. 273 p. 1041 (1997).*
Burgess et al, Journal of Cell Biology vol. 111 Nov. 1990 2129-2138.*
Lazar et al Molecular and Cellular Biology Mar. 1988 vol. 8 No. 3 1247-1252.*
Skolnick et al. (Trends in Biotech., 18(1):34-39, 2000).*
Atanaskova et al Oncogene 21(25):40000 (2002).*
Duan et al J. Biol. Chem. 276(15):11590 (2001).*
Kini et al Curr. Topics Pep. Prot. Res. 1:297 (1994).*
Wang et al J. Parenteral Sci. Tech. 42(2S):S04 (1998).*
Supplemantary Partial European Search report for EP 02 7901271, mailed Jul. 31, 2006.*
Allen, et al., "Purification of Alpha-Fetoprotein from Human Cord Serum with Demonstration of its Antiestrogenic Activity", *Biochimica et Biophysica Acta*, 1202:135-142 (1993).
Bedo, et al., "Retinoic Acid Regulates Growth Hormone Gene Expression", *Nature*, 339:231-234 (1989).
Bennett, et al., Abstract Only, "Transformation of Alpha-Fetoprotein (AFP) to a Negative Regulator of Estrogen-Dependent Growth by Ligands of the Steroid/Thyroid Hormone Receptor Superfamily", *Proceedings of the American Association for Cancer Research*, 34:244 (1993).
Bennett, et al., Abstract Only, "An α-Fetoprotein-Derived Peptide Inhibits Estrogen Receptor Positive Breast Cancers, Sensitive and Resistant to Tamoxifen", *Proc. Amer. Assoc. Can. Res.*, 42: 238 (2001).
Bennett, et al., "A Peptide Derived from α-Fetoprotein Prevents the Growth of Estrogen-Dependent Human Breast Cancers Sensitive and Resistant to Tamoxifen", *PNAS*, 99:2211-2215 (2002).
Collins, et al., "Spontaneous Cessation of Friend Murine Leukemia Virus Production by Leukemia Cell Line Y57: Overgrowth by Nonproducer Cells", *J. National Cancer Institute*, 64:11531159 (1980).
Conti, et al., "Thyroid Hormone Effect on α-Fetoprotein and Albumin Coordinate Expression by a Human Hepatoma Cell Line", *Biochimica et Biophysica Acta*, 1008:315-321 (1989).
Dauphinee, et al., Abstract Only, "Peptide Suppression of Breast Cancer Growth: In Search of Mechanisms by Identification of Cellular Targets", *Breast. Can. Res. Treat.*, 64:109 (2000).
Dietrich, "New Aspects of Steroid Hormone Dependent Tumor Growth", *Arch. Geschwulstforsch.*, 60:149-160 (1990).
Eisele, et al., "Studies on a Growth-Inhibitory Pepetide Derived from Alpha-Fetoprotein and Some Analogs", *J. Pept. Res.*, 57:29-38 (2001).
Eisele, et al., "Studies on Analogs of a Peptide Derived from Alpha-Fetoprotein Having Antigrowth Properties", *J. Pept. Res.*, 57:539-546 (2001).
Evans, "The Steroid and Thyroid Receptor Superfamily", *Science*, 240:889-895 (1988).
Garreau, et al., Phytoestrogens: New Ligands for Rat and Human α-Fetoprotein, *Biochimica et Biophysica Acta*, 1094:339-345 (1991).
Gekonge, et al., Abstract Only, "Regulation of Estrogen Activity by an Antiestrotrophic α-Fetoprotein Peptide", *Proc. Amer. Assoc. Can. Res.*, 42: 239 (2001).
Jacobson, et al., "Inhibition of Estrogen-Dependent Breast Cancer Growth by a Reaction Product of α-Fetoprotein and Estradiol", *Cancer Research*, 50:415-420 (1990).

(Continued)

*Primary Examiner*—Sheela J. Huff
(74) *Attorney, Agent, or Firm*—Ivor R. Elrifi, Esq.; Naomi S. Biswas, Esq.; Mintz, Levin

(57) ABSTRACT

The invention provides diagnostic procedures wherein the presence or absence of a cell-proliferating disorder, e.g., a breast cancer, may be determined. The imaging agents of the invention include alpha-fetoprotein hydrophilic analogs which have been determined to target cancers, e.g., breast cancer, and are also anti-cell proliferating in nature. These modulators contain amino acid structures which are arranged as a hydrophilic analog of an alpha-fetoprotein. The modulator may be a peptide; a peptidomimetic; or may be in the form of a pharmaceutically acceptable scaffold, such as a polycyclic hydrocarbon to which is attached the necessary amino acid structures. The imaging agents of the invention further comprise an imaging moiety that allows for the imaging of the area targeted by the imaging agent.

25 Claims, 19 Drawing Sheets

OTHER PUBLICATIONS

Jacobson, et al., "Anti Breast-Cancer Peptides Derived from Alpha-Fetoprotein", Abstract published in Cancer Detection and Prevention 2000; 24 (Supplement 1);, http://www.cancerprev.org/Journal/Issues/24/101/409/3220 (2000).

Jacobson, et al., "Estradiol-Induced Changes in Spectral and Biological Properties of Alpha-Fetoprotein", *Tumor Biology*, 11:104 (1990).

Jacobson, et al., "Pregnancy-Altered Breast Cancer Risk: Mediated by Maternal Serum AFP?", in *Biological Activities of Alpha$_1$-Fetoprotein*, Chapter 8, vol. II, pp. 93-100.

Keel, et al., "Purified Human α-Fetoprotein Inhibits Follicle-Stimulating Hormone-Stimulated Estradiol Production by Porcine Granulosa Cells in Culture", *Molecular and Cellular Endocrinology*, 94:21-25 (1993).

Keel, et al., "Purified Human Alpha-Fetoprotein Inhibits Growth Factor-stimulated Estradiol Production by Porcine Granulosa Cells in Monolayer Culture", *Endocrinology*, 130:3715-3717 (1992).

Larner, et al., "Binding of Estradiol-17-Fatty Acid Esters to Plasma Proteins", *Endocrinology*, 121:738-744 (1987).

Li, et al., "AFP-L3: A New Generation of Tumor Marker for Hepatocellular Carcinoma", *Clinica Chimica Acta*, 313:15-19 (2001).

MacColl, et al., "Interrelationships Among Biological Activity, Disulfide Bonds, Secondary Structure, and Metal Ion Binding for a Chemically Synthesized 34-Amino-Acid Peptide Derived from α-Fetoprotein", *Biochimica et Biophysica Acta*, 1528: 127-134 (2001).

Mesfin, et al., "Alpha-Fetoprotein-Derived Antiestrotrophic Octapeptide", *Biochimica et Biophysica Acta*, 1501: 33-43 (2000).

Mesfin, et al., Abstract Only, "Anti-Estrotrophic and Anti-Breast Cancer Activity of an AFP-Derived Octapeptide", *Proc. Amer. Assoc. Can Res.*, 41: 375 (2000).

Mesfin, et al., Abstract Only, "Novel Analogs in an Anti-Breast Cancer Octapeptide", *Proc. Amer. Assoc. Can. Res.*, 42: 778-779 (2001).

Mesfin, et al., "Development of a Synthetic Cyclized Peptide Derived from α-Fetoprotein that Prevents the Growth of Human Breast Cancer", *J. Pept. Res.*, 58: 246-256 (2001).

Mizejewski, et al., "Alpha-Fetoprotein Derived Synthetic Peptides: Assay of an Estrogen-Modifying Regulatory Segment", *Molec. Cell. Endo.*, 118:15-23 (1996).

Mizejewski, et al., "Separation of the Estrogen-Activated Growth-Regulatory Forms of Alpha-Fetoprotein in Mouse Amniotic Fluid", *Biology of Reproduction*, 42:887-898 (1990).

Mizejewski, et al., "Alpha-Fetoprotein Can Regulate Growth in the Uterus of the Immature and Adult Ovariectomized Mouse", *J. Reprod. Fert.*, 85:177-185 (1989).

Mizejewski, et al., "Studies of the Intrinsic Antiuterotropic Activity of Murine Alpha-Fetoprotein", *Tumor Biology*, 7:19-36 (1986).

Mizejewski, et al., "Estradiol-Activated α-Fetoprotein Suppresses the Uterotropic Response to Estrogens", *Proc. Natl. Acad. Sci. USA*, 80:2733-2737 (1983).

Mizejewski, "An Apparent Dimerization Motif in the Third Domain of Alpha-Fetoprotein: Molecular Mimicry of the Steroid/Thyroid Nuclear Receptor Superfamily", *BioEssays*, 15:427-432 (1993).

Mizejewski, "New Insights into AFP Structure and Function: Potential Biomedical Applications", in *Alpha-Fetoprotein and Congenital Disorders*, G.J. Mizejewski, and I.H. Porter, Eds., Academic Press, Inc., Orlando, Florida, pp. 5-34 (1985).

Mizejewski, et al., "Alpha-Fetoprotein in a Dual Regulator of Growth in Estrogen-Responsive Tissues", in *Biological Activities of Alpha$_1$-Fetoprotein*, G.J. Mizejewski and H.I. Jacobson, Eds., CRC Press, Inc., Boca Raton, Florida, vol. I, pp. 71-82 (1987).

Mizejewski, et al., "AFP Modification of Biologic Response in Estrogen-Sensitive Tissues: Use of *In Vitro* Models", in *Biological Activities of Alpha$_1$-Fetoprotein*, G.J. Mizejewski, B.R. Stanton, and H.I. Jacobson, Eds., CRC Press, Inc., Boca Raton, Florida, vol. II, pp. 59-74 (1989).

Nunez, et al., "The Physicochemical and Biological Properties of Alpha-Fetoprotein Depend on its Ligand Environment", *J. Nucl. Med. Sci.*, 33:18-26 (1989).

Rosebrock, et al., "Immunprecipitation Assay of Alpha-Fetoprotein Synthesis by Cultured House Hepatoma Cells Treated with Estrogens and Glucocorticords", *Differentiation*, 19:168-178 (1981).

Savu, et al., "Mouse α$_1$-Fetoprotein and Albumin", *J. Biol. Chem.*, 256:9114-9418 (1981).

Sonnenschein, et al., "Growth Inhibition of Estrogen-Sensitive Tumor Cells in Newborn Rats. Probable Role of Alpha-Fetoprotein", *J. National Cancer Institute*, 63:835-841 (1979).

Sonnenschein, et al., "Age-Dependent Growth Inhibition of Estrogen-Sensitive Rat Mammary Tumors. Probable Role of Alpha-Fetoprotein", *J. National Cancer Institute*, 64:1141-1146 (1980).

Soto, at al., "Control of Growth of Estrogen-Sensitive Cells: Role for α-Fetoprotein", *Proc. Natl. Acad. Sci. USA*, 77:2084-2087 (1980).

Vakharia, et al., "Human Alpha—Fetoprotein Peptides Bind Estrogen Receptor and Estradiol, and Suppress Breast Cancer", *Breast. Can. Res. Treat*, 63:41-52 (2000).

Wahli, et al., "Superfamily of Steroid Nuclear Receptors: Positive and Negative Regulators of Gene Expression", *FASEB*, 5:2243-2249 (1991).

Wan, et al., "The Effects of Retinoic acid on the Expression of α-Fetoprotein and Albumin Genes in Rat Hepatoma Cell Lines", *Differentiation*, 50:107-111 1992).

International Search Report for PCT/US02/37291, mailed on Aug. 29, 2003.

* cited by examiner

% INHIBITION OF E$_2$-STIMULATED GROWTH OF IMMATURE MOUSE UTERUS

μg OF PEPTIDE EMTOVNOG
SEQ ID NO: 4

Fig. 4A

μg OF CYCLO-(EMTOVNOGQ)
SEQ ID NO: 5

Fig. 6A

ALPHA-FETOPROTEIN PEPTIDES AND USES FOR IMAGING

RELATED APPLICATIONS

This application claims the benefit of priority under 35 U.S.C. 119(e) to copending U.S. Provisional Application Nos. 60/331,841, filed Nov. 20, 2001; 60/340,926, filed Dec. 7, 2001; 60/397,373, filed Jul. 19, 2002; 60/397,012, filed Jul. 19, 2002; 60/409,109, filed Sep. 9, 2002; the entire contents of which are incorporated herein by reference.

STATEMENT AS TO FEDERALLY SPONSORED RESEARCH

This invention was made with U.S. Government support under National Institutes of Health Grant No. CA 87434 and U.S. Army Grant Nos. DAMD 17-99-1-9054 and DAMD 17-99-1-9370. The government has certain rights in the invention.

FIELD OF THE INVENTION

The subject invention is directed generally to alpha-fetoprotein, and more particularly to peptides derived from alpha-fetoprotein and their use in treating, preventing and diagnosing cancer, including breast cancer.

BACKGROUND OF THE INVENTION

Every year in the U.S., 180,000 new cases of breast cancer are diagnosed and approximately 60% of these are estrogen-receptor-positive (ER+) (Martin et al. 1994). Moreover, every year there are a substantial number of breast cancer recurrences, and many of these are ER+. Several population and epidemiologic studies as well as laboratory studies have indicated that alpha-fetoprotein (AFP) interferes with estrogen-dependent responses, including the growth-promoting effects of estrogen on breast cancer (Bennett et al. 1998). For example, Couinaud et al. (1973) have reported that women with AFP-secreting hepatomas develop amenorrhea which self-corrects following removal of the hepatoma, and Mizejewski et al. (1983) have shown that AFP inhibits the responsiveness of the uterus to estrogen. Jacobson et al. (1989) and Richardson et al. (1998) have shown that elevated levels of AFP during pregnancy are associated with subsequent reduction in lifetime risk for breast cancer, and Jacobson et al. have hypothesized that this could be caused by a diminution in estrogen-dependent breast cancers (Jacobson et al. 1989). Sonnenschein et al. (1980) have shown in rats that an AFP-secreting hepatoma prevents the growth of an estrogen-dependent breast cancer in the same rat. Finally, it has been shown that AFP purified from a human hepatoma culture and then injected into tumor-bearing immune-deficient mice stopped the growth of ER+, but not estrogen-receptor-negative (ER-) human breast cancer xenografts in these mice, and did so by a mechanism different from that of tamoxifen (Bennett et al. 1998).

The active site of AFP responsible for its antiestrotrophic activity has been identified. It consists of amino acids 472–479 (SEQ ID NO: 6, EMTPVNPG), an 8-mer sequence in the 580-amino acid AFP molecule.

Aggregation of proteins and peptides has been seen with full length AFP as well as with subunits of AFP. Wu et al. (1985) showed that AFP tends to form aggregates, which may contribute to its loss of anti-estrotrophic activity during storage. Eisele et al. (2001) reported that oligomers of various sizes formed during storage of a 34-mer peptide (amino acids 447–480) derived from AFP. Similar aggregation behavior has been seen with a number of other protein and peptide pharmaceuticals, including human interferon-γ (Kendrick et al. 1998), human calcitonin (Bauer et al. 1994), insulin (Sluzky et al. 1991), and synthetic β-amyloid peptide (Hilbich et al. 1991; Christmanson et al. 1993; Halverson et al. 1990). Hughes et al. (1996) and Hilbich et al. (1992) reported inhibition of amyloid peptide aggregation by substitution of hydrophobic phenylalanine with hydrophilic threonine or by adding polylysine at the carboxy-terminus of the amyloid peptide.

SUMMARY OF THE INVENTION

The invention provides novel compositions, imaging agents, pharmaceutical compositions, and treatment methods for diseases involving cell proliferation, such as cancer, particularly breast cancer.

The invention provides diagnostic procedures wherein the presence or absence of a cell-proliferating disorder, e.g., a breast cancer, may be determined. The imaging agents of the invention include alpha-fetoprotein hydrophilic analogs which have been determined to target cancers, e.g., breast cancer, and are also anti-cell proliferating in nature. The imaging agents of the invention further comprise an imaging moiety that allows for the imaging of the area targeted by the imaging agent. The imaging moiety can be integral to the targeting moiety, e.g., by radiolabeling one of the atoms, or by means of an imaging moiety attached to the targeting moiety, such as a chelating agent, e.g., a bifunctional agent, which binds a medically useful metal ion to the peptide via the chelating agent.

In an embodiment, cancer imaging and/or diagnostic methods of the invention include administering an effective amount of a labeled alpha-fetoprotein peptide eight to twenty amino acids in length, where the labeled peptide comprises an alpha-fetoprotein peptide hydrophilic analog having the sequence EMTPVNPG (SEQ ID NO:6) substitution variant, peptidomimetic, retro-inverso isomer, or salt thereof and a medically useful metal ion to a patient, allowing for localization of the labeled peptide, and imaging the labeled peptide. The medically useful metal ion may be, e.g., iron, cobalt, nickel, copper, zinc, arsenic, selenium, molybdenum, technetium, e.g., technetium-99m; ruthenium, palladium, silver, cadmium, indium, antimony, rhenium, e.g., rhenium-186 or rhenium-188; osmium, iridium, platinum, gold, mercury, thallium, lead, bismuth, polonium or astatine. The medically useful metal ion may be radioactive, paramagnetic or superparamagnetic.

The imaging agents of the invention include targeting moieties which are cell proliferation modulator peptides, preferably those which are cell proliferation inhibitors. These modulators contain amino acid structures which are arranged as a hydrophilic analog of an alpha-fetoprotein. The modulator is generally a peptide itself, e.g., an octapeptide like SEQ ID NO: 1 or 5; a peptidomimetic; or the modulator may be in pharmaceutically acceptable scaffold form, such as a polycyclic hydrocarbon to which is attached the necessary amino acid structures for biological and/or chemical activity.

In one embodiment, the targeting moieties peptides include cell-proliferation modulators having the structure $Xaa_1\text{-}Xaa_2\text{-}Xaa_3\text{-}O\text{-}Xaa_4\text{-}N\text{-}Xaa_5\text{-}G\text{-}Xaa_6$ (SEQ ID NO:12), wherein $Xaa_1$ may be E, Q, N, or an acetylated or acylated derivative thereof; $Xaa_2$ may be M, K, or analogs thereof, such as methionine sulfone, D-lysine, or acelyated L-lysine;

a biologically active peptide with resistance to proteolysis can be obtained by substituting $Xaa_2$ with acetylated L-lysine, D-lysine, D-ornithine, or L-ornithine; $Xaa_3$ is an amino acid structure providing steric hindrance and hydrophilicity and can be selected from the group consisting of T and S; $Xaa_4$ may be V, I, L, T, a beta-branched amino acid structure, or a hydrophobic amino acid structure; $Xaa_5$ may be P, O or S; and $Xaa_6$ is an amino acid structure which may be present or absent; when present, it may be used for cyclization and desirably may be selected from the group consisting of Q and N, or a salt, retro-inverso isomer, or peptidomimetic thereof. In certain embodiments, $Xaa_1$ is E; $Xaa_3$ is T; $Xaa_4$ is V; or $Xaa_5$ is O. In one preferred embodiment, the peptides comprise the sequence EMTOVNOGQ (SEQ ID NO: 5) or EKTOVNOGN (SEQ ID NO: 1). The peptides may be linear or cyclic.

The targeting moiety analog may include one of the following: EKTOVNOGN (SEQ ID NO: 1); QMTPVNPG (SEQ ID NO:2); QMTPVNPGE (SEQ ID NO:3); EMTOVNOG (SEQ ID NO:4); EMTOVNOGQ (SEQ ID NO:5); EMTPVNPG (SEQ ID NO:6); EMTPVNPGQ (SEQ ID NO:7); EMTOVNPGQ (SEQ ID NO:8); and EMTPVNOGQ (SEQ ID NO:9) or substitution variant, peptidomimetic, retro-inverso isomer, or salt thereof. Linear or cyclic versions of the peptide may be used.

The targeting moieties, in an embodiment, are cell proliferation modulators containing a pharmaceutically acceptable scaffold (such as a polycyclic hydrocarbon) to which is attached amino acid structures arranged as a hydrophilic analog of an alpha-fetoprotein. One such compound includes a scaffold to which is attached a structure of at least eight amino acid structures, a hydroxyproline amino acid structure, an asparagine amino acid structure, and a glycine amino acid structure, wherein the amino acid structures are arranged as a hydrophilic analog of an alpha-fetoprotein, and therapeutic compound modulates cell proliferation. The arrangement of the amino acid structure in the scaffold is desirably EMTOVNOGQ (SEQ ID NO: 5) or EKTOVNOGN (SEQ ID NO: 1) in the cyclic or linear forms. In another embodiment, the arrangement of amino acid structures on the scaffold is as follows: a glutamic acid (E) or glutamine (Q) amino acid structure in the first position; a methionine (M) or lysine (K) amino acid structure, or analog thereof in the second position; a threonine (T) amino acid structure in the third position; a hydroxyproline (O) amino acid structure in the fourth position; a valine (V), isoleucine (I), or a beta-branched amino acid structure in the fifth position; an asparagine (N) amino acid structure in the sixth position; a hydroxyproline (O) amino acid structure in the seventh position; and a glycine (G) amino acid structure in the eighth position.

The targeting moieties are hydrophilic analogs of an alpha-fetoprotein, e.g., having the amino acid sequence EMTOVNOGQ (SEQ ID NO: 5) or EKTOVNOGN (SEQ ID NO: 1), or a substitution variant, peptidomimetic, retro-inverso isomer, or salt thereof. In one embodiment, the glutamic acid (E) may be replaced with glutamine (Q). In another embodiment, the amino group on the glutamic acid (E) is acetylated or acylated. In yet another embodiment, the methionine (M) may be replaced with lysine (K) or an analog thereof. The side chain of the hydroxyproline (O) adjacent to the T and V structures may be modified. The valine (V) may replaced by a beta-branched amino acid structure or hydrophobic amino acid structure, e.g., isoleucine (I); and/or the hydroxyproline (O) adjacent to the N and G structures may be replaced by serine (S).

The imaging agents of the invention may further include a metal ion-binding domain, where the linked medically useful metal ion is bound to the peptide (targeting moiety) via the metal ion-binding domain. In a particular embodiment, the imaging agent is a peptide is selected from the group consisting of $(R_1)—[Y_1]_n—(R_2)$, $(R_1)—[Y_1—(R_2)—Y_1]_n—(R_3)$, and $(R_1)—[Y_1—(R_2)—Y_2]_n—(R_3)$ wherein the metal ion-binding domain is $[Y_1]_n$, $[Y_1—(R_2)—Y_1]_n$, or $[Y_1—(R_2)—Y_2]_n$, where n is a number between 1 and 6, and $Y_1$, and $Y_2$ are amino acids comprising at least one element selected from sulfur, nitrogen and oxygen which is available or can be made available for binding to metal ions; at least one of $R_1$, $R_2$ and $R_3$ is the targeting moiety peptide substitution variant, peptidomimetic, retro-inverso isomer, or salt thereof; and those portions of $R_1$, $R_2$ and $R_3$ not comprising the targeting moiety peptide each comprise an amino acid sequence containing from 0 to about 20 amino acids. The metal ion-binding domain may include at least one amino acid selected from cysteine, cystine, histidine, penicillamine, deacylated methionine, lysine, arginine, aspartic acid, glutamic acid and tyrosine. Alternatively the metal ion-binding domain may include at least one member selected from $[Cys]_n$, $[Cys—(R_2)—Cys]_n$, $[Cys—(R_2)—Pen]_n$, $[His—(R_2)—Cys]_n$, $[His—(R_2)—Pen]_n$, $[His]_n$, and $([His—(R_2)—His]_n$, wherein n is a number between 1 and about 6; and $R_2$ is an amino acid sequence containing from 1 to about 20 amino acids.

The methods and compositions of the invention may be used with, e.g., gamma scintigraphy, specific photon emission computerized tomography, positron emission tomography or magnetic resonance imaging.

The imaging agents may be used in methods of diagnosing cell-proliferating disorders such as breast cancer in accordance with the invention, e.g., providing a medically useful metal ion-labeled alpha-fetoprotein peptide comprising a peptide sequence eight to twenty amino acids long which comprises a hydrophilic analog of an alpha-fetoprotein peptide having one of the sequences noted above, e.g., EKTOVNOGN (SEQ ID NO: 1); QMTPVNPG (SEQ ID NO:2); QMTPVNPGE (SEQ ID NO:3); EMTOVNOG (SEQ ID NO:4); EMTOVNOGQ (SEQ ID NO:5); EMTPVNPG (SEQ ID NO:6); EMTPVNPGQ (SEQ ID NO:7); EMTOVNPGQ (SEQ ID NO:8); or EMTPVNOGQ (SEQ ID NO:9) or substitution variant, peptidomimetic, retro-inverso isomer, or salt thereof and a medically useful metal ion, administering an effective amount of the labeled alpha-fetoprotein peptide to the patient, allowing for localization of the labeled peptide; and imaging the labeled alpha-fetoprotein peptide.

The administration may be by parenteral injection, e.g., intradermal, subcutaneous, intramuscular, intraperitoneal, or intravenous injection.

The invention also relates in an embodiment to methods of labeling alpha-fetoprotein peptides with a metal ion, by contacting an alpha-fetoprotein peptide solution (e.g., an alpha-fetoprotein peptide with a targeting moiety having the amino acid sequence EMTPVNPG (SEQ ID NO:6), or a hydrophilic analog of an alpha-fetoprotein peptide or substitution variant, peptidomimetic, retro-inverso isomer, or salt thereof having one of the sequences noted above, e.g., EKTOVNOGN (SEQ ID NO: 1); QMTPVNPG (SEQ ID NO:2); QMTPVNPGE (SEQ ID NO:3); EMTOVNOG (SEQ ID NO:4); EMTOVNOGQ (SEQ ID NO:5); EMTPVNPG (SEQ ID NO:6); EMTPVNPGQ (SEQ ID NO:7); EMTOVNPGQ (SEQ ID NO:8); or EMTPVNOGQ (SEQ ID NO:9), and a metal ion-binding domain), with a metal ion, and recovering the radiolabeled peptide (imaging agent). The solution may include excess stannous ions, i.e., greater than that required to completely reduce the metal ion. The metal ions may be, e.g., technetium in the pertechnetate form, or rhenium in the perrhenate form, e.g., rhenium-188 or rhenium-186. In a more particular embodiment for radiolabeling, alpha-fetoprotein peptides of the invention having a targeting moiety having a sequence (e.g., as noted above) and a metal ion-binding domain, may be labeled with a radioisotope of technetium or rhenium by contacting a solution of the peptide with stannous ions that are sufficient to reduce the radioisotope added in a subsequent step; reacting the peptide sequence and stannous ion solution with a radioisotope; and recovering the radiolabeled peptide. Before reacting the peptide sequence and stannous ion solution with a radioisotope, the solution may be lyophilized.

Imaging agents of the invention are also disclosed herein which are suitable for imaging via MRI. The agents include a paramagnetic metal ion bound to a complex which includes a chelator, and a targeting moiety comprising an alpha-fetoprotein peptide, e.g., having a peptide sequence eight to twenty amino acids long, which comprises a hydrophilic analog of an alpha-fetoprotein peptide, e.g., having one of the sequences described herein. The targeting moiety is covalently attached to said chelator which binds in at least a first coordination site of the metal ion and which is capable of interacting with a target substance such that the exchange of water in at least the first coordination site is increased. The chelator may be, e.g., DOTA or DPTA, or may comprise a polymer backbone. The paramagnetic metal ion(s) may be, e.g., Gd(III), Fe(III), Mn(II), Yt(III), Cr(III) or Dy(III). Gd(III) is particularly useful.

Additional imaging agents of the invention are also disclosed. The agents include a paramagnetic metal ion capable of binding n coordination atoms, wherein the metal ion is bound to a chelator such that the metal ion has coordination atoms at (n−1) or (n−2) coordination sites of the metal ion; and a targeting moiety, comprising an alpha-fetoprotein peptide, e.g., having a peptide sequence eight to twenty amino acids long, which comprises a hydrophilic analog of an alpha-fetoprotein peptide, e.g., having one of the sequences described herein. The targeting moiety is desirably covalently attached to the chelator that hinders the rapid exchange of water in the remaining coordination site or sites, and is capable of interacting with a target substance, such that the exchange of water at the remaining coordination site or sites is increased. These imaging agents may desirably include, as the metal ion, a Gd(III) ion, e.g., with coordination atoms at 8 coordination sites of the Gd(III) ion; and, as the targeting moiety, one which hinders the rapid exchange of water in a 9th coordination site, wherein the targeting moiety is capable of interacting with a target substance, such that the exchange of water at the 9th coordination site is increased.

The invention also includes methods for magnetic resonance imaging of a cell, tissue or patient, comprising administering an imaging agent of the invention to a cell, tissue or patient and rendering a magnetic resonance image of the cell, tissue or patient.

BRIEF DESCRIPTION OF THE DRAWING

FIG. 1a shows the peptide dose-response. FIG. 1a shows the anti-estrotrophic activity as a function of peptide storage time at −20° C. in the lyophilized state, 1 μg peptide per mouse;

FIG. 3a shows the dose-response. FIG. 3b shows the effect of time in storage;

FIGS. 4a and 4b illustrate the anti-uterotrophic activity of peptide with hydroxyproline substituted for proline. FIG. 4a shows the dose response. FIG. 4b shows the effect of time in storage;

Figure 6A:
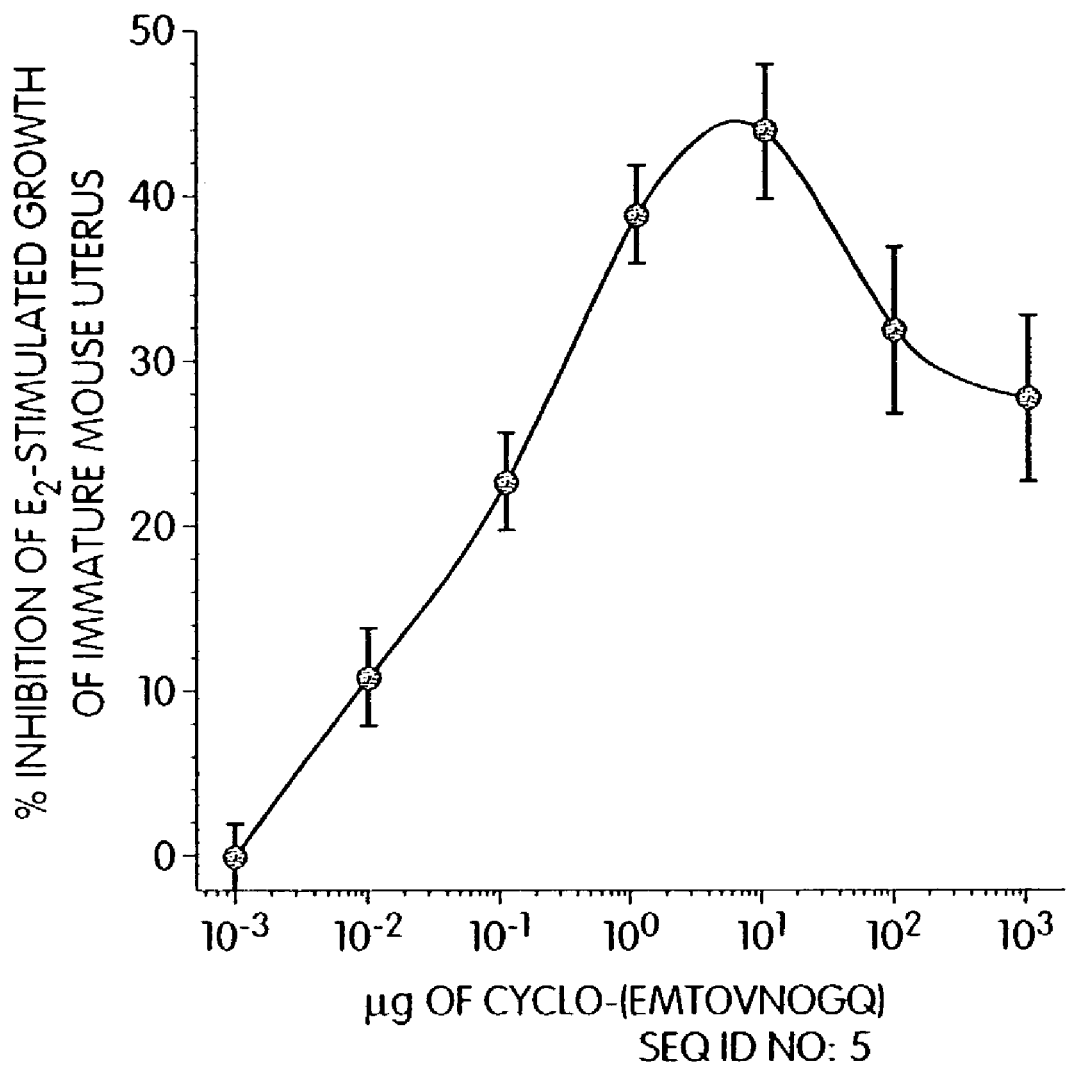

FIGS. 6a and 6b illustrate the anti-uterotrophic activity of cyclized peptide with hydroxyproline substituted for proline. FIG. 6a shows the dose response. FIG. 6b shows the effect of time in storage;

FIG. 9a shows MCF-7 tumors. At day 30 after tumor implantation, tumor volumes in the $E_2$+Pep group and in the $E_2$+Tam group were significantly different from tumor volumes in the $E_2$ alone group, $p<0.05$, Wilcoxon Ranks Sum Test. FIG. 9b shows a MCF-7 subline made resistant to tamoxifen in culture. At day 30 after tumor implantation, tumor volumes in the $E_2$+Pep group but not in the $E_2$+Tam group were significantly different from tumor volumes in the $E_2$ alone group, $p<0.05$, Wilcoxon Ranks Sum Test;

DETAILED DESCRIPTION OF THE INVENTION

Figure 1A:
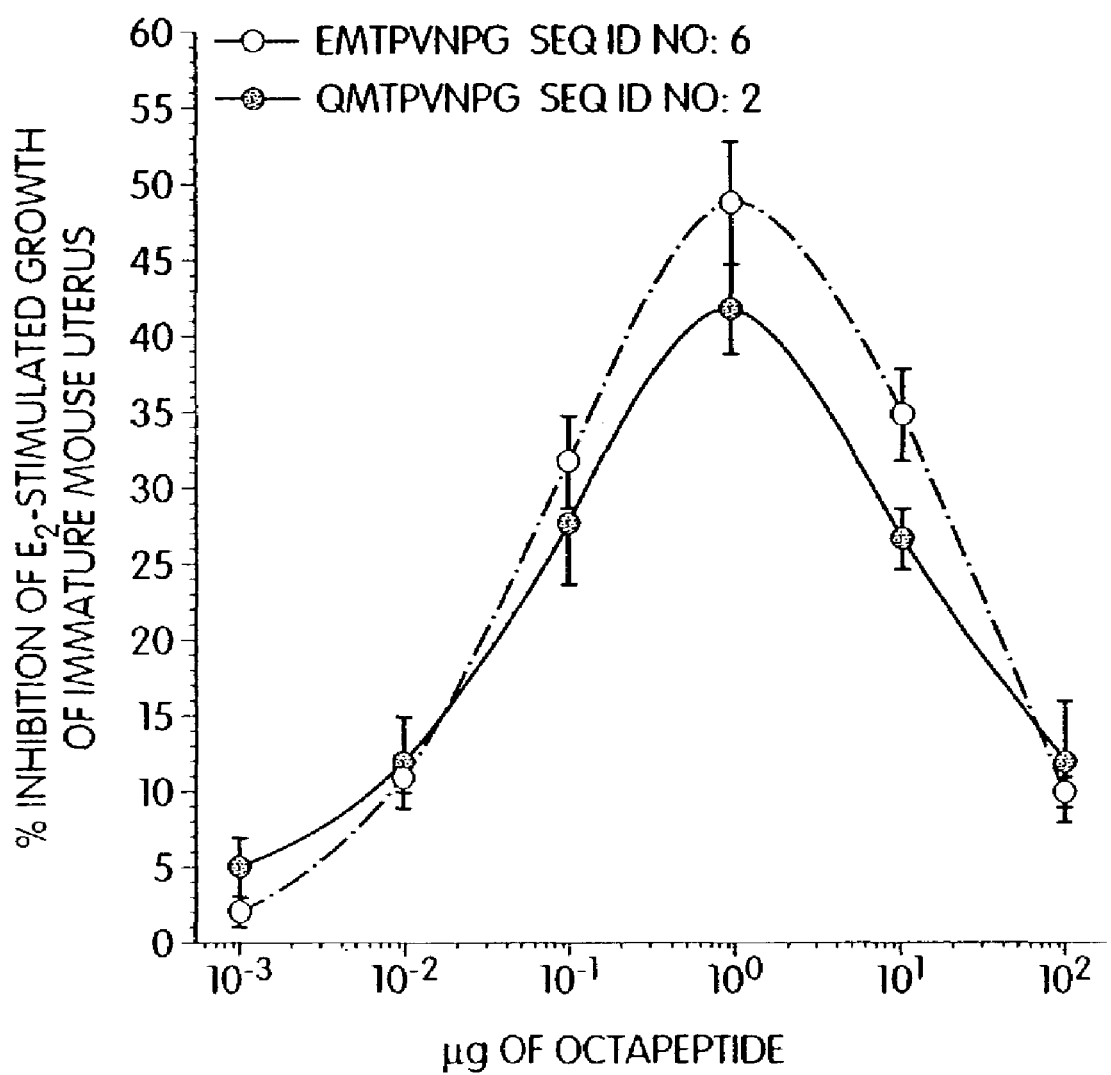
FIGS. 1a and 1b illustrate the anti-uterotrophic activity of octapeptide, SEQ ID NO: 2, QMTPVNPG, measured in the immature mouse uterine growth assay. Peptide or vehicle control was injected i.p. into immature female Swiss mice. One hour later 0.5 μg of $E_2$ vehicle control was injected i.p. into these mice. Twenty-two hours later, uteri were dissected and weighed. Percent inhibition of $E_2$-stimulated growth of uterus by peptide was calculated as described in Materials and Methods. There were five to eight replicate mice per treatment group.

An "amino acid structure" (such as a "glycine structure", a "hydroxyproline structure" or a "asparagine structure") includes the D-amino acid, as well as analogs, derivatives and mimetics of the amino acid that maintain the functional activity of the compound.

The targeting moiety structures include other peptide modifications, including analogs, derivatives and mimetics, that retain the ability of the modulator to alter cell proliferation as described herein. For example, a peptidic structure may be further modified to increase its stability, bioavailability, solubility, etc. "Analog", "derivative" and "mimetic" include molecules which mimic the chemical structure of a peptidic structure and retain the functional properties of the peptidic structure. Approaches to designing peptide analogs, derivatives and mimetics are known in the art. For example, see Farmer, P. S. in *Drug Design* (E. J. Ariens, ed.) Academic Press, New York, 1980, vol. 10, pp. 119–143; Ball, J. B. and Alewood, P. F. (1990) *J. Mol. Recognition.* 3:55. Morgan, B. A. and Gainor, J. A. (1989) *Ann. Rep. Med. Chem.* 24:243; and Freidinger, R. M. (1989) *Trends Pharmacol. Sci.* 10:270. See also Sawyer, T. K. (1995) *Peptidomimetic Design and Chemical Approaches to Peptide Metabolism* in Taylor, M. D. and Amidon, G. L. (eds.) *Peptide-Based Drug Design: Controlling Transport and Metabolism*, Chapter 17; Smith, A. B. 3rd, et al. (1995) *J. Am. Chem. Soc.* 117:11113–11123; Smith, A. B. 3rd, et al. (1994) *J. Am. Chem. Soc.* 116:9947–9962; and Hirschman, R., et al. (1993) *J. Am. Chem. Soc.* 115:12550–12568.

A "derivative" of a peptidic structure (e.g., a peptide or amino acid) includes forms of the peptidic structure in which one or more reaction groups on the peptidic structure have been derivatized with a substituent group. Examples of derivatives include peptides in which an amino acid side chain, the peptide backbone, or the amino- or carboxy-terminus has been derivatized (e.g., peptidic compounds with methylated amide linkages). An "analog" of a compound peptidic structure includes a compound which retains chemical structures of the peptidic structure necessary for functional activity of the peptidic structure yet which also contains certain chemical structures which differ from the peptidic structure. An example of an analog of a naturally-occurring peptide is a peptide which includes one or more non-naturally-occurring amino acids.

A "mimetic" of a peptidic structure includes compounds in which chemical structures of the peptidic structure necessary for functional activity of the peptidic structure have been replaced with other chemical structures which mimic the conformation of the peptidic structure. Examples of peptidomimetics include peptidic compounds in which the peptide backbone is substituted with one or more benzodiazepine molecules (see e.g., James, G. L. et al. (1993) *Science* 260:1937–1942).

The term "mimetic", and in particular, peptidomimetic, includes isosteres. The term "isostere" includes chemical structures that can be substituted for a second chemical structure because the steric conformation of the first structure fits a binding site specific for the second structure. The term specifically includes peptide backbone modifications (i.e., amide bond mimetics) well-known to those skilled in the art. Such modifications include modifications of the amide nitrogen, the α-carbon, amide carbonyl, complete replacement of the amide bond, extensions, deletions or backbone crosslinks. Several peptide backbone modifications are known, including $\psi[CH_2S]$, $\psi[CH_2NH]$, $\psi[CSNH_2]$, $\psi[NHCO]$, $\psi[COCH_2]$, and $\psi[(E)$ or $(Z)$ $CH=CH]$. In the nomenclature used above, $\psi$ indicates the absence of an amide bond. The structure that replaces the amide group is specified within the brackets.

Other possible modifications include an N-alkyl (or aryl) substitution (ψ[CONR]), or backbone crosslinking to construct lactams and other cyclic structures. Other derivatives of the modulator compounds of the invention include C-terminal hydroxymethyl derivatives, O-modified derivatives (e.g., C-terminal hydroxymethyl benzyl ether), N-terminally modified derivatives including substituted amides such as alkylamides and hydrazides and compounds in which a C-terminal phenylalanine structure is replaced with a phenethylamide analog (e.g., Val-Phe-phenethylamide as an analog of the tripeptide Val-Phe-Phe).

These "modulator peptide proteins", i.e., as used in the targeting moiety, contain amino acid structures which are arranged as a hydrophilic analog of an alpha-fetoprotein. The modulator portion may be a peptide itself, e.g., an octapeptide like that of SEQ ID NO: 5; or substitution variant, peptidomimetic, retro-inverso isomer, or salt thereof; or may be in the form of a pharmaceutically acceptable scaffold, such as a polycyclic hydrocarbon to which is attached the necessary amino acid structures for biological and/or chemical activity.

A "modulator" of cell proliferation includes agents that, when contacted with tissue or cells, alter cell proliferation. In the presence of a modulator, cell proliferation is "altered" or "modulated". The various forms of the term "alteration" or "modulation" are intended to encompass both inhibition of cell proliferation and promotion of cell proliferation. Cell proliferation is "inhibited" in the presence of the modulator when there is a decrease in the cell proliferation as compared to the amount and/or rate of cell proliferation in the absence of the modulator. The various forms of the term "inhibition" are intended to include both complete and partial inhibition of cell proliferation.

The modulator portion is typically at least eight amino acids in length and is based on an octapeptide structure of $Xaa_1$-$Xaa_2$-$Xaa_3$-O-$Xaa_4$-N-$Xaa_5$-G-$Xaa_6$ (SEQ ID NO:12), or a salt, retro-inverso isomer, or peptidomimetic thereof. "Xaa" is intended to denote an amino acid structure. $Xaa_1$ may be Glu (E), Gln (Q), Asn (N), or an acetylated or acylated derivative thereof. $Xaa_2$ may be Met (M) or Lys (K), or analogs or derivatives thereof, e.g., methionine sulfone, D-lysine, or an acetylated or acylated L-lysine derivative. A biologically active peptide with resistance to proteolysis can be obtained by substituting $Xaa_2$ with acetylated L-lysine, D-lysine, D-ornithine, or L-ornithine. $Xaa_3$ is an amino acid structure providing steric hindrance and/or hydrophilicity (e.g., having a value of $-0.5$ or greater, as described in U.S. Pat. No. 4,554,101) and can be selected from the group consisting of Thr (T) and Ser (S). $Xaa_4$ may be Val (V), Ile (I), Leu (L), Thr (T), or an analog or derivative thereof, or a beta-branched, or hydrophobic amino acid structure (e.g., having a value of $-0.5$ or less, as described in U.S. Pat. No. 4,554,101.) $Xaa_5$ may be Pro (P), hydroxyproline (O) or Ser (S), or an analog or derivative thereof. $Xaa_6$ is an amino acid structure which may be present or absent; when present, it may be used for cyclization and desirably may be selected from the group consisting of Gln (Q) and Asn (N).

In certain embodiments, $Xaa_1$ is desirably E; $Xaa_3$ is T; $Xaa_4$ is V; $Xaa_5$ is O. In a particularly preferred embodiment, the peptides comprise the sequence EMTOVNOGQ (SEQ ID NO: 5) or EKTOVNOGN (SEQ ID NO: 1). As noted above, the peptides may be linear or cyclic.

As noted above, the modulator portion may be in the form of a scaffold to which is attached a structure of at least eight amino acid structures, a hydroxyproline amino acid structure, an asparagine amino acid structure, and a glycine amino acid structure, wherein the amino acid structures are arranged as a hydrophilic analog of an alpha-fetoprotein, and therapeutic compound modulates cell proliferation. Use of a scaffold material such as a polycyclic hydrocarbon allows flexibility for administration as it presents an active compound which is much less resistant to degradation when administered orally. The arrangement of the amino acid structure in the scaffold is desirably EMTOVNOGQ (SEQ ID NO: 5) or EKTOVNOGN (SEQ ID NO: 1) in the cyclic or linear forms.

In another embodiment, the arrangement of amino acid structures on the scaffold may be a glutamic acid (E) or glutamine (Q) amino acid structure in the first position; a methionine (M) or lysine (K) amino acid structure in the second position; a threonine (T) amino acid structure in the third position; a hydroxyproline (O) amino acid structure in the fourth position; a valine (V), isoleucine (I), or beta-branched amino acid structure in the fifth position; an asparagine (N) amino acid structure in the sixth position; a hydroxyproline (O) amino acid structure in the seventh position; and a glycine (G) amino acid structure in the eighth position.

The targeting moiety includes the peptide EMTOVNOGQ (SEQ ID NO: 5) or EKTOVNOGN (SEQ ID NO: 1) in the cyclic or linear forms, or a substitution variant, peptidomimetic, retro-inverso isomer, or salt thereof. In one embodiment, the glutamic acid (E) may be replaced with glutamine (Q). In another embodiment, the amino group on the glutamic acid (E) is acetylated or acylated. In yet another embodiment, the methionine (M) may be replaced with lysine (K) or an analog thereof. The side chain of the hydroxyproline (O) adjacent to the T and V structures may be modified. The valine (V) may replaced by a beta-branched amino acid structure or hydrophobic amino acid structure, e.g., isoleucine (I); and/or the hydroxyproline (O) adjacent to the N and G structures may be replaced by serine (S).

Analogs of the targeting moiety peptides are intended to include compounds in which one or more amino acids of the peptidic structure are substituted with a homologous amino acid such that the properties of the original modulator are maintained. Preferably conservative amino acid substitutions are made at one or more amino acid structures. A "conservative amino acid substitution" includes one in which the amino acid structure is replaced with an amino acid structure having a similar side chain. Families of amino acid structures having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), β-branched side chains (e.g., threonine, valine, isoleucine) and aromatic side chains (e.g., tyrosine, phenylalanine, tryptophan, histidine). Non-limiting examples of homologous substitutions that can be made in the peptidic structures of the modulators of the invention include substitution of D-phenylalanine with D-tyrosine, D-pyridylalanine or D-homophenylalanine, substitution of D-leucine with D-valine or other natural or non-natural amino acid having an aliphatic side chain and/or substitution of D-valine with D-leucine or other natural or non-natural amino acid having an aliphatic side chain.

Acceptable amino acid substitutions are those that do not affect the function of the targeting moiety peptide. Moreover, particular amino acid substitutions may further contribute to the ability of the peptide to alter cell proliferation and/or may confer additional beneficial properties on the peptide (e.g., increased solubility, etc.). A peptide having an identical amino acid sequence to that found within a parent peptide but in which all L-amino acids have been substituted with all D-amino acids is also referred to as an "inverso" compounds. For example, if a parent peptide is Thr-Ala-Tyr, the inverso form is D-Thr-D-Ala-D-Tyr.

In addition to the particular peptides disclosed herein, peptide mutants which have additional amino acid structures modified are also contemplated. Such mutants may be more active and/or more stable for in vitro and in vivo formulations. For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated that various changes may be made in the peptide sequences of the disclosed compositions, or corresponding DNA sequences which encode said peptides without appreciable loss of their biological utility or activity.

In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine 0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those which are within ±1 are particularly preferred, and those within ±0.5 are even more particularly preferred. It is also understood in the art that the substitution of like amino acids can be made effectively on the basis of hydrophilicity. U.S. Pat. No. 4,554,101, states that the greatest local average hydrophilicity of a protein, as governed by the hydrophilicity of its adjacent amino acids, correlates with a biological property of the protein.

As detailed, e.g., in U.S. Pat. No. 4,554,101, the following hydrophilicity values have been assigned to amino acid structures: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine ((−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those which are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine. D-amino acids may be used, e.g., to confer resistance to protease degradation.

Targeting moiety peptides of the invention can be prepared by standard techniques known in the art. The peptide component of a modulator can be synthesized using standard techniques such as those described in Bodansky, M. *Principles of Peptide Synthesis*, Springer Verlag, Berlin (1993) and Grant, G. A (ed.). *Synthetic Peptides: A User's Guide*, W. H. Freeman and Company, New York (1992). Automated peptide synthesizers are commercially available (e.g., Advanced ChemTech Model 396; Milligen/Biosearch 9600). Additionally, one or more modulating groups can be attached to the peptidic component by standard methods, for example using methods for reaction through an amino group (e.g., the alpha-amino group at the amino-terminus of a peptide), a carboxyl group (e.g., at the carboxy terminus of a peptide), a hydroxyl group (e.g., on a tyrosine, serine or threonine structure) or other suitable reactive group on an amino acid side chain (see e.g., Greene, T. W and Wuts, P. G. M. *Protective Groups in Organic Synthesis*, John Wiley and Sons, Inc., New York (1991).

The invention also includes peptides of eight to twenty amino acids in length which comprise a hydrophilic analog of an alpha-fetoprotein peptide, e.g., SEQ ID NO: 6, EMT-PVNPG. The peptide may be linear or cyclic, and may include (D) as well as (L) amino acids. In one embodiment, the peptide includes an amino acid sequence selected from the group consisting of:

SEQ ID NO: 1: EKTOVNOGN
SEQ ID NO: 2: QMTPVNPG
SEQ ID NO: 3: QMTPVNPGE
SEQ ID NO: 4: EMTOVNOG
SEQ ID NO: 5: EMTOVNOGQ
SEQ ID NO: 6: EMTPVNPG
SEQ ID NO: 7: EMTPVNPGQ
SEQ ID NO: 8: EMTOVNPGQ
SEQ ID NO: 9: EMTPVNOGQ
SEQ ID NO: 10: EMTPVNOG and
SEQ ID NO: 11: EMTOVNPG, or a substitution variant, peptidomimetic, retro-inverso isomer, or salt thereof.

Dimers of these peptides (such as a peptide having SEQ ID NO: 4 in combination with a peptide having SEQ ID NO: 5, or a peptide having SEQ ID NO: 3 in combination with a peptide having SEQ ID NO: 10), or other multimers (three or more peptides), are also included.

The structure of some of the compounds of the invention may include asymmetric carbon atoms. Accordingly, the isomers arising from such asymmetry (e.g., all enantiomers and diastereomers) are included within the scope of the invention, unless indicated otherwise. Such isomers can be obtained in substantially pure form by classical separation techniques and by stereochemically controlled synthesis.

Furthermore, the structures and other compounds and moieties discussed in this application also include all tautomers thereof. Alkenes can include either the E- or Z-geometry, where appropriate.

In one embodiment, the targeting moiety peptides include cell-proliferation modulators having the structure $Xaa_1$-$Xaa_2$-$Xaa_3$-O-$Xaa_4$-N-$Xaa_5$-G-$Xaa_6$ (SEQ ID NO:12), wherein $Xaa_1$ may be E, Q, and N, or an acetylated or acylated derivative thereof; $Xaa_2$ may be M, K, or analogs thereof, such as methionine sulfone, D-lysine, or acetylated L-lysine; $Xaa_3$ is an amino acid structure providing steric hindrance and hydrophilicity and can be selected from the group consisting of T and S; $Xaa_4$ may be V, I, L, T, a beta-branched amino acid structure, or a hydrophobic amino acid structure; $Xaa_5$ may be P, O or S; and $Xaa_6$ is an amino acid structure which may be present or absent; when present, it may be used for cyclization and desirably may be selected from the group consisting of Q and N, or a salt, retro-inverso isomer, or peptidomimetic thereof. In certain embodiments, $Xaa_1$ is E; $Xaa_3$ is T; $Xaa_4$ is V; or $Xaa_5$ is O. In one preferred embodiment, the peptides comprise the sequence EMTOVNOGQ (SEQ ID NO: 5) or EKTOVNOGN (SEQ ID NO: 1). The peptides may be linear or cyclic.

The targeting moiety peptides, in an embodiment, contain a pharmaceutically acceptable scaffold (such as a polycyclic hydrocarbon) to which is attached amino acid structures arranged as a hydrophilic analog of an alpha-fetoprotein. One such compound includes a scaffold to which is attached a structure of at least eight amino acid structures, a hydroxyproline amino acid structure, an asparagine amino acid structure, and a glycine amino acid structure, wherein the amino acid structures are arranged as a hydrophilic analog of an alpha-fetoprotein, and therapeutic compound modulates cell proliferation. The arrangement of the amino acid structure in the scaffold is desirably EMTOVNOGQ (SEQ ID NO: 5) or EKTOVNOGN (SEQ ID NO: 1).

In another embodiment, the arrangement of amino acid structures on the scaffold is as follows: a glutamic acid (E) or glutamine (Q) amino acid structure in the first position; a methionine (M) or lysine (K) amino acid structure, or analog thereof in the second position; a threonine (T) amino acid structure in the third position; a hydroxyproline (O) amino acid structure in the fourth position; a valine (V), isoleucine (I), or a beta-branched amino acid structure in the fifth position; an asparagine (N) amino acid structure in the sixth position; a hydroxyproline (O) amino acid structure in the seventh position; and a glycine (G) amino acid structure in the eighth position.

The targeting moiety peptides are hydrophilic analogs of an alpha-fetoprotein, e.g., having the amino acid sequence EMTOVNOGQ (SEQ ID NO: 5) or EKTOVNOGN (SEQ ID NO: 1) in the cyclic or linear forms, or a substitution variant, peptidomimetic, retro-inverso isomer, or salt thereof. In one embodiment, the glutamic acid (E) may be replaced with glutamine (Q). In another embodiment, the amino group on the glutamic acid (E) is acetylated or acylated. In yet another embodiment, the methionine (M) may be replaced with lysine (K) or an analog thereof. The side chain of the hydroxyproline (O) adjacent to the T and V structures may be modified. The valine (V) may replaced by a beta-branched amino acid structure or hydrophobic amino acid structure, e.g., isoleucine (I); and/or the hydroxyproline (O) adjacent to the N and G structures may be replaced by serine (S).

The terms "bind," "binding," "complex," and "complexing," referred to in the specification and claims, include all types of physical and chemical binding, reactions, complexing, attraction, chelating and the like.

The "metal ion-binding domain" includes a sequence of one or more amino acids containing sulfur, nitrogen or oxygen which is available for binding or can be made available for binding to metal ions. Sulfur-containing amino acids include cysteine (Cys), cystine (Cys-Cys) and penicillamine (Pen), although deacylated methionine (Met), and other amino acids, may also be used. Useful nitrogen-containing amino acids include histidine (His), but under certain conditions lysine (Lys) and arginine (Arg), which have $pK_a$ values of 10.0 and 12.0, and other amino acids, may also be employed. The terminal amino group of peptides may also be employed. Useful oxygen-containing amino acids include aspartic acid (Asp), glutamic acid (Glu), tyrosine (Tyr), serine (Set) and threonine (Thr); and the terminal carboxyl group of peptides and other moieties. The amino acid sequences advantageously include one or more Cys, one or more His, or a combination of Cys and His. Pen, which is an analogue of Cys, may be directly substituted for any given Cys. Cys may be present in the peptide as a disulfide in the form of cystine. The metal ion-binding domain may employ L-amino acids, or one or more of the amino acids may be substituted by D-amino acids (D-stereoisomer). The metal ion-binding domains may occur once or multiple times in any given peptide, and may occur in any combination.

The metal ion-binding domains may be stabilized by adding a positively-charged transition metal ion, such as Zn, Cu, Sn, Co, or Ni, and the like, which has been selected to have a low binding strength order. Through a replacement reaction, the transition metal ion replaces the H ion of the thiolate, imidazole or carboxyl group. Divalent zinc and tin ions are thought to be particularly attractive. Some transition metals can simultaneously be used to reduce disulfide bridges and stabilize the metal binding sequences, such as Sn (II), which is particularly useful with cystine formations. In any case, transition metals tend to be weakly associated.

The positively-charged transition metal ions are introduced to the peptide in an aqueous solution containing an appropriate buffer. The buffer may have dicarboxylic acids (tartrate, phthalate, citrate), amino acids (glycine, di-glycine, tri-glycine), borate, glucoheptonate, or the like. The buffer components may also be used as stabilizers for metal ions and/or as transfer agents or ligands for radionuclides, such as $^{99m}$Tc. For radiolabeling in acidic conditions, typically 10 mM tartrate and 40 mM phthalate at pH values of about 5 to about 7 are used. For radiolabeling in basic conditions, typically 10 mM glycine at pH values of about 8 to about 10 are used. The buffer may also contain a number of excipients and/or stabilizers including NaCl, inositol, glucoheptonate, and the like.

The medically useful metal ion may be radioactive and generate gamma rays, beta particles, or positrons which are converted into gamma rays upon collision with electrons. The medically useful metal ion may also be paramagnetic or supermagnetic, and may used in diagnostic imaging procedures including gamma scintigraphy, specific photon emission computerized tomography, positron emission tomography or magnetic resonance imaging.

Particularly advantageous metal ions include elements 26–30 (Fe, Co, Ni, Cu, Zn), 33–34 (As, Se), 42–50 (Mo, Tc, Ru, Rh, Pd, Ag, Cd, In, Sn) and 75–85 (Re, Os, Ir, Pt, Au, Hg, Ti, Pb, Bi, Po, At). Tc, Re, and Cu isotopes are particularly advantageous for use in diagnostic imaging and radiotherapy, more preferably $^{99m}$Tc. Other radionuclides with diagnostic or therapeutic applications include $^{62}$Cu, $^{64}$Cu, $^{67}$Cu, $^{97}$Ru, $^{105}$Rh, $^{109}$Pd, $^{186}$Re, $^{188}$Re, $^{198}$Au, $^{199}$Au, $^{203}$Pb, $^{211}$Pb and $^{212}$Bi. The particular medically useful metal ion depends on the specific application. The medically-useful metal ion is selected to have a higher order of binding than the positively charged-transition metal ion used to stabilize the metal binding sequences.

In the case of 99Tc, the peptides are reacted with sodium pertechnetate which has been treated with a reducing agent to generate Tc with a lower oxidation state. The product of the reaction between the metal ion and the peptide is a complex of the metal ion and the peptide.

Most stannous reductions are performed at a pH of from about 5 to about 7. With amino acid side chains in a solution below pH 7, the basic amino acids are positively charged, the acidic amino acids are largely negatively charged, the alcoholic amino acids are neutral, and methionine is neutral. Since reduced technetium binds more readily to neutral hydrogen donors rather than positively charged hydrogen donors, at the pH range 5 to 7 only Cys and His are optimal $^{99}$Tc binding site candidates. For both Cys and His, radiolabeling yields are dependant on pH, and are theoretically optimal at or near the $pK_a$.

For use as an in vivo diagnostic agent, a targeting moiety of the invention may advantageously be labeled with radioactive technetium or iodine. Accordingly, in one embodiment, the invention provides a modulator compound labeled with technetium, preferably $^{99m}$Tc. Methods for labeling peptide compounds with technetium are known in the art (see, e.g., U.S. Pat. Nos. 5,443,815, 5,225,180 and 5,405, 597, all by Dean et al.; Stepniak-Biniakiewicz, D., et al. (1992) *J. Med. Chem.* 35:274–279; Fritzberg, A. R., et al. (1988) *Proc. Natl. Acad. Sci. USA* 85:40254029; Baidoo, K. E., et al. (1990) *Cancer Res. Suppl.* 50:799s–803s; and Regan, L. and Smith, C. K. (1995) *Science* 270:980–982). A modifying group can be chosen that provides a site at which a chelation group for $^{99m}$Tc can be introduced, such as the Aic derivative of cholic acid, which has a free amino group.

The primary applications of the invention involve human patients, but the invention may be applied to laboratory, farm, zoo, wildlife, pet or sport animals. The invention may be used to monitor normal or abnormal metabolic events, to localize normal or abnormal tissues.

In one embodiment of a method for labeling peptides of the configurations set forth above, the following method can be employed:
  a) adding a source of positively-charged transition metal, most preferably a Sn (II) agent, to the peptide containing amino acids comprising sulfur, nitrogen or oxygen which is available for binding, or which can be made available for binding to metal ions, in an amount sufficient to allow the positively-charged transition metal to undergo a replacement reaction, thereby forming transition metal-containing and sulfur-, nitrogen- or oxygen-containing complexes, or some combination thereof; and,
  b) adding a medically useful metal ion whereby the metal ion displaces the transition metal in the transition metal-containing and sulfur-, nitrogen- or oxygen-containing complexes and the metal ion and peptide form metal ion-containing and sulfur-, nitrogen-, or oxygen-containing complexes.

A useful transition metal is Sn(II); useful sources of Sn(II) include stannous tartrate, stannous glucoheptonate, stannous gluconate, stannous phosphonate, stannous chloride, and stannous fluoride. The selection of the source of Sn(II) and its final concentration depends on, e.g., the intended medical application, the relative and absolute number of thiolate groups and the metal ion to be used. In one embodiment stannous tartrate is used at a concentration of 1.25 mM. The stannous tartrate is prepared in a buffer having 10 mM tartrate and 40 mM phthalate, pH 5.6, and is added to peptide to yield a final concentration of 1 mg/ml peptide solution.

Sn(II) can be stabilized by use of carboxylic acids, such as acetate, citrate, phthalate and tartrate. A wide range of dicarboxylic acids, known to those skilled in the art, may be similarly used to stabilize the Sn(II) and/or to act as a buffer. If the phthalate and tartrate are in molar excess relative to the Sn(II), then these dicarboxylic acids also stabilize the medically useful metal ion in a form which can react with the peptide. Tartrate and phthalate may be used in the Sn (II) agent, e.g., at 10 mM and 40 mM, respectively.

Similarly, the Sn(II) and the medically useful metal ion may be stabilized by free amino acids used singly or in combination with other agents. The type of amino acid used and the specific concentration depends on the nature of the peptide and its intended use. In one embodiment, glycine is used at a concentration of 0.1–10 mM, and in another, histidine is used at a concentration of 0.1–10 mM. In yet another embodiment, trace amounts of thiol-containing agent, such as cysteine, may be added to stabilize the Sn (II) and the medically useful metal ion.

The imaging agent may be stored in bulk form or in unit dose form after addition of the Sn(II) or other transition metal. For example, in one embodiment the peptide is stored at −20° C. in vials after introducing the Sn(II). Methods used in lyophilization of peptides are known to those skilled in the art. Either frozen or lyophilized preparations may be maintained for an indefinite period before labeling by the addition of the medically useful metal ion.

In both the frozen and lyophilized storage forms, excipients may be added to minimize damage which can arise from ice-crystal formation or free-radical formation. The type of excipient and the concentration depends on the nature of the peptide and the intended use. Glycine and inositol, for example, may be used as excipients in lyophilized preparations.

Magnetic resonance imaging (MRI) is a diagnostic and research procedure that uses high magnetic fields and radio-frequency signals to produce images. The most abundant molecular species in biological tissues is water. It is the quantum mechanical "spin" of the water proton nuclei that ultimately gives rise to the signal in all imaging experiments. In MRI the sample to be imaged is placed in a strong static magnetic field (1–12 Tesla) and the spins are excited with a pulse of radio frequency (RF) radiation to produce a net magnetization in the sample. Various magnetic field gradients and other RF pulses then act on the spins to code spatial information into the recorded signals. MRI is able to generate structural information in three dimensions in relatively short time spans.

MR images are typically displayed on a gray scale with black the lowest and white the highest measured intensity (I). This measured intensity I=C*M, where C is the concentration of spins (in this case, water concentration) and M is a measure of the magnetization present at time of the measurement. Although variations in water concentration (C) can give rise to contrast in MR images, it is the strong dependence of the rate of change of M on local environment that is the source of image intensity variation in MRI. Two characteristic relaxation times, $T_1$ and $T_2$, govern the rate at which the magnetization can be accurately measured. $T_1$ is the exponential time constant for the spins to decay back to equilibrium after being perturbed by the RF pulse. In order to increase the signal-to-noise ratio (SNR) a typical MR imaging scan (RF & gradient pulse sequence and data acquisition) is repeated at a constant rate for a predetermined number of times and the data averaged. The signal amplitude recorded for any given scan is proportional to the number of spins that have decayed back to equilibrium since the previous scan. Thus, regions with rapidly decaying spins (i.e., short $T_1$ values) will recover all of their signal amplitude between successive scans.

The measured intensities in the final image will accurately reflect the spin density (i.e., water content). Regions with long $T_1$ values compared to the time between scans will progressively lose signal until a steady state condition is reached and will appear as darker regions in the final image. Changes in $T_2$ (spin—spin relaxation time) result in changes in the signal linewidth (shorter $T_2$ values) yielding larger linewidths. In extreme situations the linewidth can be so large that the signal is indistinguishable from background noise. In clinical imaging, water relaxation characteristics vary from tissue to tissue, providing the contrast which allows the discrimination of tissue types. Moreover, the MRI experiment can be setup so that regions of the sample with short $T_1$ values and/or long $T_2$ values are preferentially enhanced so called $T_1$-weighted and $T_2$-weighted imaging protocol.

The capacity, with paramagnetic contrast agents, to differentiate regions/tissues that may be magnetically similar but histologically distinct is a major impetus for the preparation of these agents. In designing MRI agents, strict attention must be given to a variety of properties that will ultimately effect the physiological outcome apart from the ability to provide contrast enhancement. Two fundamental properties that must be considered are biocompatibility and proton relaxation enhancement. Biocompatibility is influenced by several factors including toxicity, stability (thermodynamic and kinetic), pharmacokinetics and biodistribution. Proton relaxation enhancement (or relaxivity) is chiefly governed by the choice of metal and rotational correlation times.

The first feature to be considered during the design stage is selecting the metal atom, which will dominate the measured relaxivity of the complex. Paramagnetic metal ions, as a result of their unpaired electrons, act as potent relaxation enhancement agents. They decrease the $T_1$ and $T_2$ relaxation times of nearby ($r_6$-dependence) spins. Some paramagnetic ions decrease the $T_1$ without causing substantial linebroadening (e.g., gadolinium (III), ($Gd^{3+}$)), while others induce drastic linebroadening (e.g., superparamagnetic iron oxide). The mechanism of $T_1$ relaxation is generally through a space dipole—dipole interaction between the unpaired electrons of the paramagnet (the metal atom with an unpaired electron) and bulk water molecules (water molecules that are not "bound" to the metal atom) that are in fast exchange with water molecules in the metal's inner coordination sphere (are bound to the metal atom).

For example, regions associated with a $Gd^{3+}$ ion (near-by water molecules) appear bright in an MR image where the normal aqueous solution appears as dark background if the time between successive scans in the experiment is short (i.e., $T_1$ weighted image). Localized $T_2$ shortening caused by superparamagnetic particles is believed to be due to the local magnetic field inhomogeneities associated with the large magnetic moments of these particles. Regions associated with a superparamagnetic iron oxide particle appear dark in an MR image, where the normal aqueous solution appears as high intensity background if the echo time (TE) in the spin-echo pulse sequence experiment is long (i.e., $T_2$-weighted image). The lanthanide atom $Gd^{3+}$ is frequently chosen for MRI contrast agents because it has a very high magnetic moment ($u^2=63$ $BM^2$), and a symrnmetric electronic ground state, ($S^8$). Transition metals such as high spin Mn(II) and Fe(III) are also candidates due to their high magnetic moments.

Once the appropriate metal has been selected, a suitable ligand or chelate must be found to render the complex nontoxic. The term chelator is derived from the Greek word chele which means a "crabs claw", an appropriate description for a material that uses its many "arms" to grab and hold on to a metal atom (e.g., DTPA). Several factors influence the stability of chelate complexes include enthalpy and entropy effects (e.g., number, charge and basicity of coordinating groups, ligand field and conformational effects). Various molecular design features of the ligand can be directly correlated with physiological results. For example, the presence of a single methyl group on a given ligand structure can have a pronounced effect on clearance rate. While the addition of a bromine group can force a given complex from a purely extracellular role to an effective agent that collects in hepatocytes.

Diethylenetriaminepentaacetic (DTPA) chelates and thus acts to detoxify lanthanide ions. The stability constant (K) for $Gd(DTPA)^{2-}$ is very high (log K=22.4) and is more commonly known as the formation constant (the higher the log K, the more stable the complex). This thermodynamic parameter indicates the fraction of $Gd^{3+}$ ions that are in the unbound state will be quite small and should not be confused with the rate (kinetic stability) at which the loss of metal occurs ($k^f/k^d$). The water soluble $Gd(DTPA)^{2-}$ chelate is stable, nontoxic, and one of the most widely used contrast enhancement agents in experimental and clinical imaging research. It is an extracellular agent that accumulates in tissue by perfusion dominated processes.

To date, a number of chelators have been used, including diethylenetriaminepentaacetic (DTPA), 1,4,7,10-tetraazacyclododecane'-N,N'N",N'''-tetracetic acid (DOTA), and derivatives thereof. See, e.g., U.S. Pat. Nos. 5,155,215, 5,087,440, 5,219,553, 5,188,816, 4,885,363, 5,358,704, 5,262,532; and Meyer et al., *Invest. Radiol.* 25: S53 (1990).

Image enhancement improvements using Gd(DTPA) are well documented, including visualizing blood-brain barrier disruptions caused by space occupying lesions and detection of abnormal vascularity. It has been applied to the functional mapping of the human visual cortex by defining regional cerebral hemodynamics.

Another chelator used in Gd contrast agents is the macrocyclic ligand 1,4,7,10-tetraazacyclododecane-N,N',N"N'''-tetracetic acid (DOTA). The Gd-DOTA complex has been thoroughly studied in laboratory tests involving animals and humans. The complex is conformationally rigid, has an extremely high formation constant (logK=28.5), and at physiological pH possess very slow dissociation kinetics. The Gd-DOTA complex has been approved as an MRI contrast agent for use in adults and infants in France, and has been administered to over 4500 patients.

Viewed simplistically, this "trigger" mechanism, whereby the contrast agent is "turned on" (i.e., increases the relaxivity) by the presence of the target substance, is based on a dynamic equilibrium that affects the rate of exchange of water molecules in one or more coordination sites of a paramagnetic metal ion contained in the MRI contrast agents of the present invention. In turn, the rate of exchange of the water molecule is determined by the presence or absence of the target substance in the surrounding environment. Thus, in the absence of the target substance, the metal ion complexes of the invention which chelate the paramagnetic ion have reduced coordination sites available which can rapidly exchange with the water molecules of the local environment. In such a situation, the water coordination sites are substantially occupied or blocked by the coordination atoms of the chelator and at least one blocking moiety. Thus, the paramagnetic ion has essentially no water molecules in its "inner-coordination sphere", i.e., actually bound to the metal when the target substance is absent. It is the interaction of the paramagnetic metal ion with the protons on the inner coordination sphere water molecules and the rapid exchange of such water molecules that cause the high observed relaxivity, and thus the imaging effect, of the paramagnetic metal ion. Accordingly, if all the coordination sites of the metal ion in the metal ion complex are occupied with moieties other than water molecules, as is the case when the target substance is absent, there is little if any net enhancement of the imaging signal by the metal ion complexes of the invention. However, when present, the target substance interacts with the blocking moiety or moieties of the metal ion complex, effectively freeing at least one of the inner-sphere coordination sites on the metal ion complex. The water molecules of the local environment are then available to occupy the inner-sphere coordination site or sites, which will cause an increase in the rate of exchange of water and relaxivity of the metal ion complex toward water thereby producing image enhancement which is a measure of the presence of the target substance.

Generally, a 2 to 5% change in the MRI signal used to generate the image is sufficient to be detectable. Thus, it is preferred that the agents of the invention in the presence of a target substance increase the MRI signal by at least 2 to 5% as compared to the signal gain the absence of the target substance. Signal enhancement of 2 to 90% is preferred.

There are a large number of known macrocyclic chelators or ligands which are used to chelate lanthanide and paramagnetic ions. See for example, Alexander, Chem. Rev. 95:273–342 (1995) and Jackels, Pharm. Med. Imag, Section III, Chap. 20, p645 (1990), expressly incorporated herein by reference, which describes a large number of macrocyclic chelators and their synthesis. Similarly, there are a number of patents which describe suitable chelators for use in the invention, including U.S. Pat. Nos. 5,155,215, 5,087,440, 5,219,553, 5,188,816, 4,885,363, 5,358,704, 5,262,532, and Meyer et al., Invest. Radiol. 25: S53 (1990), all of which are also expressly incorporated by reference.

Other suitable Gd(III) chelators are described in Alexander, supra, Jackels, supra, U.S. Pat. Nos. 5,155,215, 5,087,440, 5,219,553, 5,188,816, 4,885,363, 5,358,704, 5,262,532, and Meyer et al., Invest. Radiol. 25: S53 (1990), among others.

When the paramagnetic ion is Fe(III), appropriate chelators will have less than 6 coordination atoms, since Fe(III) is capable of binding 6 coordination atoms. Suitable chelators for Fe(III) ions are well known in the art, see e.g., Lauffer et al., J. Am. Chem. Soc. 109:1622 (1987); Lauffer, Chem. Rev. 87:901–927 (1987); and U.S. Pat. Nos. 4,885,363, 5,358,704, and 5,262,532, all which describe chelators suitable for Fe(III).

When the paramagnetic ion is Mn(II) ($Mn^{+2}$), appropriate chelators will have less than 5 or 6 coordination atoms, since Mn(II) is capable of binding 6 or 7 coordination atoms. Suitable chelators for Mn(II) ions are well known in the art; see for example Lauffer, Chem. Rev. 87:901–927 (1987) and U.S. Pat. Nos. 4,885,363, 5,358,704, and 5,262,532.

When the paramagnetic ion is Yt(III), appropriate chelators will have less than 7 or 8 coordination atoms, since Yt(III) is capable of binding 8 or 9 coordination atoms.

Suitable chelators for Yt(III) ions include, but are not limited to, DOTA and DPTA and derivatives thereof (see Moi et al., J. Am. Chem. Soc. 110:6266–6267 (1988)) and those chelators described in U.S. Pat. No. 4,885,363 and others, as outlined above.

When the paramagnetic ion is Dy+3 (Dy(III)), appropriate chelators will have less than 7 or 8 coordination atoms, since DyIII is capable of binding 8 or 9 coordination atoms. Suitable chelators are known in the art, as above.

Linker groups (sometimes depicted herein as $R_{26}$) may be used to optimize the steric considerations of the metal ion complex. That is, in order to optimize the interaction of the blocking moiety with the metal ion, linkers may be introduced to allow the functional blocking moiety to block or occupy the coordination site. In general, the linker group is chosen to allow a degree of structural flexibility. For example, when a blocking moiety interacts with a physiological agent which does not result in the blocking moiety being cleaved from the complex, the linker must allow some movement of the blocking moiety away from the complex, such that the exchange of water at least one coordination site is increased.

Figure 11:
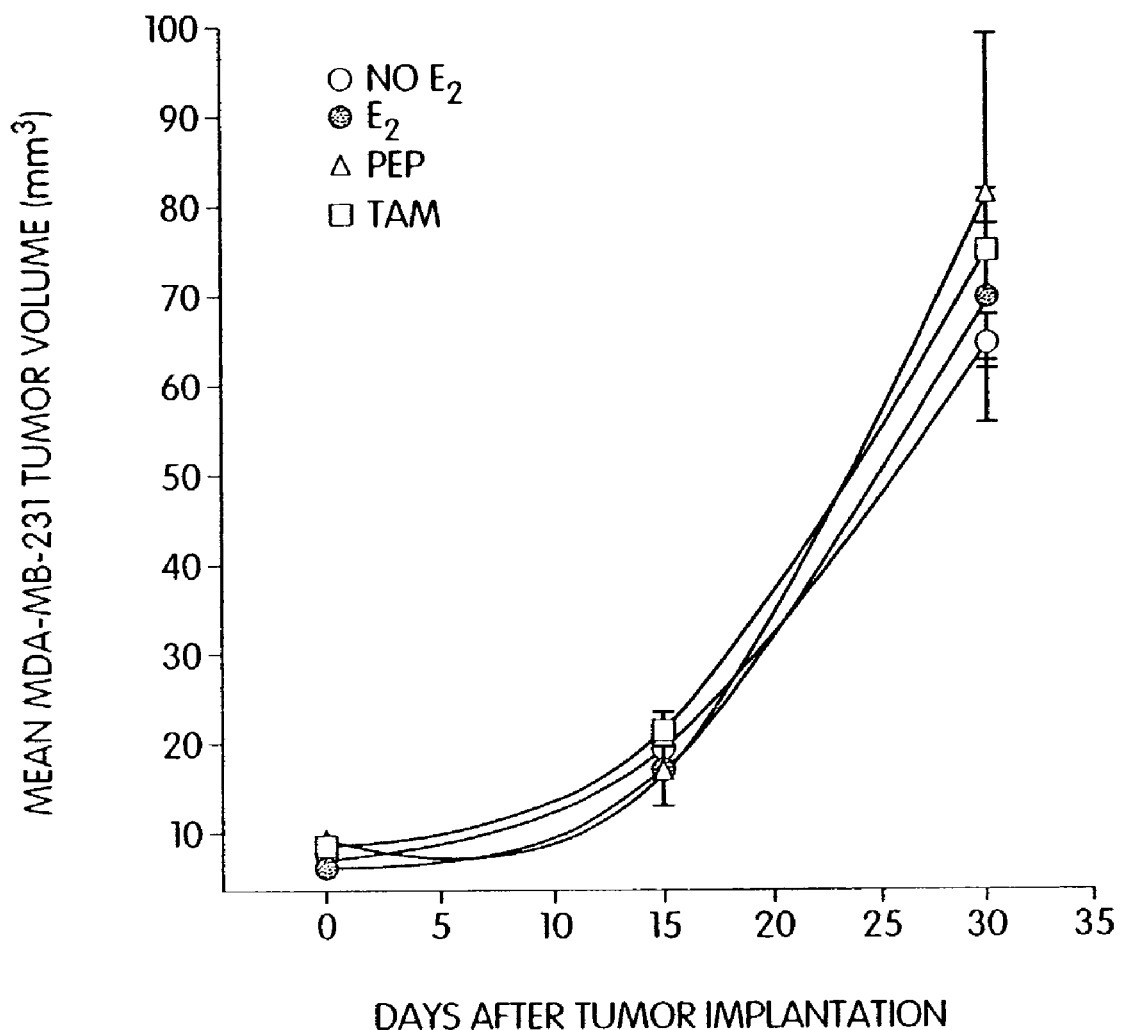
FIG. 11 illustrates the effect of AFP-derived peptide on growth of estrogen-receptor-negative MDA-MB-231 human breast cancer xenografts. See the legend to FIGS. 9a and 9b for the experimental protocol. There were no differences in tumor volumes between any of the groups.

Suitable linker groups include alkyl and aryl groups, including substituted alkyl and aryl groups and heteroalkyl (particularly oxo groups) and heteroaryl groups, including alkyl amine groups, as defined above. Preferred linker groups include p-aminobenzyl, substituted p-aminobenzyl, diphenyl and substituted diphenyl, alkyl furan such as benzylfuran, carboxy, and straight chain alkyl groups of 1 to 10 carbons in length. Particularly preferred linkers include p-aminobenzyl, methyl, ethyl, propyl, butyl, pentyl, hexyl, acetic acid, propionic acid, aminobutyl, p-alkyl phenols, 4-alkylimidazole. The selection of the linker group is generally done using well known molecular modeling techniques, to optimize the obstruction of the coordination site or sites of the metal ion. In addition, as outlined in the Examples, the length of this linker may be very important in order to achieve optimal results. As shown in FIG. 11, the length of the linker, i.e., the spacer between the chelator and the coordination atom(s) of the blocking moiety, contributes to the steric conformation and association of the coordination atoms with the metal ion, thus allowing excellent blocking of the metal ion by the blocking moiety.

The blocking moiety is attached to the metal ion complex in a variety of ways. In a preferred embodiment, as noted above, the blocking moiety is attached to the metal ion complex via a linker group. Alternatively, the blocking moiety is attached directly to the metal ion complex; for example, as outlined below, the blocking moiety may be a substituent group on the chelator.

In a preferred embodiment at least one of the R groups attached to the "arms" of the chelator comprises an alkyl (including substituted and heteroalkyl groups), or aryl (including substituted and heteroaryl groups), i.e., is a group sterically bulkier than hydrogen. This is particular useful to drive the equilibrium towards "locking" the coordination atom of the arm into place to prevent water exchange, as is known for standard MRI contrast agents. Preferred groups include the C1 through C6 alkyl groups with methyl being particularly preferred.

This is particularly preferred when the blocking moiety is attached via one of the "arms." However, the inclusion of too many groups may drive the equilibrium in the other direction effectively locking the coordination atom out of position. Therefore in a preferred embodiment only 1 or 2 of these positions is a non-hydrogen group, unless other methods are used to drive the equilibrium towards binding.

When the blocking moiety is not covalently tethered on two sides, blocking moieties and coordination site barriers are chosen to maximize three basic interactions that allow the blocking moiety to be sufficiently associated with the complex to hinder the rapid exchange of water in at least one coordination site of the complex. First, there may be electrostatic interactions between the blocking moiety and the metal ion, to allow the blocking moiety to associate with the complex. Secondly, there may be Van der Waals and dipole—dipole interactions. Thirdly, there may be ligand interactions, that is, one or more functionalities of the blocking moiety may serve as coordination atoms for the metal. In addition, linker groups may be chosen to force or favor certain conformations, to drive the equilibrium towards an associated blocking moiety. Similarly, removing degrees of freedom in the molecule may force a particular conformation to prevail. Similar restrictions can be made in the other embodiments, as will be appreciated by those in the art.

Furthermore, effective "tethering" of the blocking moiety down over the metal ion may also be done by engineering in other non-covalent interactions that will serve to increase the affinity of the blocking moiety to the chelator complex.

Potential blocking moieties may be easily tested to see if they are functional; that is, if they sufficiently occupy or block the appropriate coordination site or sites of the complex to prevent rapid exchange of water. Thus, for example, complexes are made with potential blocking moieties and then compared with the chelator without the blocking moiety in imaging experiments. Once it is shown that the blocking moiety is a sufficient "blocker", the target substance is added and the experiments repeated, to show that interaction with the target substance increases the exchange of water and thus enhances the image.

In a preferred embodiment, the MRI agents of the invention comprise at least two paramagnetic metal ions, each with a chelator and blocking moiety; that is, multimeric MRI agents are made. In a preferred embodiment, the chelators are linked together, either directly or through the use of a linker such as a coupling moiety or polymer. For example, using substitution groups that serve as functional groups for chemical attachment on the chelator, attachment to other chelators may be accomplished. As will be appreciated by those in the art, attachment of more than one MRI agent may also be done via the blocking moieties (or coordination site barriers, etc.), although these are generally not preferred.

In a preferred embodiment, the chelators of the invention include one or more substitution groups that serve as functional groups for chemical attachment. Suitable functional groups include, but are not limited to, amines (preferably primary amines), carboxy groups, and thiols (including SPDP, alkyl and aryl halides, maleimides, α-haloacetyls, and pyridyl disulfides) are useful as functional groups that can allow attachment.

In one embodiment, the chelators are linked together directly, using at least one functional group on each chelator. This may be accomplished using any number of stable bifunctional groups well known in the art, including homobifunctional and heterobifunctional linkers. This may result in direct linkage, for example when one chelator comprises a primary amine as a functional group and the second comprises a carboxy group as the functional group, and carbodiimide is used as an agent to activate the carboxy for attachment by the nucleophilic amine (see Torchilin et al., Critical Rev. Therapeutic Drug Carrier Systems, 7(4):275–308 (1991). Alternatively, as will be appreciated by those in the art, the use of some bifunctional linkers results in a short coupling moiety being present in the structure. A "coupling moiety" is capable of covalently linking two or more entities. In this embodiment, one end or part of the coupling moiety is attached to the first MRI contrast agent, and the other is attached to the second MRI agent. The functional group(s) of the coupling moiety are generally attached to additional atoms, such as alkyl or aryl groups (including hetero alkyl and aryl, and substituted derivatives), to form the coupling moiety. Oxo linkers are also preferred. As will be appreciated by those in the art, a wide range of coupling moieties are possible, and are generally only limited by the ability to synthesize the molecule and the reactivity of the functional group. Generally, the coupling moiety comprises at least one carbon atom, due to synthetic requirements; however, in some embodiments, the coupling moiety may comprise just the functional group.

In a preferred embodiment, the coupling moiety comprises additional atoms as a spacer. As will be appreciated by those in the art, a wide variety of groups may be used. For example, a coupling moiety may comprise an alkyl or aryl group substituted with one or more functional groups. Thus, in one embodiment, a coupling moiety containing a multiplicity of functional groups for attachment of multiple MRI contrast agents may be used, similar to the polymer embodiment described below. For example, branched alkyl groups containing multiple functional groups may be desirable in some embodiments.

In an additional embodiment, the linker is a polymer. In this embodiment, a polymer comprising at least one MRI contrast agent of the invention is used. As will be appreciated by those in the art, these MRI contrast agents may be monomeric (i.e., one metal ion, one chelator, one blocking moiety) or a duplex (i.e., two metal ions, two chelators, one blocking moiety). Preferred embodiments utilize a plurality of MRI agents per polymer. The number of MRI agents per polymer will depend on the density of MRI agents per unit length and the length of the polymer.

The character of the polymer will vary, but what is important is that the polymer either contain or can be modified to contain functional groups for the attachment of the MRI contrast agents of the invention. Suitable polymers include, but are not limited to, functionalized dextrans, styrene polymers, polyethylene and derivatives, polyanions including, but not limited to, polymers of heparin, polygalacturonic acid, mucin, nucleic acids and their analogs including those with modified ribose-phosphate backbones, the polypeptides polyglutamate and polyaspartate, as well as carboxylic acid, phosphoric acid, and sulfonic acid derivatives of synthetic polymers; and polycations, including but not limited to, synthetic polycations based on acrylamide and 2-acrylamido-2-methylpropanetrimethylamine, poly(N-ethyl-4-vinylpyridine) or similar quartemized polypyridine, diethylaminoethyl polymers and dextran conjugates, polymyxin B sulfate, lipopolyamines, poly(allylamines) such as the strong polycation poly(dimethyldiallylammonium chloride), polyethyleneimine, polybrene, spermine, spermidine and polypeptides such as protamine, the histone polypeptides, polylysine, polyarginine and polyornithine; and mixtures and derivatives of these. Particularly preferred polycations are polylysine and spermidine, with the former being especially preferred. Both optical isomers of polylysine can be used. The D isomer has the advantage of having long-term resistance to cellular proteases. The L isomer has the advantage of being more rapidly cleared from the subject. As will be appreciated by those in the art, linear and branched polymers may be used.

A preferred polymer is polylysine, as the —NH$_2$ groups of the lysine side chains at high pH serve as strong nucleophiles for multiple attachment of activated chelating agents. At high pH the lysine monomers are coupled to the MRI agents under conditions that yield on average 5–20% monomer substitution.

In some embodiments, particularly when charged polymers are used, there may be a second polymer of opposite charge to the first that is electrostatically associated with the first polymer, to reduce the overall charge of polymer-MRI agent complex. This second polymer may or may not contain MRI agents.

The size of the polymer may vary substantially. For example, it is known that some nucleic acid vectors can deliver genes up to 100 kilobases in length, and artificial chromosomes (megabases) have been delivered to yeast. Therefore, there is no general size limit to the polymer. However, a preferred size for the polymer is from about 10 to about 50,000 monomer units, with from about 2000 to about 5000 being particularly preferred, and from about 3 to about 25 being especially preferred.

It should be understood that the multimeric MRI agents of the invention may be made in a variety of ways, including those listed above. What is important is that manner of attachment does not significantly alter the functionality of the agents; that is, the agents must still be "off" in the absence of the target substance and "on" in its presence.

In a preferred embodiment, the MRI contrast agents of the invention are "duplexes". In this embodiment, the MRI duplex comprises two chelators, each with a paramagnetic metal ion, and at least one blocking moiety that restricts the exchange of water in at least one coordination site of each chelator. In this way, a sort of signal amplification occurs, with two metal ions increasing the signal with a single target molecule. While "duplex" implies two chelators, it is intended to refer to complexes comprising a single blocking moiety donating coordination atoms to more than 1 metal ion/chelator complex. As will be appreciated by those in the art, the MRI agents of this embodiment may have a number of different conformations. As outlined above, the MRI duplex moieties may also be combined into higher multimers, either by direct linkage or via attachment to a polymer.

In addition, the complexes and metal ion complexes of the invention may further comprise one or more targeting moieties, e.g., as disclosed herein. That is, a targeting moiety may be attached at any of the R positions (or to a linker, including a polymer, or to a blocking moiety, etc.), although in a preferred embodiment the targeting moiety does not replace a coordination atom.

In a preferred embodiment, the metal ion complexes of the present invention are water soluble or soluble in aqueous solution. By "soluble in aqueous solution" herein is meant that the MRI agent has appreciable solubility in aqueous solution and other physiological buffers and solutions. Solubility may be measured in a variety of ways. In one embodiment, solubility is measured using the United States Pharmacopeia solubility classifications, with the metal ion complex being either very soluble (requiring less than one part of solvent for 1 part of solute), freely soluble (requiring one to ten parts solvent per 1 part solute), soluble (requiring ten to thirty parts solvent per 1 part solute), sparingly soluble (requiring 30 to 100 parts solvent per 1 part solute), or slightly soluble (requiring 100–1000 parts solvent per 1 part solute). Testing whether a particular metal ion complex is soluble in aqueous solution is routine, as will be appreciated by those in the art. For example, the parts of solvent required to solubilize a single part of MRI agent may be measured, or solubility in gm/ml may be determined.

The complexes of the invention are generally synthesized using well known techniques. See, for example, Moi et al., supra; Tsien et al., supra; Borch et al., J. Am. Chem. Soc., p2987 (1971); Alexander, (1995), supra; Jackels (1990), supra, U.S. Pat. Nos. 5,155,215, 5,087,440, 5,219,553, 5,188,816, 4,885,363, 5,358,704, 5,262,532; Meyer et al., (1990), supra, Moi et al., (1988), and McMurray et al., Bioconjugate Chem. 3(2):108–117 (1992)).

Figure 3A:
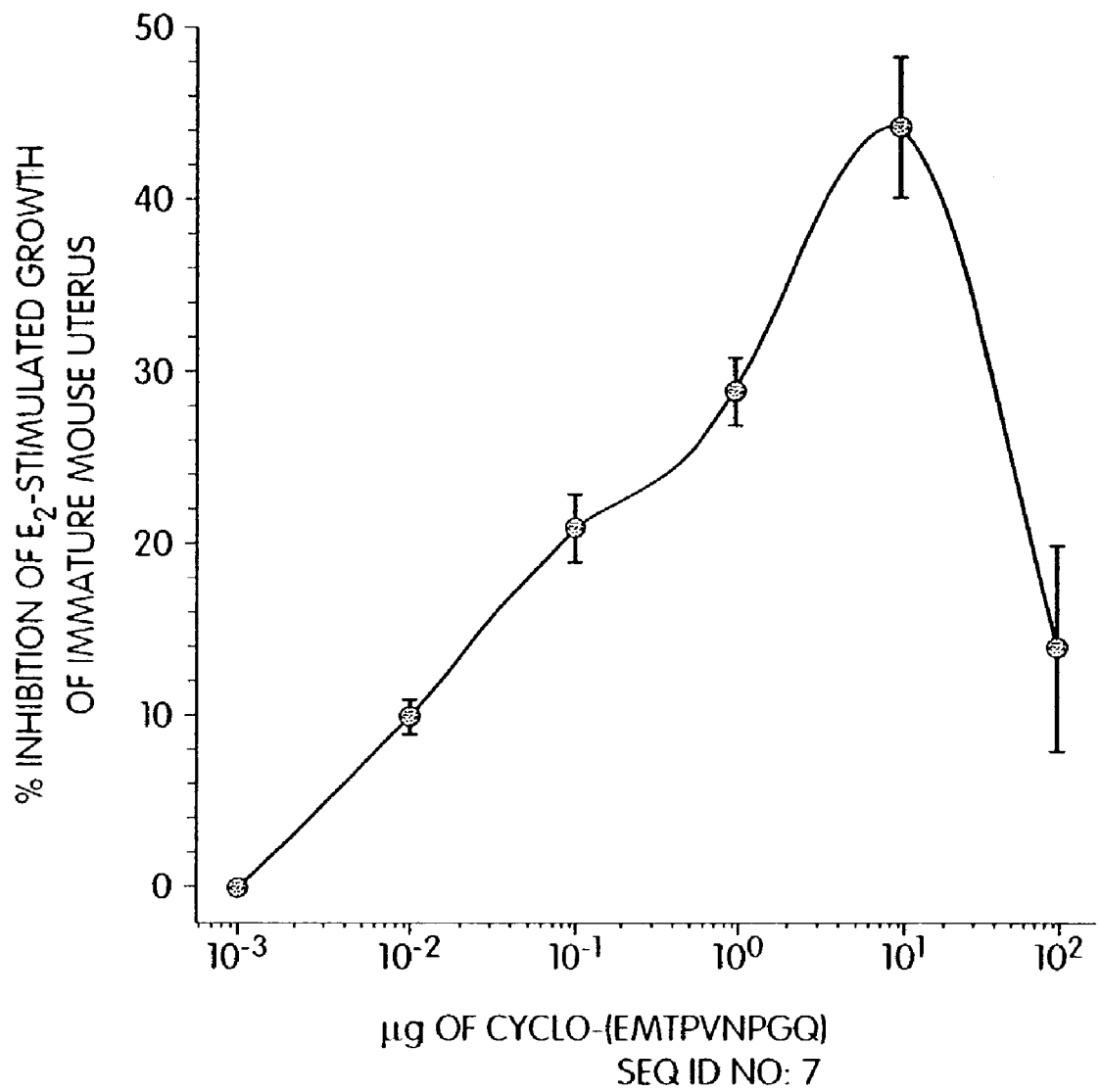
FIGS. 3a and 3b illustrate the anti-uterotrophic activity of cyclo-(SEQ ID NO: 7, EMTPVNPGQ).
Figure 3B:
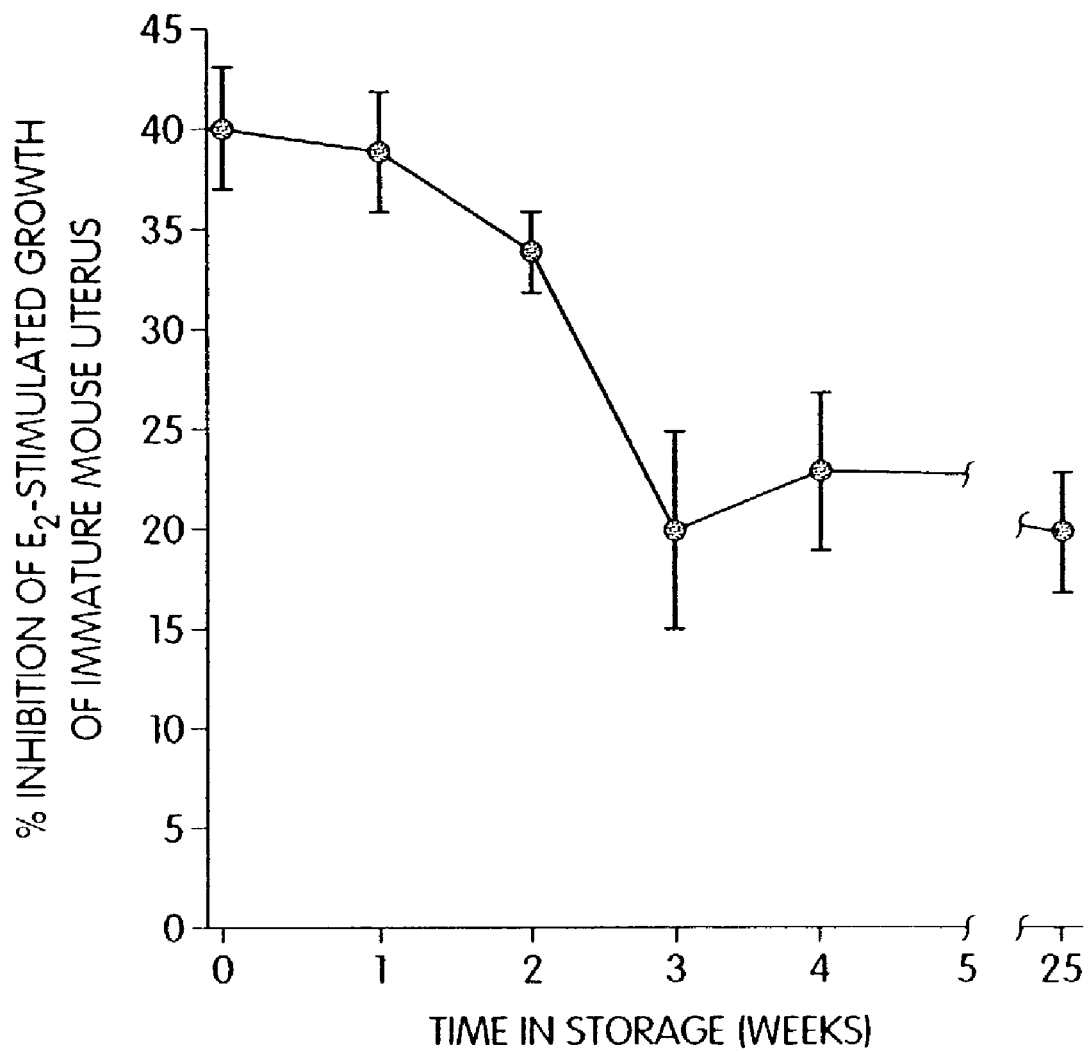
Figure 4B:
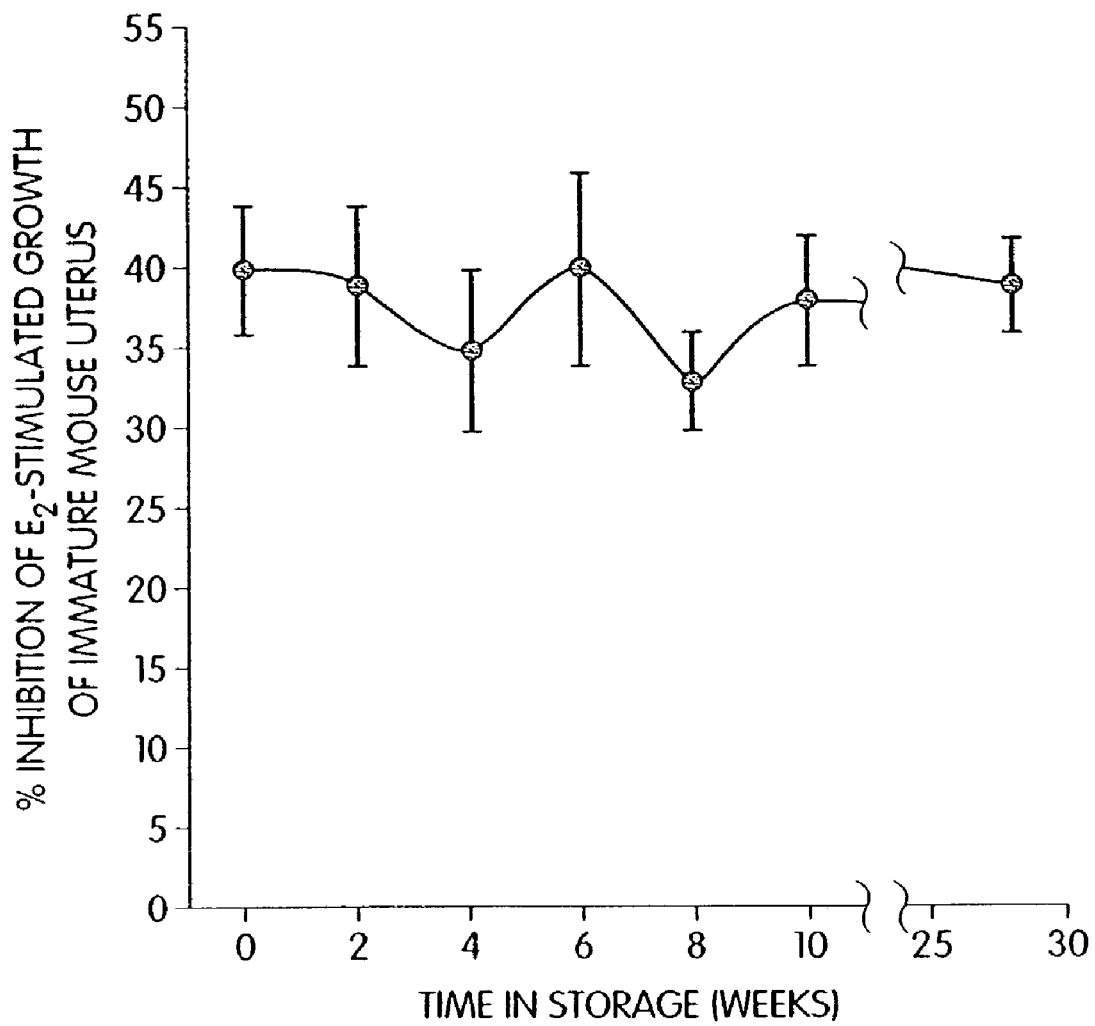
Figure 5:
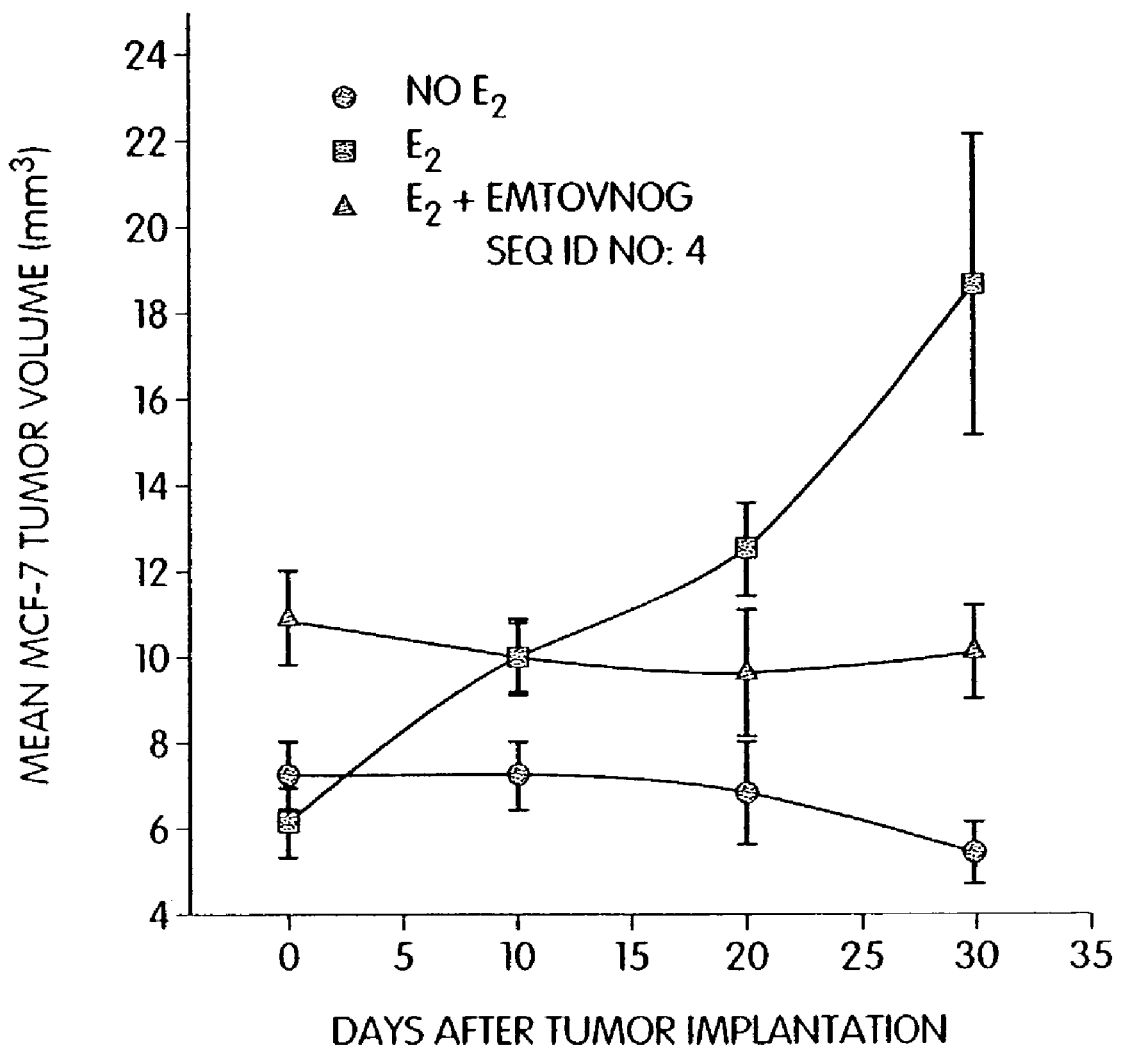
FIG. 5 illustrates the anti-estrotrophic activity of hydroxyproline-substituted linear peptide against MCF-7 human breast cancer xenografts. There were five to eight replicate mice per treatment group. Estrogen was provided via a slow release pellet implanted subcutaneously. Peptide was given twice a day i.p. at a dose of 1 μg per mouse. Tumor volumes in each mouse were measured at the time of tumor implantation and at 10-day intervals thereafter during survival laparotomies. At 30 days after tumor implantation, tumor volumes in the $E_2$+ peptide group were significantly different from tumor volumes in the $E_2$ alone group, $p \leq 0.05$; Wilcoxon ranks-sum test.
Figure 6B:
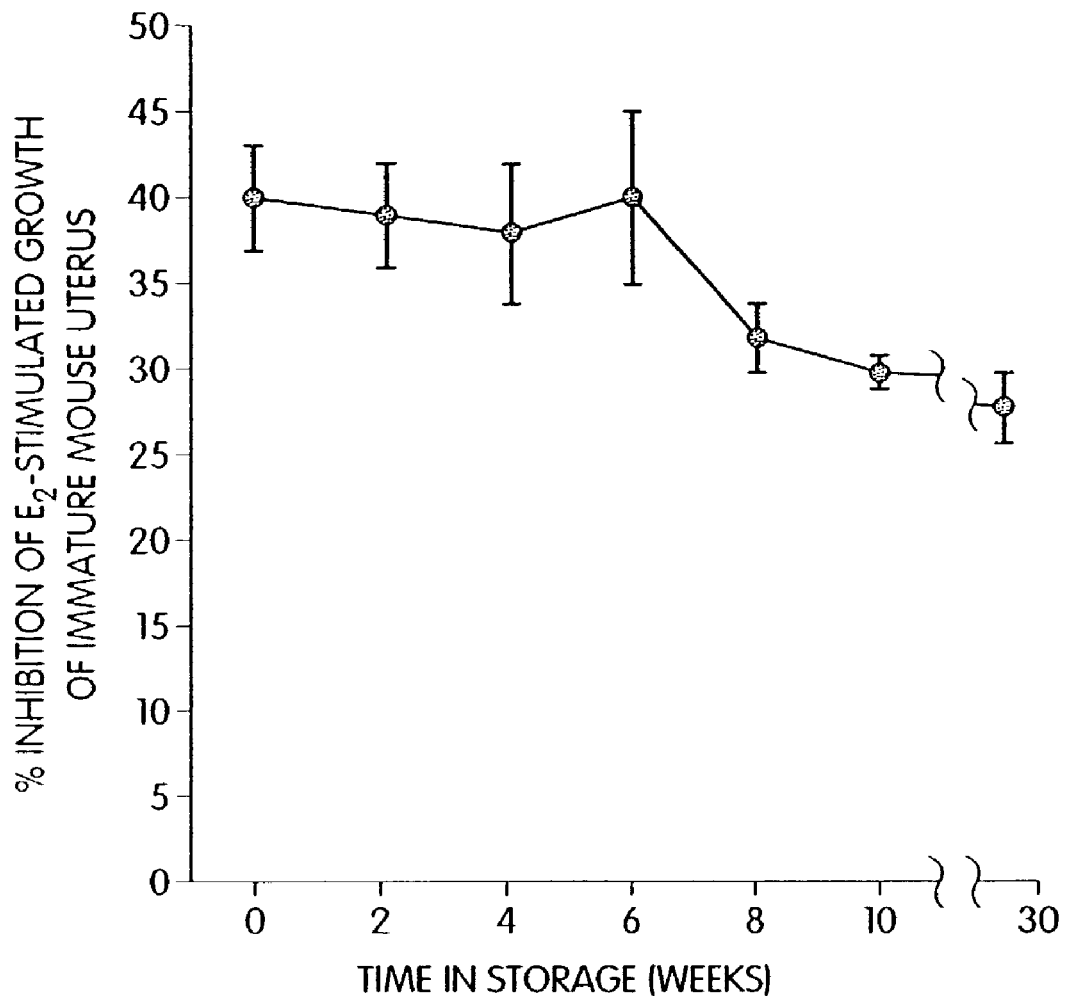
Figure 7:
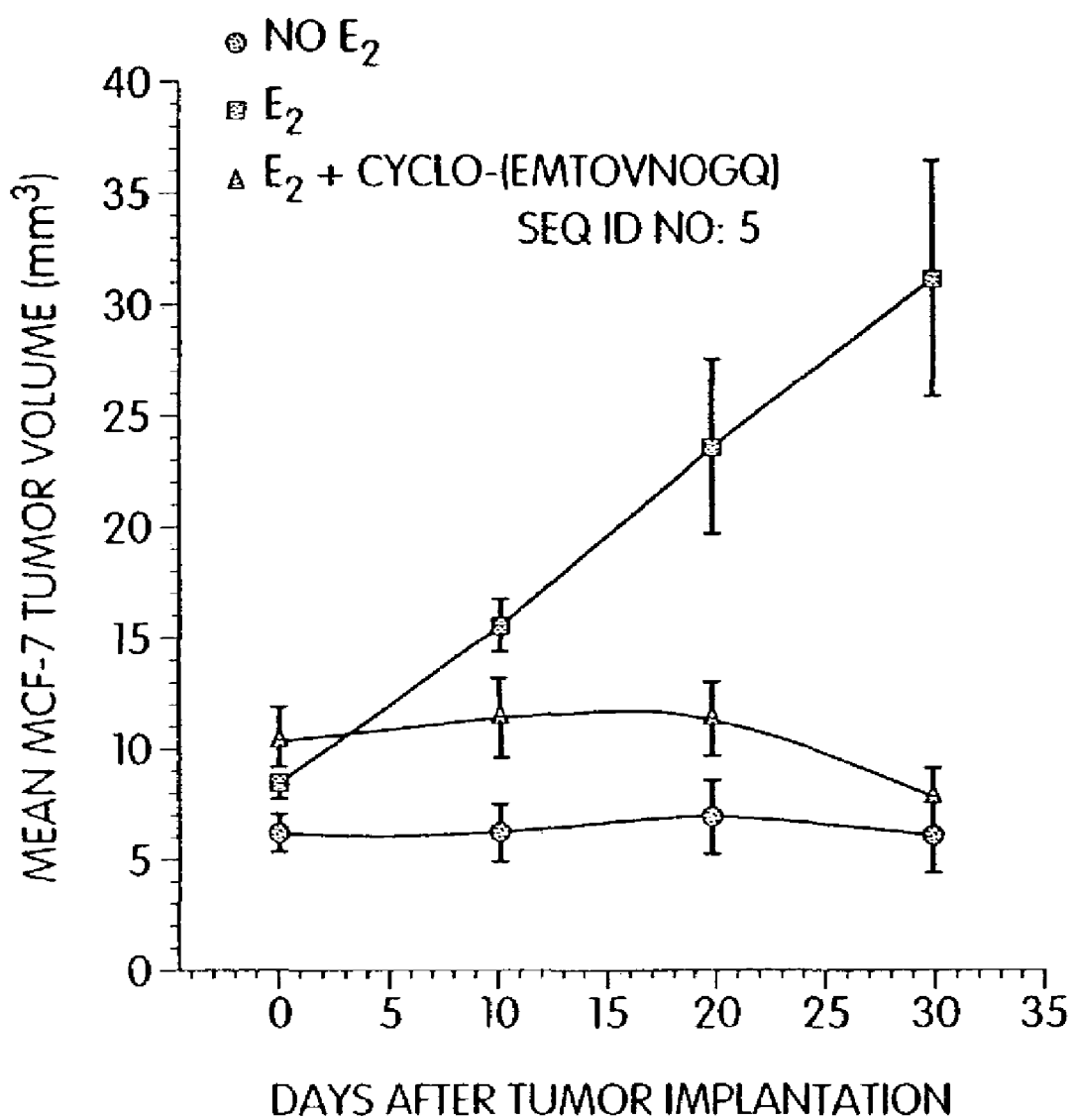
FIG. 7 illustrates the anti-estrotrophic activity of cyclized peptide with hydroxyproline substituted for proline against MCF-7 human breast cancer xenografts. The experimental protocol is described in the legend to FIG. 5, and in the Materials and Methods. At 20 days and 30 days after tumor implantation, tumor volumes in the $E_2$+peptide group were significantly different from tumor volumes in the $E_2$ alone group, $p<0.05$; Wilcoxon ranks-sum test.
Figure 8:
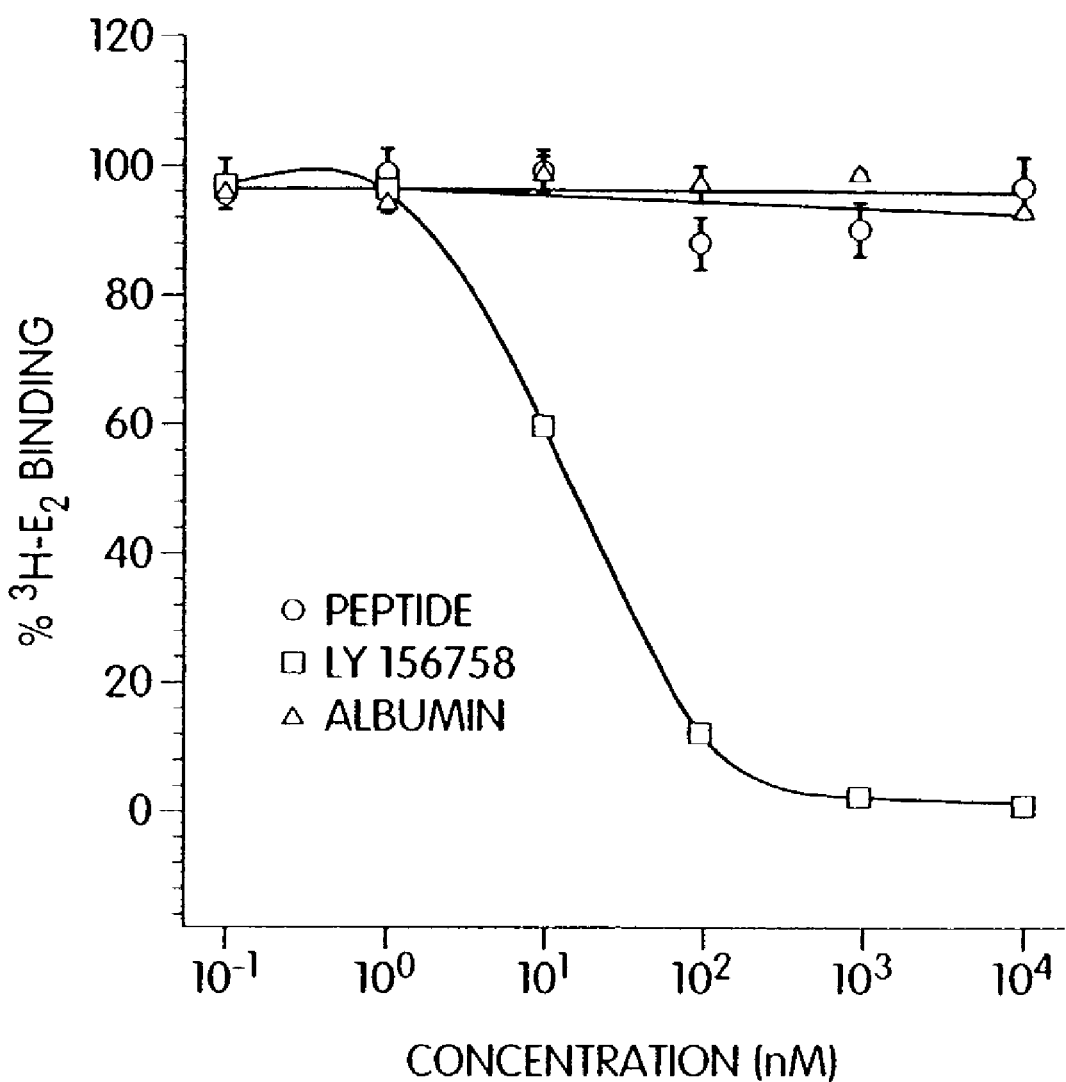
FIG. 8 illustrates the effect of linear hydroxyproline-substituted peptide on binding of $E_2$ to its receptor. Rabbit uterine cytosol was used as a source of estrogen receptor. All incubations were performed in triplicate, each containing 100 μl of cytosol, 20 μl of 10 nM 6,7-$^3$H estradiol (50 Ci/mmol), and 80 μl of test agent at the final concentrations indicated on the abscissa. Details of the assay are described in Materials and Methods. Concentration of [$^3$E]$E_2$-Complex with receptor in the presence of different concentrations of test agent is expressed as a percentage of the amount of complex formed in the absence of test agent.

For DOTA derivatives, the synthesis depends on whether nitrogen substitution or carbon substitution of the cyclen ring backbone is desired. For nitrogen substitution, such as is exemplified by the galactose-DOTA structures of the examples, the synthesis begins with cyclen or cyclen derivatives, as is well known in the art; see for example U.S. Pat. Nos. 4,885,363 and 5,358,704. FIGS. 3 and 4 depict the nitrogen substitution as exemplified by galactose-DOTA derivatives.

For carbon substitution, such as is exemplified by the BAPTA-DOTA structures of the examples, well known techniques are used. See for example Moi et al., supra, and Gansow, supra.

The contrast agents of the invention are complexed with the appropriate metal ion as is known in the art. While the structures depicted herein all comprise a metal ion, it is to be understood that the contrast agents of the invention need not have a metal ion present initially. Metal ions can be added to water in the form of an oxide or in the form of a halide and treated with an equimolar amount of a contrast agent composition. The contrast agent may be added as an aqueous solution or suspension. Dilute acid or base can be added if need to maintain a neutral pH. Heating at temperatures as high as 100° C. may be required.

Once synthesized, the metal ion complexes of the invention have use as magnetic resonance imaging contrast or enhancement agents. Specifically, the functional MRI agents of the invention have several important uses. First, they may be used to diagnose disease states of the brain, as is outlined below. Second, they may be used in real-time detection and differentiation of myocardial infraction versus ischemia. Third, they may be used in vivo, i.e., whole organism, investigation of antigens and immunocytochemistry for the location of tumors. Fourth, they may be used in the identification and localization of toxin and drug binding sites. In addition, they may be used to perform rapid screens of the physiological response to drug therapy.

The metal ion complexes of the invention may be used in a similar manner to the known gadolinium MRI agents. See for example, Meyer et al., supra; U.S. Pat. No. 5,155,215; U.S. Pat. No. 5,087,440; Margerstadt et al., Magn. Reson. Med. 3:808 (1986); Runge et al., Radiology 166:835 (1988); and Bousquet et al., Radiology 166:693 (1988). The metal ion complexes are administered to a cell, tissue or patient as is known in the art. A "patient" for the purposes of the present invention includes both humans and other animals and organisms, such as experimental animals. Thus the methods are applicable to both human therapy and veterinary applications. In addition, the metal ion complexes of the invention may be used to image tissues or cells; for example, see Aguayo et al., Nature 322:190 (1986).

Generally, sterile aqueous solutions of the contrast agent complexes of the invention are administered to a patient in a variety of ways, including orally, intrathecally and especially intraveneously in concentrations of 0.003M to 1.0M, with dosages from 0.03, 0.05, 0.1, 0.2, and 0.3 millimoles per kilogram of body weight being preferred. Dosages may depend on the structures to be imaged. Suitable dosage levels for similar complexes are outlined in U.S. Pat. Nos. 4,885,363 and 5,358,704.

In addition, the contrast agents of the invention may be delivered via specialized delivery systems, for example, within liposomes (see Navon, Magn. Reson. Med. 3:876–880 (1986)) or microspheres, which may be selectively taken up by different organs (see U.S. Pat. No. 5,155,215).

In some embodiments, it may be desirable to increase the blood clearance times (or half-life) of the MRI agents of the invention. This has been done, for example, by adding carbohydrate polymers to the chelator (see U.S. Pat. No. 5,155,215). Thus, one embodiment utilizes polysaccharides as substitution R groups on the compositions of the invention.

A modulator compound of the invention can be further modified to alter the specific properties of the compound while retaining the ability of the compound to alter cell proliferation. For example, in one embodiment, the compound is further modified to alter a pharmacokinetic property of the compound, such as in vivo stability or half-life. In another embodiment, the compound is further modified to label the compound with a detectable substance. In yet another embodiment, the compound is further modified to couple the compound to an additional therapeutic moiety. Schematically, a modulator of the invention comprising an amino acid core domain coupled directly or indirectly to at least one modifying group can be illustrated as MG-ACD, whereas this compound which has been further modified to alter the properties of the modulator can be illustrated as MG-ACD-CM, wherein CM represents an additional chemical modification.

To further chemically modify the compound, such as to alter the pharmacokinetic properties of the compound, reactive groups can be derivatized. For example, when the modifying group is attached to the amino-terminal end of the aggregation core domain, the carboxy-terminal end of the compound can be further modified. Preferred C-terminal modifications include those which reduce the ability of the compound to act as a substrate for carboxypeptidases. Examples of preferred C-terminal modifiers include an amide group (i.e., a peptide amide), an alkyl or aryl amide group (e.g., an ethylamide group or a phenethylamide group) a hydroxy group (i.e., a peptide alcohol) and various non-natural amino acids. Alternatively, when the modifying group is attached to the carboxy-terminal end of the aggregation core domain, the amino-terminal end of the compound can be further modified, for example, to reduce the ability of the compound to act as a substrate for aminopeptidases.

The invention provides diagnostic procedures wherein the presence or absence of a cell-proliferating disorder, e.g., a breast cancer, may be determined. The imaging agents of the invention include alpha-fetoprotein hydrophilic analogs which have been determined to target cancers, e.g., breast cancer, and are also anti-cell proliferating in nature. The imaging agents of the invention further comprise an imaging moiety that allows for the imaging of the area targeted by the imaging agent. The imaging moiety can be integral to the targeting moiety, e.g., by radiolabeling one of the atoms, or by means of an imaging moiety attached to the targeting moiety, such as a chelating agent, e.g., a bifunctional agent, which binds a medically useful metal ion to the peptide via the chelating agent.

In an embodiment, cancer imaging and/or diagnostic methods of the invention include administering an effective amount of a labeled alpha-fetoprotein peptide eight to twenty amino acids in length, where the labeled peptide comprises an alpha-fetoprotein peptide hydrophilic analog having the sequence EMTPVNPG (SEQ ID NO:6) and a medically useful metal ion to a patient, allowing for localization of the labeled peptide, and imaging the labeled peptide. The medically useful metal ion may be, e.g., iron, cobalt, nickel, copper, zinc, arsenic, selenium, molybdenum, technetium, e.g., technetium-99m; ruthenium, palladium, silver, cadmium, indium, antimony, rhenium, e.g., rhenium-186 or rhenium-188; osmium, iridium, platinum, gold, mercury, thallium, lead, bismuth, polonium or astatine. The medically useful metal ion may be radioactive, paramagnetic or superparamagnetic.

The imaging agents may be used in methods of diagnosing cell-proliferating disorders such as breast cancer in accordance with the invention, e.g., providing a medically useful metal ion-labeled alpha-fetoprotein peptide comprising a peptide sequence eight to twenty amino acids long which comprises a hydrophilic analog of an alpha-fetoprotein peptide having one of the sequences noted above, e.g., EKTOVNOGN (SEQ ID NO: 1); QMTPVNPG (SEQ ID NO:2); QMTPVNPGE (SEQ ID NO:3); EMTOVNOG (SEQ ID NO:4); EMTOVNOGQ (SEQ ID NO:5); EMTPVNPG (SEQ ID NO:6); EMTPVNPGQ (SEQ ID NO:7); EMTOVNPGQ (SEQ ID NO:8); or EMTPVNOGQ (SEQ ID NO:9) and a medically useful metal ion, administering an effective amount of the labeled alpha-fetoprotein peptide to the patient, allowing for localization of the labeled peptide; and imaging the labeled alpha-fetoprotein peptide.

The administration may be by parenteral injection, e.g., intradermal, subcutaneous, intramuscular, intraperitoneal, or intravenous injection.

The invention also relates in an embodiment to methods of labeling alpha-fetoprotein peptides with a metal ion, by contacting an alpha-fetoprotein peptide solution (e.g., an alpha-fetoprotein peptide with a targeting moiety having the amino acid sequence EMTPVNPG (SEQ ID NO:6), or a hydrophilic analog of an alpha-fetoprotein peptide having one of the sequences noted above, e.g., EKTOVNOGN (SEQ ID NO: 1); QMTPVNPG (SEQ ID NO:2); QMTPVN-PGE (SEQ ID NO:3); EMTOVNOG (SEQ ID NO:4); EMTOVNOGQ (SEQ ID NO:5); EMTPVNPG (SEQ ID NO:6); EMTPVNPGQ (SEQ ID NO:7); EMTOVNPGQ (SEQ ID NO:8); or EMTPVNOGQ (SEQ ID NO:9), and a metal ion-binding domain), with a metal ion, and recovering the radiolabeled peptide. The solution may include excess stannous ions, i.e., greater than that required to completely reduce the metal ion. The metal ions may be, e.g., technetium in the pertechnetate form, or rhenium in the perrhenate form, e.g., rhenium-188 or rhenium-186. In a more particular embodiment for radiolabeling, alpha-fetoprotein peptides of the invention having a targeting moiety having a sequence (e.g., as noted above) and a metal ion-binding domain, may be labeled with a radioisotope of technetium or rhenium by contacting a solution of the peptide with stannous ions that are sufficient to reduce the radioisotope added in a subsequent step; reacting the peptide sequence and stannous ion solution with a radioisotope; and recovering the radiolabeled peptide. Before reacting the peptide sequence and stannous ion solution with a radioisotope, the solution may be lyophilized.

Imaging agents of the invention are also disclosed herein, which are suitable for imaging via MRI. The agents include a paramagnetic metal ion bound to a complex which includes a chelator and a targeting moiety, comprising an alpha-fetoprotein peptide, e.g., having a peptide sequence eight to twenty amino acids long, which comprises a hydrophilic analog of an alpha-fetoprotein peptide, e.g., having one of the sequences described herein. The targeting moiety is covalently attached to said chelator which binds in at least a first coordination site of the metal ion and which is capable of interacting with a target substance such that the exchange of water in at least the first coordination site is increased. The chelator may be, e.g., DOTA or DPTA, or may comprise a polymer backbone. The paramagnetic metal ion(s) may be, e.g., Gd(III), Fe(III), Mn(II), Yt(III), Cr(III) or Dy(III). Gd(III) is particularly useful.

Alternately, additional imaging agents of the invention are also disclosed. The agents include a paramagnetic metal ion capable of binding n coordination atoms, wherein the metal ion is bound to a chelator such that the metal ion has coordination atoms at (n–1) or (n–2) coordination sites of the metal ion; and a targeting moiety, comprising an alpha-fetoprotein peptide, e.g., having a peptide sequence eight to twenty amino acids long, which comprises a hydrophilic analog of an alpha-fetoprotein peptide, e.g., having one of the sequences described herein. The targeting moiety is desirably covalently attached to the chelator that hinders the rapid exchange of water in the remaining coordination site or sites, and is capable of interacting with a target substance, such that the exchange of water at the remaining coordination site or sites is increased. These imaging agents may desirably include, as the metal ion, a Gd(III) ion, e.g., with coordination atoms at 8 coordination sites of the Gd(III) ion; and, as the targeting moiety, one which hinders the rapid exchange of water in a 9th coordination site, wherein the targeting moiety is capable of interacting with a target substance, such that the exchange of water at the 9th coordination site is increased.

The invention also includes methods for magnetic resonance imaging of a cell, tissue or patient, comprising administering an imaging agent of the invention to a cell, tissue or patient and rendering a magnetic resonance image of the cell, tissue or patient.

In an alternative chemical modification, a targeting moiety of the invention is prepared in a "prodrug" form, wherein the compound itself does not modulate cell proliferation, but rather is capable of being transformed, upon metabolism in vivo, into a modulator compound. For example, in this type of compound, the modulating group can be present in a prodrug form that is capable of being converted upon metabolism into the form of an active modulating group. Such a prodrug form of a modifying group is referred to herein as a "secondary modifying group." A variety of strategies are known in the art for preparing peptide prodrugs that limit metabolism in order to optimize delivery of the active form of the peptide-based drug (see e.g., Moss, J. (1995) in *Peptide-Based Drug Design: Controlling Transport and Metabolism*, Taylor, M. D. and Amidon, G. L. (eds), Chapter 18.) Additionally, strategies have been specifically tailored to achieving CNS delivery based on "sequential metabolism" (see e.g., Bodor, N., et al. (1992) *Science* 257:1698–1700; Prokai, L., et al. (1994) *J. Am. Chem. Soc.* 116:2643–2644; Bodor, N. and Prokai, L. (1995) in *Peptide-Based Drug Design: Controlling Transport and Metabolism*, Taylor, M. D. and Amidon, G. L. (eds), Chapter 14.

The targeting moiety peptides have been designed as therapeutic agents that are effective against breast cancer. They may also be used against prostate cancer and other cancers which are affected by the steroid hormone/thyroid hormone superfamily of receptors. It is contemplated that these peptides or analogs can serve as first-line defense agents, and alternatively they may serve as adjunct therapeutic agents.

The inventors, while not wishing to be limited to a particular method or theory of how the present invention operates, have performed experiments using T-47D cells cultured with estradiol plus targeting moiety peptides of the invention, estradiol alone, peptide alone, or no additives (control). It was found that the level of MAP kinase enzyme (nuclear as well as cytoplasmic) that is induced by estradiol alone is reduced by half in cells cultured with estradiol plus peptide. There was a corresponding reduction in the phosphorylation of serine 118 on the estrogen receptor. Treatment with the targeting moiety peptide alone produced no effect on the level of MAP kinase.

In a cell-free system, it has been established that targeting moiety peptide does not compete with estrogen for binding to the estrogen receptor. In mice, we have found that daily administration of therapeutic doses of peptide does not reduce the level of serum estrogen. In fact, it appears that administration of therapeutic doses of peptide does lead to a slight increase in levels of both estrogen and progesterone. Thus it appears that the peptides of the invention may be used, particularly in combination with estradiol, in applications where, e.g., competitive competition of the therapeutic agent with the estrogen receptor is undesirable, or where it is undesirable to alter estrogen levels.

To "expose" cells (including the cells of tissues) to a targeting moiety peptide includes adding the peptide, usually in a liquid carrier, to a cell suspension or tissue sample in vitro, or administering the peptide to cells or tissues within an animal (including a human) subject in vivo.

For therapeutics, the formulation of therapeutic compositions and their subsequent administration is believed to be within the skill in the art. In order to improve stability and shelf-life, the peptide may be formulated as a composition including a stabilization excipient such as dodecyl maltoside or mannitol. In general, for therapeutics, a patient suspected of needing such therapy is given a peptide in accordance with the invention, commonly in a pharmaceutically acceptable carrier, in amounts and for periods which will vary depending upon the nature of the particular disease, its severity and the patient's overall condition. The pharmaceutical compositions may be administered in a number of ways depending upon whether local or systemic treatment is desired and upon the area to be treated. Administration may be topical (including ophthalmic, vaginal, rectal, intranasal, transdermal), oral or parenteral. Parenteral administration includes intravenous drip or infusion, subcutaneous, intraperitoneal or intramuscular injection, pulmonary administration, e.g., by inhalation or insufflation, or intrathecal or intraventricular administration.

The targeting moiety peptides and peptidomimetics thereof (including mimotopes and anti-mimotopes) can be made using various methods known in the art. A monoclonal antibody can be prepared which specifically binds to the peptide, thereby interfering with activity. The monoclonal antibodies can be produced by hybridomas. A hybridoma is an immortalized cell line which is capable of secreting a specific monoclonal antibody. In general, techniques for preparing polyclonal and monoclonal antibodies as well as hybridomas capable of producing the desired antibody are well known in the art (see Campbell, A. M., *Monoclonal Antibody Technology: Laboratory Techniques in Biochemistry and Molecular Biology*, Elsevier Science Publishers, Amsterdam, The Netherlands (1984); St. Groth, et al., *J Immunol Methods* 35:1–21 (1980)). Any animal (mouse, rabbit, etc.) which is known to produce antibodies can be immunized with the peptide (or an antigenic fragment thereof). Methods for immunization are well known in the art. Such methods include subcutaneous or intraperitoneal injection of the peptide. One skilled in the art will recognize that the amount of the peptide used for immunization will vary based on the animal which is immunized, the antigenicity of the peptide, and the site of injection.

The peptide which is used as an immunogen may be modified or administered in an adjuvant in order to increase the peptide's antigenicity. Methods of increasing the antigenicity of a peptide are well known in the art and include, but are not limited to, coupling the antigen with a heterologous protein (such as a globulin or beta-galactosidase) or through the inclusion of an adjuvant during immunization.

For monoclonal antibodies, spleen cells from the immunized animals are removed, fused with myeloma cells, such as SP2/O-Ag myeloma cells, and allowed to become monoclonal antibody producing hybridoma cells.

Any one of a number of methods well known in the art can be used to identify the hybridoma cell which produces an antibody with the desired characteristics. These include screening the hybridomas with an ELISA assay, western blot analysis, or radioimmunoassay (Lutz, et al., *Exp Cell Res* 175:109–124 (1988)).

Hybridomas secreting the desired antibodies are cloned and the class and subclass are determined using procedures known in the art (Campbell, A. M., *Monoclonal Antibody Technology: Laboratory Techniques in Biochemistry and Molecular Biology*, Elsevier Science Publishers, Amsterdam, The Netherlands (1984)) For polyclonal antibodies, antibody containing antisera is isolated from the immunized animal and is screened for the presence of antibodies with the desired specificity using one of the above-described procedures.

Once a monoclonal antibody which specifically binds to the peptide is identified, the monoclonal can be used to identify peptides capable of mimicking the inhibitory activity of the monoclonal antibody. One such method utilizes the development of epitope libraries and biopanning of bacteriophage libraries. Briefly, attempts to define the binding sites for various monoclonal antibodies have led to the development of epitope libraries. Parmley and Smith developed a bacteriophage expression vector that could display foreign epitopes on its surface (Parmley, S. F. & Smith, G. P., *Gene* 73:305–318 (1988)). This vector could be used to construct large collections of bacteriophage which could include virtually all possible sequences of a short (e.g., six-amino-acid) peptide. They also developed biopanning, which is a method for affinity-purifying phage displaying foreign epitopes using a specific antibody (see Parmley, S. F. & Smith, G. P., *Gene* 73:305–318 (1988); Cwirla, S., *Proc Natl Acad Sci USA* 87:6378–6382 (1990); Scott, J. K. & Smith, G. P., *Science* 249:386–390 (1990); Christian, R. B., et al., *J Mol Biol* 227:711–718 (1992); Smith, G. P. & Scott, J. K., *Methods in Enzymology* 217:228–257 (1993)).

After the development of epitope libraries, Smith et al. then suggested that it should be possible to use the bacteriophage expression vector and biopanning technique of Parmley and Smith to identify epitopes from all possible sequences of a given length. This led to the idea of identifying peptide ligands for antibodies by biopanning epitope libraries, which could then be used in vaccine design, epitope mapping, the identification of genes, and many other applications (Parmley, S. F. & Smith, G. P., *Gene* 73:305–318 (1988); Scott, J. K., *Trends in Biochem Sci* 17:241–245 (1992)).

Using epitope libraries and biopanning, researchers searching for epitope sequences found instead peptide sequences which mimicked the epitope, i.e., sequences which did not identify a continuous linear native sequence or necessarily occur at all within a natural protein sequence. These mimicking peptides are called mimotopes. In this manner, mimotopes of various binding sites/proteins have been found.

The sequences of these mimotopes, by definition, do not identify a continuous linear native sequence or necessarily occur in any way in a naturally-occurring molecule, i.e., a naturally occurring protein. The sequences of the mimotopes merely form a peptide which functionally mimics a binding site on a naturally-occurring protein.

Many of these mimotopes are short peptides. The availability of short peptides which can be readily synthesized in large amounts and which can mimic naturally-occurring sequences (i.e., binding sites) offers great potential application.

Using this technique, mimotopes to a monoclonal antibody that recognizes the peptide of the subject invention can be identified. Once the sequence of the mimotope is determined, the peptide drugs can be chemically synthesized.

The targeting moiety peptides can contain any naturally-occurring or non-naturally-occurring amino acids, including the D-form of the amino acids, amino acid derivatives and amino acid mimics, so long as the desired function and activity of the peptide is maintained. The choice of including an (L)- or a (D)-amino acid in the peptide depends, in part, on the desired characteristics of the peptide. For example, the incorporation of one or more (D)-amino acids can confer increased stability on a peptide and can allow a peptide to remain active in the body for an extended period of time. The incorporation of one or more (D)-amino acids can also increase or decrease the pharmacological activity of a peptide.

The peptide may also be cyclized, since cyclization may provide the peptide with superior properties over their linear counterparts. Cyclization is discussed further below.

Modifications to the peptide backbone and peptide bonds thereof can be made to the amino acid, derivative thereof, non-amino acid moiety or the peptide either before or after the amino acid, derivative thereof or non-amino acid moiety is incorporated into the peptide. What is critical is that such modifications mimic the peptide backbone and bonds which make up the same and have substantially the same spatial arrangement and distance as is typical for traditional peptide bonds and backbones. An example of one such modification is the reduction of the carbonyl(s) of the amide peptide backbone to an amine. A number of reagents are available and well known for the reduction of amides to amines such as those disclosed in Wann et al., *JOC* 46:257 (1981) and Raucher et al., Tetrahedron Lett 21:14061 (1980). An amino acid mimic is, therefore, an organic molecule that retains the similar amino acid pharmacophore groups as are present in the corresponding amino acid and which exhibits substantially the same spatial arrangement between functional groups. For example, in evaluating a series of analogs for the nonapeptide (EMTOVNOGQ; SEQ ID NO:5) using an estrogen-dependent uterine growth inhibition assay, the pharmacophore of the peptide was preferably found to include side chains of V and N, and backbone atoms contributed by T, O, V, N, O, and G. However, as previously discussed, conservative substitutions can be made at these positions without losing full activity.

One skilled in the art, using the identified sequences can easily synthesize the peptides for use in the invention.

Standard procedures for preparing synthetic peptides are well known in the art. The novel peptides can be synthesized using, e.g., the solid phase peptide synthesis (sPPS) method of Merrifield, *J Am Chem Soc* 85:2149 (1964) or modifications of SPPS; or, the peptides can be synthesized using standard solution methods well known in the art (see, for example, Bodanzsky, *Principles of Peptide Synthesis*, 2d Ed., Springer-Verlag (1993)). Alternatively, simultaneous multiple peptide synthesis (SMPS) techniques well known in the art can be used. Peptides prepared by the method of Merrifield can be synthesized using an automated peptide synthesizer such as the Applied Biosystems 431A-01 Peptide Synthesizer (Mountain View, Calif.) or using the manual peptide synthesis technique described by Houghten, *Proc Natl Acad Sci USA* 82:5131 (1985)

In certain embodiments of the modulator compounds of the invention, an amino acid peptidic structure is coupled directly or indirectly to at least one modifying group (abbreviated as MG). "Modifying group" includes structures that are directly attached to the amino acid peptidic structure (e.g., by covalent coupling), as well as those that are indirectly attached to the peptidic structure (e.g., by a stable non-covalent association or by covalent coupling to additional amino acid structures, or mimetics, analogs or derivatives thereof, which may flank the amino acid peptidic structure). For example, the modifying group can be coupled to the amino-terminus or carboxy-terminus of an amino acid peptidic structure, or to a peptidic or peptidomimetic region flanking the core domain. Alternatively, the modifying group can be coupled to a side chain of at least one amino acid structure of an amino acid peptidic structure, or to a peptidic or peptidomimetic region flanking the core domain, through a hydroxy group of a tyrosyl structure(s), a serine structure(s) or a threonine structure(s) or other suitable reactive group on an amino acid side chain). Modifying groups covalently coupled to the amino acid peptidic structure can be attached by means and using methods well known in the art for linking chemical structures, including, for example, amide, alkylamino, carbamate, urea or ester bonds. The modifying group may be used to link the targeting moiety peptide with a metal ion binding domain and/or other labeliing moiety.

The term "modifying group" is intended to include groups that are not naturally coupled to natural peptides in their native form. Accordingly, the term "modifying group" is not intended to include hydrogen. The modifying group(s) is selected such that the modulator compound alters, and preferably inhibits, cell proliferation when contacted with the peptides.

The modifying group(s) may include a cyclic, heterocyclic, polycyclic or branched alkyl group. "Cyclic group" includes cyclic saturated or unsaturated (i.e., aromatic) group having from about 3 to 10, preferably about 4 to 8, and more preferably about 5 to 7, carbon atoms. Exemplary cyclic groups include cyclopropyl, cyclobutyl, cyclopentyl, cyclohexyl, and cyclooctyl. Cyclic groups may be unsubstituted or substituted at one or more ring positions. Thus, a cyclic group may be substituted with, e.g., halogens, alkyls, cycloalkyls, alkenyls, alkynyls, aryls, heterocycles, hydroxyls, aminos, nitros, thiols amines, imines, amides, phosphonates, phosphines, carbonyls, carboxyls, silyls, ethers, thioethers, sulfonyls, sulfonates, selenoethers, ketones, aldehydes, esters, —$CF_3$, —CN, or the like.

"Heterocyclic group" includes cyclic saturated or unsaturated (i.e., aromatic) groups having from about 3 to 10, preferably about 4 to 8, and more preferably about 5 to 7, carbon atoms, wherein the ring structure includes about one to four heteroatoms. Heterocyclic groups include pyrrolidine, oxolane, thiolane, imidazole, oxazole, piperidine, piperazine, morpholine and pyridine. The heterocyclic ring can be substituted at one or more positions with such substituents as, for example, halogens, alkyls, cycloalkyls, alkenyls, alkynyls, aryls, other heterocycles, hydroxyl, amino, nitro, thiol, amines, imines, amides, phosphonates, phosphines, carbonyls, carboxyls, silyls, ethers, thioethers, sulfonyls, selenoethers, ketones, aldehydes, esters, —$CF_3$, —CN, or the like. Heterocycles may also be bridged or fused to other cyclic groups as described below.

"Polycyclic group" includes two or more saturated or unsaturated (i.e., aromatic) cyclic rings in which two or more carbons are common to two adjoining rings, e.g., the rings are "fused rings". Rings that are joined through non-adjacent atoms are termed "bridged" rings. Each of the rings of the polycyclic group can be substituted with such substituents as described above, as for example, halogens, alkyls, cycloalkyls, alkenyls, alkynyls, hydroxyl, amino, nitro, thiol, amines, imines, amides, phosphonates, phosphines, carbonyls, carboxyls, silyls, ethers, thioethers, sulfonyls, selenoethers, ketones, aldehydes, esters, —$CF_3$, —CN, or the like.

In addition to the cyclic, heterocyclic and polycyclic groups discussed above, other types of modifying groups can be used in a modulator of the invention. For example, hydrophobic groups and branched alkyl groups may be suitable modifying groups. Examples include acetyl groups, phenylacetyl groups, phenylacetyl groups, diphenylacetyl groups, triphenylacetyl groups, isobutanoyl groups, 4-methylvaleryl groups, trans-cinnamoyl groups, butanoyl groups and 1-adamantanecarbonyl groups.

Modifying groups include cis-decalin-containing groups, biotin-containing groups, fluorescein-containing groups, a diethylene-triaminepentaacetyl group, a (−)-menthoxyacetyl group, an N-acetylneuraminyl group, a phenylacetyl group, a diphenylacetyl group, a triphenylacetyl group, an isobutanoyl group, a 4-methylvaleryl group, a 3-hydroxyphenylacetyl group, a 2-hydroxyphenylacetyl group, a 3,5-dihydroxy-2-naphthoyl group, a 3,4-dihydroxycinnamoyl group, a (±)-mandelyl group, a (±)-mandelyl-(±)-mandelyl group, a glycolyl group, a benzoylpropanoyl group and a 2,4-dihydroxybenzoyl group.

"Pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions. For human administration, preparations should meet sterility, pyrogenicity, general safety and purity standards as required by FDA Office of Biologics standards.

An agent of the invention can be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Materials and Methods

Cell Lines. T47D and MDA-231 human breast cancer cell lines were purchased from the American Type Culture Collection (Manassas, Va.). Growth medium for T47D cells consisted of RPMI 1640 (Life Technologies, Germantown, Md.) supplemented with 10% fetal bovine serum (Life Technologies) and 8 µg/ml bovine insulin (Sigma, St. Louis, Mo.). Growth medium for MDA-MB-231 consisted of Dulbecco's Modified Eagle Medium (Life Technologies) supplemented with L-glutamine (2 mM), non-essential amino acids (1%, Life Technologies) and bovine insulin (1 µg/ml). The MCF-7 cell line was obtained from Dr. Alberto C. Baldi, Institute of Experimental Biology and Medicine, Buenos Aires, Argentina, and was maintained as previously described by Gierthy et al. (1991). This strain of MCF-7 demonstrated 17β-estradiol ($E_2$) sensitivity in regard to induction of tissue plasminogen activator, cell proliferation and in vivo tumor growth and was sensitive to the suppression of these effects by tamoxifen. Continuous exposure of these cells to 1 µM tamoxifen citrate during routine culture conditions (1:10-subculture ratio once a week) resulted after 6 months in a strain that was resistant to the suppressive effects of tamoxifen in vitro.

Peptide Synthesis. Peptides were synthesized using FMOC solid phase peptide synthesis on a Pioneer Peptide Synthesis System (PerSeptive Biosystems, Inc., Framingham, Mass.) (see also Mesfin et al. 2000). Briefly, peptides were assembled on a solid support (FMOC-Polyethylene-Graft Polystyrene Support) from the C-terminus, reacting the deblocked amino (N)-terminus of support-bound amino acid with the activated carboxyl (C)-terminus of the incoming amino acid to form an amide bond. Amino acids used in the synthesis had their N-amino group protected by the 9 fluorenylmethoxycarbonyl (FMOC) group, which was removed by piperidine at the end of each cycle in the synthesis. Side-chain protecting groups of amino acids were Asn(Trt), Gln(Trt), Glu(OtBu), Hyp(tBu), Thr(tBu) which were deprotected by trifluoroacetic acid (TFA) after peptide synthesis. The carboxyl-group of the amino acid was activated with HATU [o-(7-azabenzotriazol-1-yl)-1,1,3,3-tetramethyluronium hexafluorophosphate] obtained from PerSeptive Biosystems Inc. The specific amino acid derivatives, supports, and reagents used in the synthesis were purchased from PerSeptive Biosystems Inc. and Nova Biochem, San Diego, Calif.

After synthesis was completed, the resin was washed 20 three times with 100% propanol and the cleavage reaction was achieved by incubating the resin in 10 ml trifluoracetic acid/thioanisole/anisole/1,2-ethanedithiol (90:5:2:3) per 0.5 g resin for 5 hours. The cleavage reaction mixture was filtered using a sintered glass funnel to separate the solid resin from the peptide solution. Filtrate volume was reduced to 1 ml by evaporation facilitated with a gentle stream of air and the peptides were precipitated by addition of 15 ml dry-ice chilled ethyl ether. The peptides were allowed to settle for five minutes at −80° C., and the supernatant was aspirated. The peptides were then washed twice in similar manner with 15 ml of ethyl ether. After three further washings with 15 ml of ethyl acetate:diethylether (1.5:1, room temperature), the peptides were dissolved in deionized water, purified by reverse phase HPLC (see details below), lyophilized, and stored at −20° C.

Cyclization of the Peptides. Cyclization of peptides was accomplished using methods described by Kates et al. (17, 18). Briefly, N-alpha FMOC-L-glutamic acid-alpha-allyl ester at the C-terminus of the synthetic peptide was coupled to the resin via the γ-carboxylic acid. Removal of the Nα-FMOC allowed the remaining amino acids to be incorporated sequentially into the growing peptide. A free alpha-carboxyl group was then generated upon removal of the allyl group from the C-terminal Glu (18). This alpha-carboxyl group was then coupled to the free N-terminal structure of the peptide (while on the resin) in order to generate the cyclic peptide, which was then removed from the resin in such a way as to yield the γ-carboxamido derivative (i.e., Q). The cyclic peptide was then purified and characterized as described below.

Purification of Peptides. Purification of peptides was accomplished using a Waters Delta-Pak $C_{18}$ (19 mm×30 cm) reverse phase column with a pore diameter of 300 Å on a Waters 650E liquid chromatography system equipped with a 486 adjustable absorbance detector and a 600E controller. The column was operated with gradient using 0.1% trifluoroacetic acid in water as solvent A and 0.1% trifluoroacetic acid in acetonitrile as solvent B. The gradient was set as follows: 100% solvent A for the first 4 min, followed by increasing acetonitrile from 0–40% solvent B over the next 35 min, then isocratically at 40% B for 11 min, and followed by a linear gradient of 40–30 100% B over 10 min, all with a flow rate of 7 ml/min. Peptide was monitored at 230 nm and fractions containing pure peptide (>95% purity) were pooled together and lyophilized.

Peptide Characterization. Amino acid analyses of all peptides were performed using the Waters AccQ-Tag amino acid analysis system (19; 20). Peptides were analyzed by mass spectrometry using standard α-cyano-4-hydroxysinnipinic acid and sinnipinic acid matrices. Integrity of cyclized peptides was further validated using the Kaiser test (21~to ensure absence of free terminal amino group.

Immature Mouse Uterine Growth Assay. A bioassay for anti-estrotrophic activity was performed using an immature mouse uterine growth assay (22). Swiss/Webster female mice, 6–8 g in body weight (13–15 days old), were obtained from Taconic Farms (Germantown, N.Y.). Mice were weighed and distributed into treatment groups (typically 5 mice per group) such that each group contained the same range of body weight. In a typical experiment, each group received two sequential intraperitoneal injections spaced one hour apart. Test material or vehicle control for that material was contained in the first injectant. Estradiol ($E_2$) or vehicle control for $E_2$ was contained in the second injectant. Twenty-two hours after the second injection, uteri were dissected, trimmed free of mesenteries, and immediately weighed. The uterine weights were normalized to mouse body weights (mg uterine weight/g of body weight) to compensate for differences in body weight among litters of the same age. Experiments employed a minimum of five mice per group, and the mean normalized uterine weight±standard error for each group was calculated. Percent growth inhibition in a test group was calculated from the normalized uterine wet weights as described below.

Growth Inhibition (%)=Full $E_2$-Stimulation in Test Group×100% Full $E_2$-Stimulation−No $E_2$-Stimulation Differences between groups were evaluated, employing the non-parametric Wilcoxon Sum of Ranks test (one-sided). In all cases, growth inhibitions that were greater than 25% were significant at p≦0.05.

Human Breast Cancer Xenograft Assay. A bioassay for anti-breast cancer activity was performed according to Bennett et al. (23;24). Confluent MCF-7 human breast cancer cells were trypsinized into suspension and pelleted by centrifugation at 200×g. The pellet was then solidified into a fibrin clot by exposing it to 10 μl of fibrinogen (50 mg/ml) and 10 μl of thrombin (50 units/ml). The solid mass of MCF-7 cells was then cut into pieces 1.5 mm in diameter. A tumor segment of ~1.5 mm in diameter was implanted under the kidney capsule of an immunodeficient ICR-SCID male mouse (Taconic Farms) that weighed about 25 g. Estrogen supplementation was accomplished by s.c. implantation of a silastic tubing capsule containing solid $E_2$ inserted on the day of tumor implantation. Peptide was injected i.p. every twelve hours at a dose of 1 μg per mouse. Tumor growth was monitored during survival laparotomy at 10 day intervals by measurement of the diameters of the short (d) and long axes (D) of each tumor, using a dissecting microscope equipped with an ocular micrometer. Tumor volumes were calculated using the formula $(\pi/6)(d)^2 D$, assuming the tumor shape to be an ellipsoid of revolution around its long axis (D). There were five to seven replicate mice included in each treatment group. Mean tumor volume±standard error in each group was calculated for display of growth curves. Significance of differences between groups was tested using the one-sided Wilcoxon Sum of Ranks Test.

Assessment of Estrogen Receptor Antagonism. Commercially obtained rabbit uteri (Pel-Freez Biological, Rogers, Ark.) were used as a source of estrogen receptor. Uteri were pulverized in a stainless steel impact mortar under liquid nitrogen and homogenized (20% w/v) in assay buffer (10 mM Tris (pH 7.4), 1.5 mM EDTA, 10% glycerol, 10 mM monothioglycerol, arid 10 mM sodium molybdate] on ice. Centrifugation (50,000×g) for 1 h yielded a supernatant containing cytosol, which was adjusted with assay buffer to 2.5 mg protein/ml. All incubations were carried out in triplicate, each containing 100 μl of cytosol, 20 μl of 10 mM 6,7-[3H]estradiol (50 Ci/mmol; DuPont Pharmaceuticals Company, Wilmington, Del., U.S.A.), and 80 μl of putative antagonist in assay buffer. Total count tubes received 20 μl of [3H]estradiol and 180 μl of assay buffer. After incubation overnight at 4° C., all but the total count tubes received 300 μl of dextran-coated charcoal suspension; tubes were agitated for 15 min and then centrifuged (1,000×g) for 15 min. Supernatants were decanted into counting vials, scintillant was added, and protein-bound tritium was determined by liquid scintillation counting.

EXAMPLE I

Development of a Synthetic Cyclized Peptide Derived from Alpha-Fetoprotein.

Figure 1B:
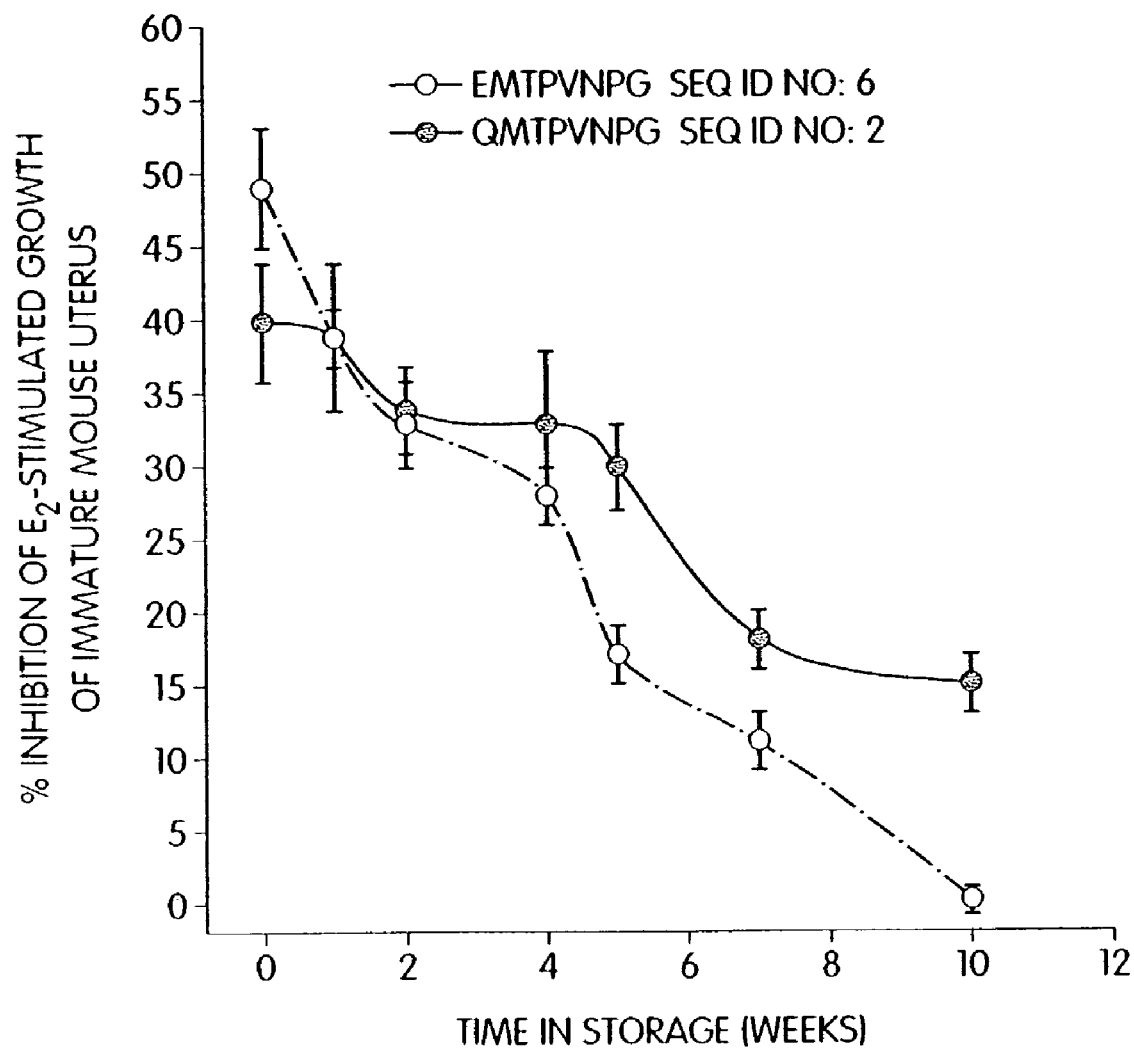

Earlier, it had been shown that an energy-minimized structure of octapeptide SEQ ID NO:6, EMTPVNPG indicated that the peptide had potential to form a horseshoe shaped structure (Mesfin et al. 2000). Energy-minimization studies of an analog of this peptide, that would be generated by substitution of the N-terminal glutamic acid with glutamine (SEQ ID NO:2, QMTPVNPG), indicated that this product would have potential to bow even further inward and form a pseudo-cyclic structure. This pseudo-cyclic structure may have greater structural stability due to hydrogen bonding between the N-terminal glutamine γ-carboxamide group and the C-terminal glycine α-carboxamide. This linear analog (SEQ ID NO:2, QMTPVNPG) was therefore synthesized, and its biological activity was compared to SEQ ID NO:6, EMTPVNPG, in the estrogen-dependent immature mouse uterine growth assay. SEQ ID NO:2, QMTPVNPG inhibited the estrogen-stimulated growth of mouse uterus with an optimal dose of 1 μg/mouse (FIG. 1a), similar to the native octapeptide SEQ ID NO:6, EMT-PVNPG. These results suggested that the substitution of glutamic acid to glutamine did not-detract from the biological activity and also did not change the biphasic nature of the dose-response curve. Shelf-life studies indicated that SEQ ID NO:2, QMTPVNPG stored somewhat better than the native octapeptide (SEQ ID NO:6, EMTPVNPG), but its anti-estrotrophic activity also diminished to insignificant levels after five weeks of storage (FIG. 1b), indicating that the putative stabilization was not sufficient to prevent loss of biological activity during storage.

As shown in Table I, aged octapeptide SEQ ID NO:2, QMTPVNPG, stored in the lyophilized state at −20° C. for over one year, was completely biologically inactive. However, brief treatment with 4M urea restored its biological activity, suggesting that this peptide might have aggregated during storage, resulting in loss of biological activity. A scrambled form of the Q octapeptide had no biological activity either with or without urea treatment. The biological activity of stored inactive SEQ ID NO:6, EMTPVNPG was likewise regenerated by 4M urea.

Figure 2A:
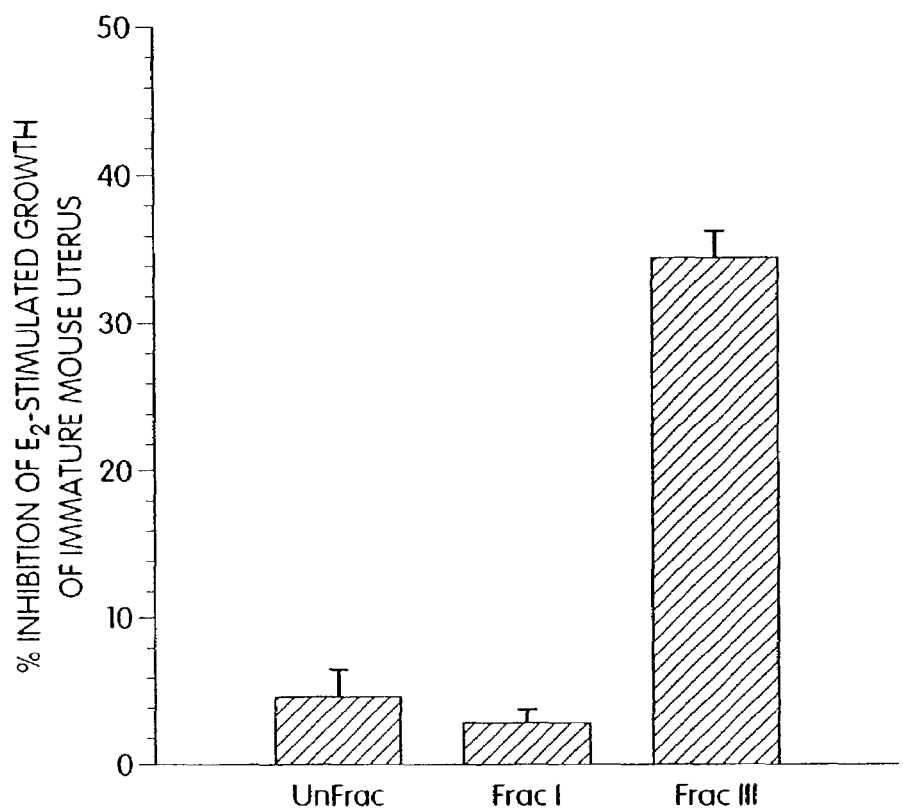
FIGS. 2a and 2b illustrate the anti-uterotrophic activity of fractions from gel-filtration chromatography of stored octapeptide, SEQ ID NO:2, QMTPVNPG. The octapeptide was fractionated using a Waters SW 200 gel-filtration column using phosphate buffered saline pH 7.4 as the mobile phase. Fractions which had significant UV absorbance at 230 nm were collected at twenty second intervals. The first fraction (Frac I), the last fraction (Frac III), and the starting material (UnFrac) were all tested in the immature mouse uterine growth assay as described in FIGS. 1a and 1b. 1 μg of peptide was injected i.p. into mice in all cases, and 20 percent inhibition of $E_2$-stimulated growth was measured.
Figure 2B:
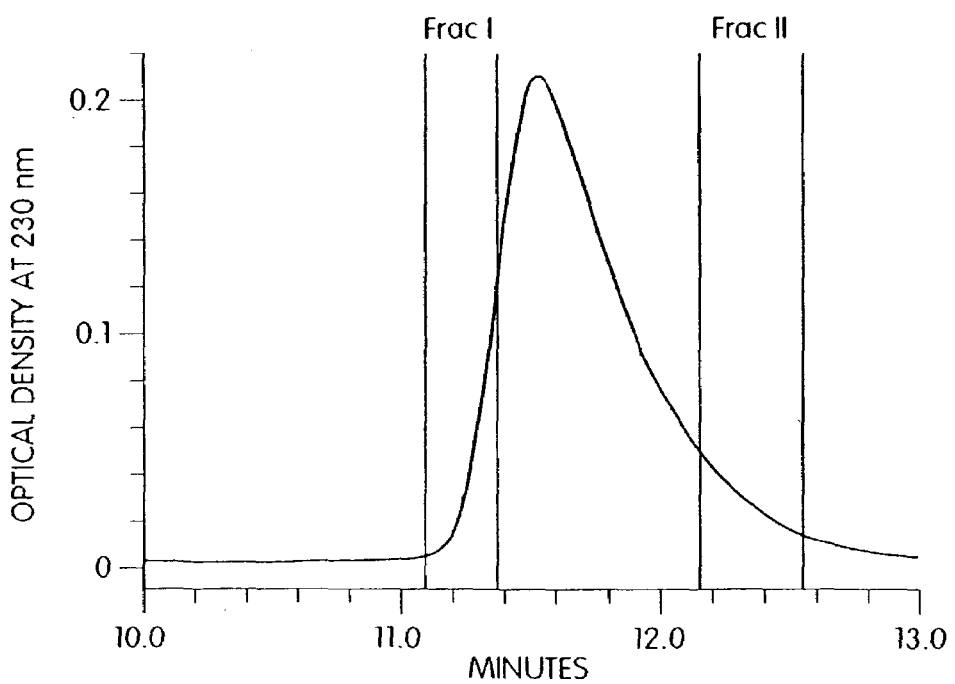

Gel filtration column chromatography of aged peptide (SEQ ID NO:2, QMTPVNPG) yielded a single peak (FIG. 2b) which became broader as a function of time in storage. This suggested that small aggregates (dimers, trimers) were forming during storage. Although gel filtration chromatography has low resolution for monomers, dimers, and trimers in this size range (841 Da to 2523 Da), the width of the peak suggested that aggregates might be separating from monomer. Fractions from different portions of the broad peak from aged, chromatographed peptide were therefore tested for biological activity. The higher molecular weight fraction (FIG. 2b, left side of peak) was biologically inactive while the lower molecular weight fraction (FIG. 2b, right side of peak) was active in the estrogen-dependent immature mouse uterine growth assay. This suggested that the octapeptide SEQ ID NO:2, QMTPVNPG, like its parent protein and precursor 34-mer peptide (Wu et al. 1985; Eisele et al. 2001), aggregated during prolonged storage in the lyophilized state and only partially dissociated during chromatography, and that the monomeric form of the peptide was the active species. While not especially hydrophobic, the peptide does carry a net charge of only +1 at neutral pH, and taken together with the chromatography and urea evidence, it is reasonable to conclude that hydrophobicity played a role in its aggregation.

In addition to aggregation, small peptides such as octapeptide SEQ ID NO: 6, EMTPVNPG or SEQ ID NO:2, QMTPVNPG have structural flexibility that allows them to attain a variety of different structural conformations. Since it was thought unlikely that all structural conformers of octapeptide SEQ ID NO:6, EMTPVNPG or SEQ ID NO: 2, QMTPVNPG would be biologically active, it seemed appropriate to employ the strategy of conformational constraint in an effort to produce stable analogs. Therefore, cyclic analogs were generated to limit the activity. This greatly expands the active dose range and increases the probability of maintaining an effective dose in humans.

The finding that both linear and cyclized peptides completely stopped the growth of human MCF-7 breast cancer xenografts is highly significant and certainly demonstrates the relevance of these peptides to breast cancer therapeutics. The magnitude of their inhibitory effect was similar to that of tamoxifen which was also shown to stop MCF-7 breast cancer xenograft growth in an earlier study (Bennett et al. 1998). However, their mechanism of action seems to be different from that of tamoxifen, in that they do not interfere with estrogen binding to its receptor. This opens the possibility of combining these agents with tamoxifen or using them in place of tamoxifen when, as so often happens, an estrogen receptor positive breast cancer becomes resistant to tamoxifen (Howell et al. 1995).

EXAMPLE II

Prevention of Growth of Estrogen-Dependent Human Breast Cancers Sensitive and Resistant to Tamoxifen An 8-mer peptide (SEQ ID NO: 4, EMTOVNOG) derived from alpha-fetoprotein (AFP) was compared to tamoxifen for activity against growth of human breast cancer xenografts implanted in immune-deficient mice. Both peptide and tamoxifen prevented growth of estrogen receptor-positive MCF-7 and T47D human breast cancer xenografts. A subline of MCF-7, made resistant to tamoxifen by a six-month exposure to this drug in culture, was found to be resistant to tamoxifen in vivo. Peptide completely prevented the xenograft growth of this tamoxifen-resistant subline of MCF-7. Neither peptide nor tamoxifen were effective in slowing the xenograft growth of the estrogen-receptor-negative MDA-M2-231 human breast cancer. A worrisome toxicity of tamoxifen is its hypertrophic effect on the uterus. In this study, tamoxifen was shown to stimulate the growth of the immature mouse uterus in vivo, and the peptide significantly inhibited tamoxifen's uterotrophic effect. The mechanism of action of peptide is different from that of tamoxifen in that the peptide does not interfere with the binding of [$^3$H]estradiol to the estrogen receptor. In conclusion, AFP-derived peptide appears to be a novel agent that interferes with the growth of tamoxifen-sensitive as well as tamoxifen-resistant estrogen receptor-positive human breast cancers; it inhibits the uterotrophic side effect of tamoxifen; and thus it can be used in combination with or in place of tamoxifen for treatment of estrogen receptor-positive human breast cancers.

Figure 9A:
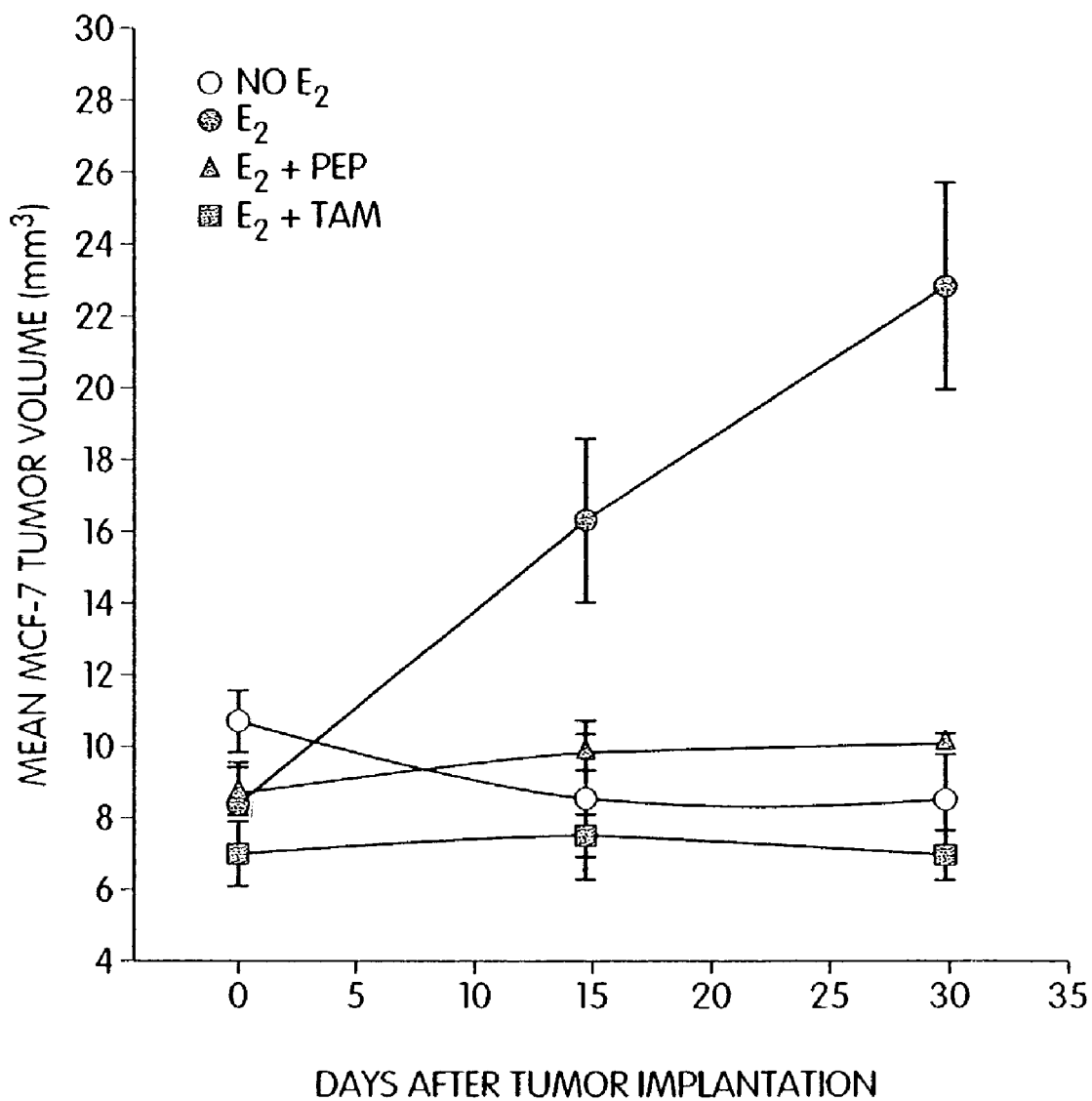
FIGS. 9a and 9b illustrate the effect of AFP-derived peptide on growth of estrogen-receptor-positive MCF-7 and MCF-7/Tam human breast cancer xenografts. Tumors were implanted as described in Materials and Methods. Estrogen (●) was provided via a slow-release pellet of estradiol ($E_2$) implanted s.c. Peptide (▲) was given twice a day i.p. at a dose of 1 µg per injection. Tamoxifen (■) was given once a day i.p. at a dose of 50 µg per mouse. Tumor volumes in each mouse were measured at the time of tumor implantation, again at day 15 after tumor implantation during survival laparotomy and again at day 30 after tumor implantation during necropsy. There was a minimum of 5 mice per group.
Figure 9B:
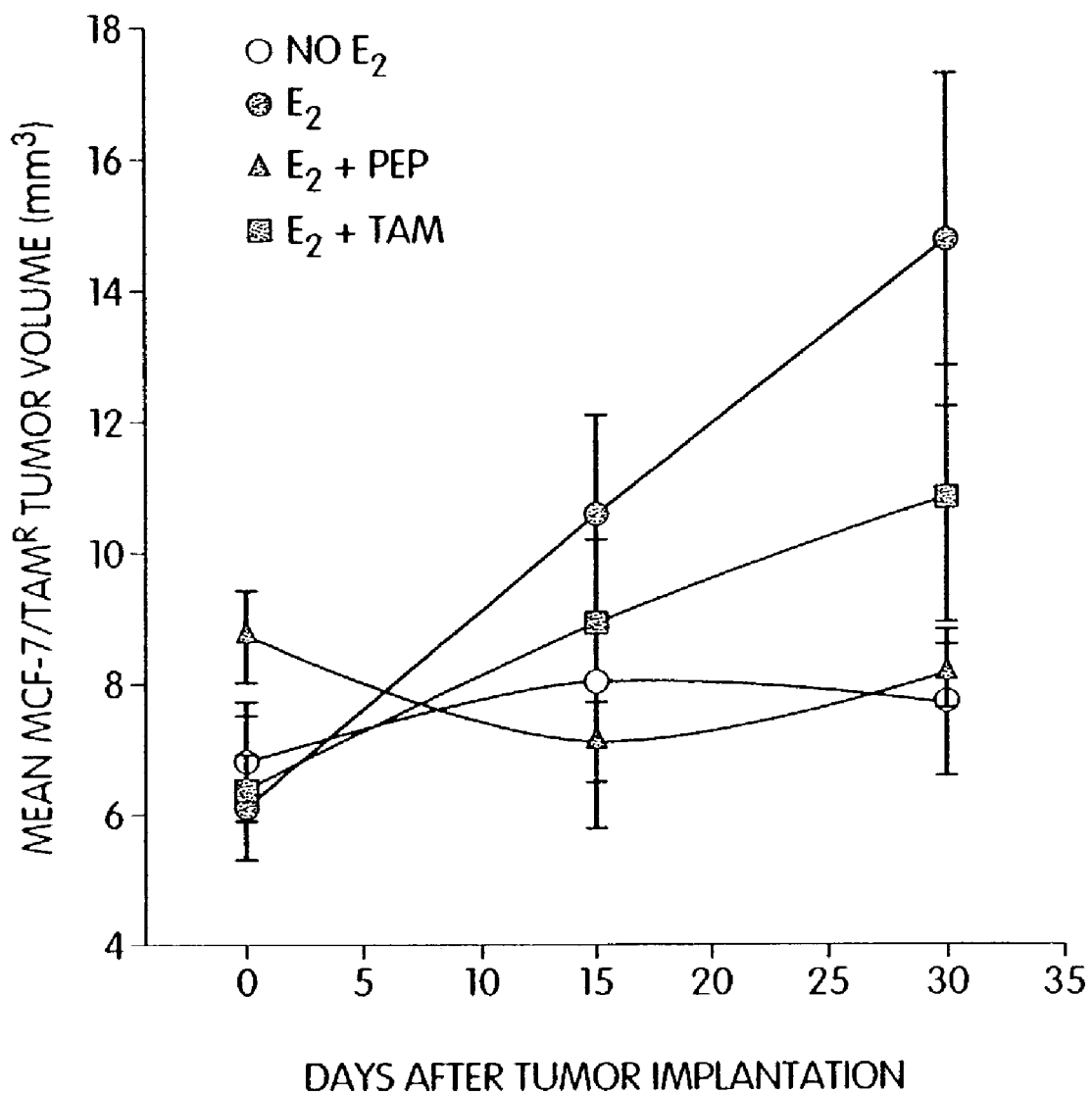
Figure 10:
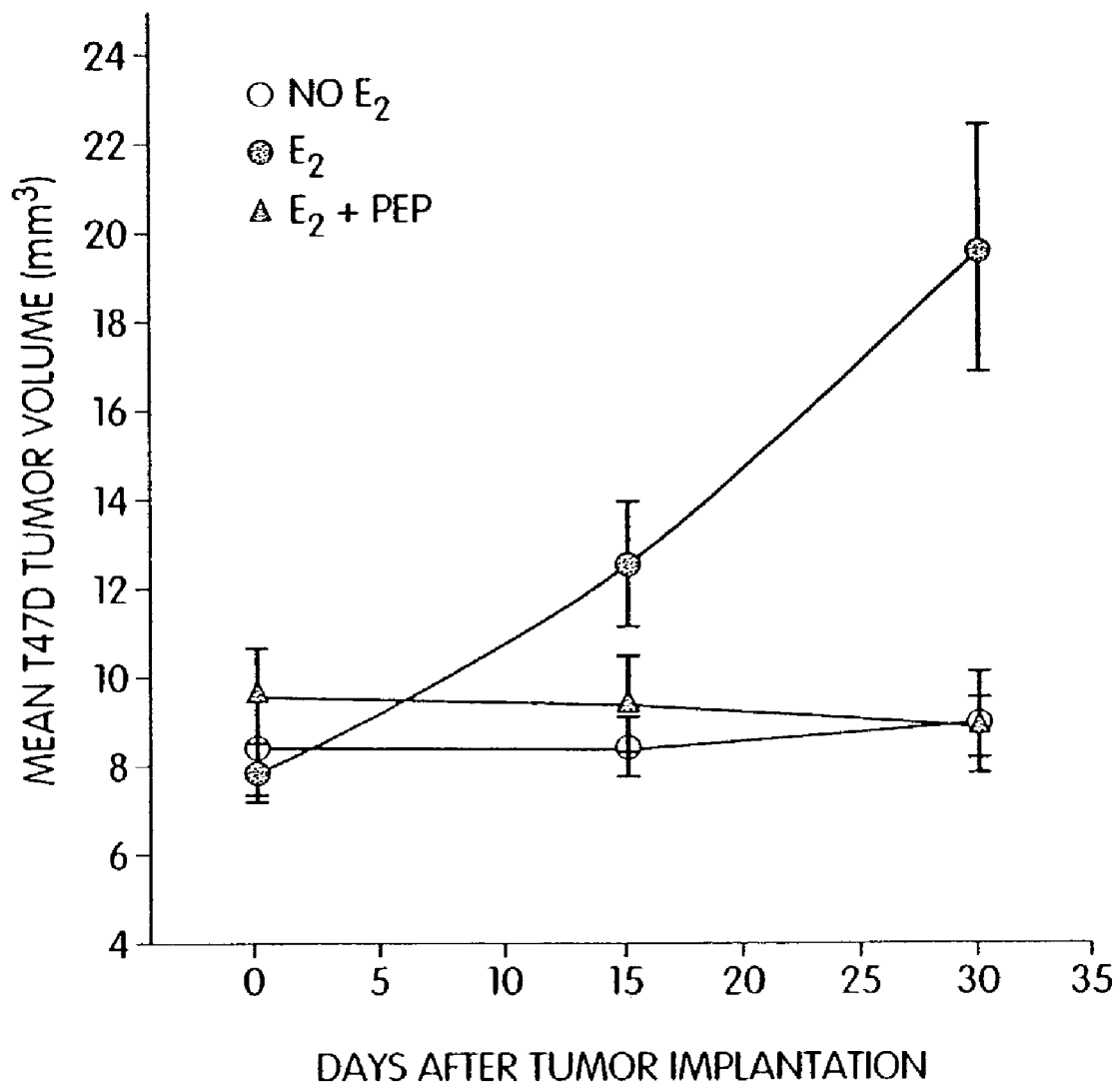
FIG. 10 illustrates the effect of AFP-derived peptide on growth of estrogen-receptor-positive T47D human breast cancer xenografts. See the legend to FIGS. 9a and 9b for the experimental protocol. At day 30 after tumor implantation, tumor volumes in the $E_2$+Pep group were significantly different from tumor volumes in the $E_2$ alone 25 group, $p<0.05$, Wilcoxon Ranks Sum Test.

It was determined in a screening assay of the inhibition of $E_2$-stimulated growth of immature mouse uterus by AFP-derived peptide that an effective anti-estrotrophic dose of SEQ ID NO: 4, EMTOVNOG was 0.1 µg to 1.0 µg per mouse. Also, preliminary pharmacokinetic studies suggested that the biological half-life of this peptide in these mice was two to three hours. Therefore, for the breast cancer xenograft studies, it was deemed reasonable to administer this peptide twice a day at a dose of 1.0 µg per i.p. injection into tumor-bearing SCID mice. The ER+MCF-7 human breast cancer was used as a first step in evaluating the effectiveness of this peptide against human breast cancer. As shown in FIG. 9a, MCF-7 xenografts were completely dependent on estrogen for growth in SCID mice. They underwent an approximate threefold increase in tumor volume in the presence of a slow-release $E_2$ implant during the 30-day observation. Without $E_2$ supplementation, there was no tumor growth. When $E_2$-supplemented mice were given twice-daily injections of 1 µg of peptide, there was no significant increase in tumor volume over the 30-day observation period. Similarly, when $E_2$-supplemented tumors were given once-daily injections of 50 µg of tamoxifen, there was no increase in tumor volume. When a subline of MCF-7 that had been made resistant to tamoxifen in cell culture was used, a rather provocative outcome was obtained. Xenografts of this subline were still completely dependent on B7 for growth (FIG. 9b). With $E_2$ supplemen tation, they grew somewhat slower than the parent line, approximately doubling in tumor volume over the 30-day observation period. Interestingly, tamoxifen was only minimally effective in retarding the growth of this subline, such that at day 30 after tumor implantation, the tumor volume in the $E_2$ plus tamoxifen group was not significantly smaller than that found in the group receiving $E_2$ only (FIG. 9b). In contrast, peptide completely stopped the growth of this tamoxifen-resistant NCF-7 subline. The peptide was also tested on ER+T47D human breast cancer. Like the MCF-7, T47D xenografts were completely dependent on $E_2$ supplementation for growth (FIG. 10) and more than doubled in tumor volume over the 30-day observation period. Daily treatment with peptide during this time interval completely prevented tumor growth (FIG. 10). An ER-human breast cancer, MDA-MB-231, was then tested for sensitivity to peptide. This tumor grew independent of estrogen supplementation and demonstrated a rather aggressive growth rate during the second two weeks of the observation period (FIG. 11). Daily treatment with peptide had no effect on the growth of this tumor at any time during the 30 day observation period (FIG. 11). Similarly, tamoxifen did not affect the growth of this ER-tumor.

Figure 12:
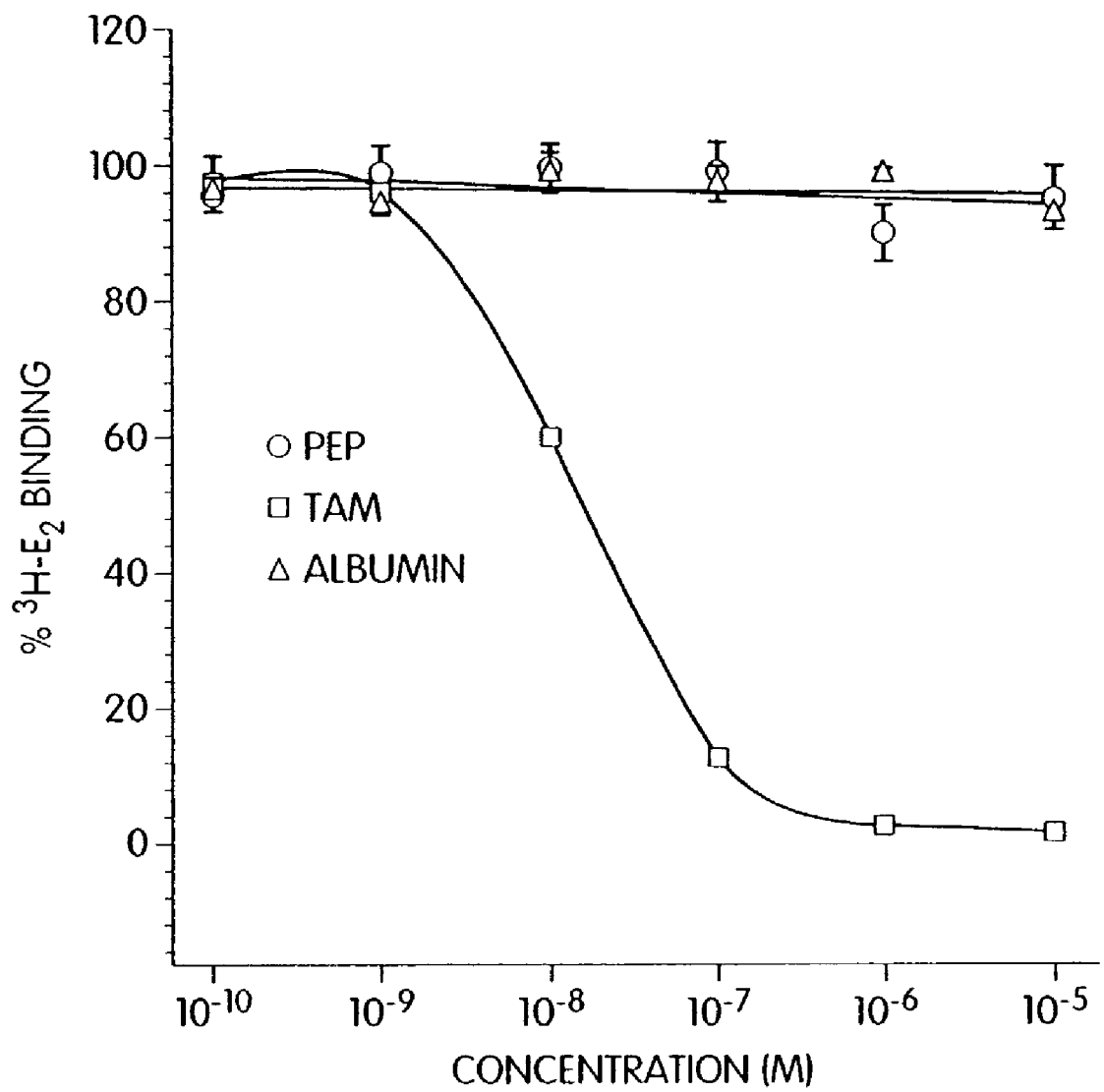
FIG. 12 illustrates the effect of AFP-derived peptide on binding of $E_2$ to its receptor. Rabbit uterine cytosol was used as a source of estrogen receptor. All incubations were performed in triplicate, each containing 100 µl of cytosol, 20 µl of 10 nM 6,7-$^3$H estradiol (50 Ci/mmol), and 80 µl of test agent at the final concentrations indicated on the abscissa. Concentration of [$^3$H]$E_2$-complex with receptor in the presence of different concentrations of test agent is expressed as a percentage of the amount of complex formed in the absence of test agent.

It appears that peptide interferes with E-dependent, but not E-independent, breast cancer growth. As a first step in evaluating the mechanism of action of this peptide, it was compared to tamoxifen as a competitor of $E_2$ for binding to ER. As shown in FIG. 12, tamoxifen exhibits its well documented interference with $E_2$ binding to ER. The $IC_{50}$ and $IC_{100}$ for tamoxifen were $5 \times 10^{-8}$M and $5 \times 10^{-7}$M, respectively. In contrast, peptide produced no interference with $E_2$ binding to ER over a peptide concentration range of $10^{-10}$M to $10^{-5}$M. Thus the mechanism by which peptide interferes with response to estrogen is clearly different from that of tamoxifen.

Figure 13A:
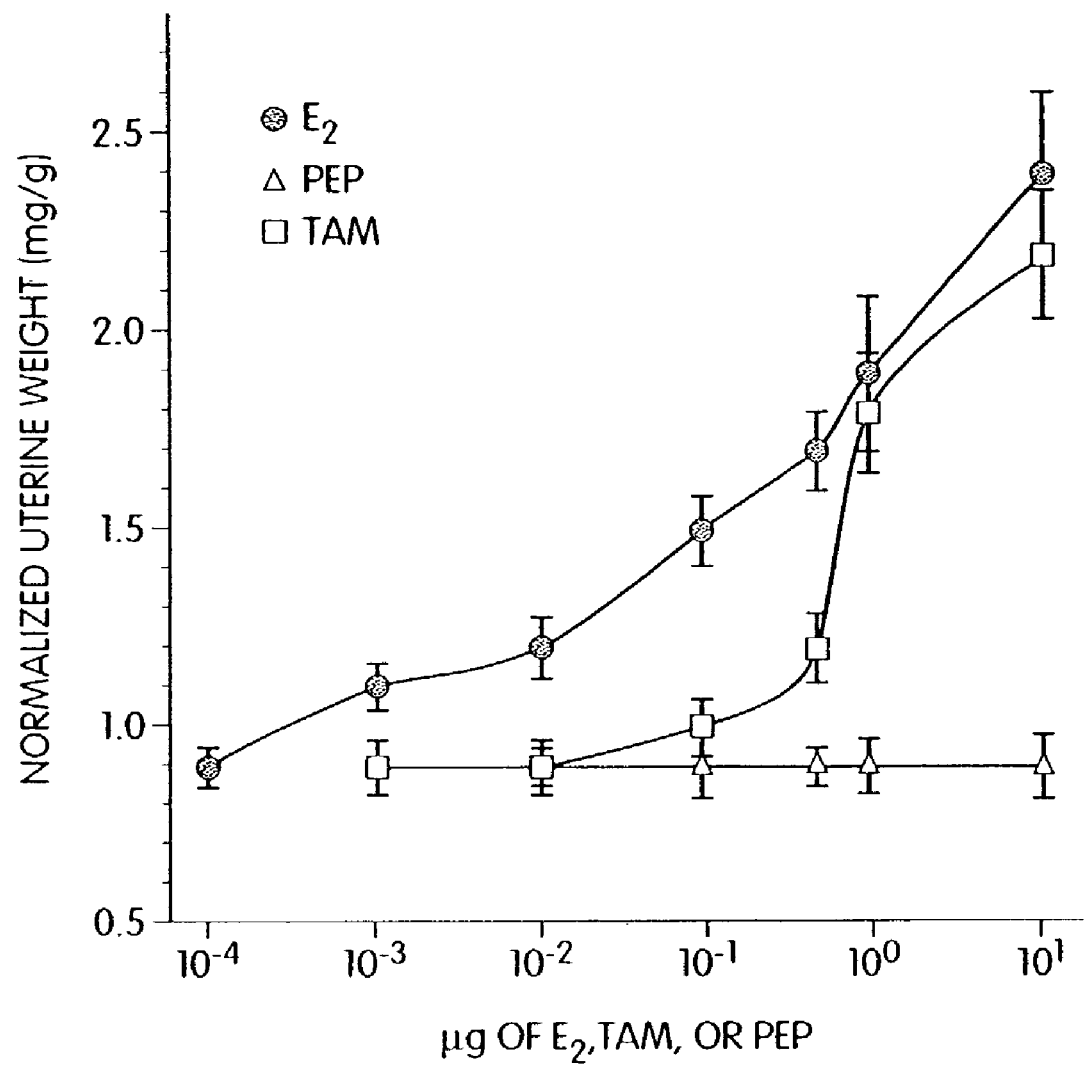
FIG. 13a shows the effect of estradiol ($E_2$), AFP-derived peptide (Pep) and tamoxifen (Tam) on the growth of the immature mouse uterus. The assay procedure is described in the Materials and Methods. Various doses indicated on the abscissa of each test agent were injected i.p. Twenty-two hours later uteri were harvested and weighed. Mean normalized uterine weights (mg uterine weight/g mouse body weight) for each group are shown on the ordinate.
Figure 13B:
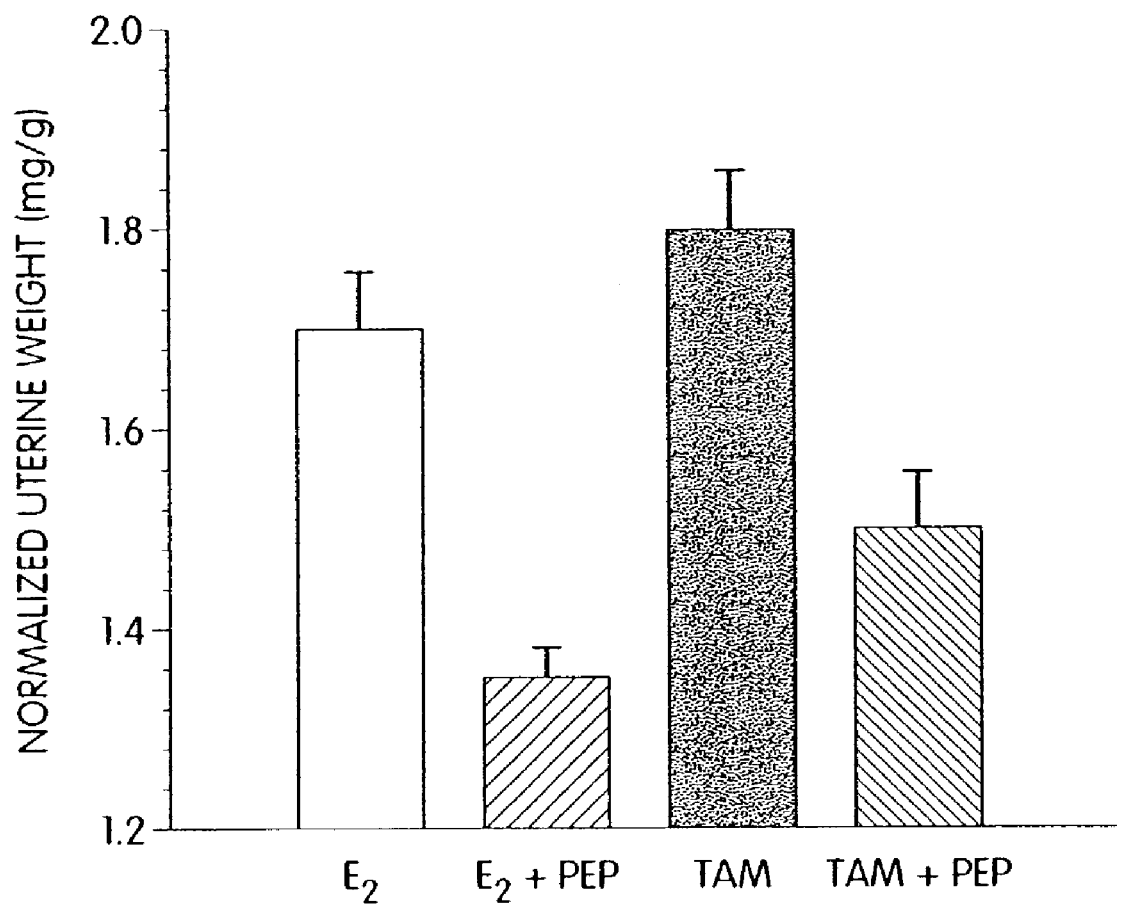
In FIG. 13b, Pep (1 µg) or vehicle (saline, 0.2 ml) were injected i.p. One hour later $E_2$ (0.5 µg) or Tam (1.0 µg) were injected i.p. Twenty-two hours later uteri were harvested and weighed. Normalized uterine weights in the $E_2$+Pep and Tam+Pep groups were significantly different, respectively, from normalized uterine weights in the $E_2$ group and Tam group, $p<0.05$, Wilcoxon Ranks Sum Test.

A troublesome side effect of tamoxifen in women has been its hypertrophic effect on the uterus (Assikis et al. 1995). It is likewise an estrogen agonist in the mumme uterus. As shown in FIG. 13a, tamoxifen stimulated the growth of immature mouse uterus by 50% at a dose of 1 µg/mouse. Tamoxifen's potency was approximately one-tenth that of $E_2$, but nevertheless, FIG. 13a reaffirms that tamoxifen acts as an estrogen agonist on the murine uterus, even though it antagonizes the effect of estrogen on cancer of the breast. Peptide, on the other hand, had no uterotrophic effect whatsoever (FIG. 13a), even at a dose of 10 µg/mouse, which is tenfold greater than the dose employed to prevent breast cancer growth (FIGS. 9a, 9b and 11). Moreover, peptide inhibited the uterotrophic effect of tamoxifen as well as that of estradiol (FIG. 13b).

The results of this study demonstrate that a synthetic 8-mer peptide derived from AFP prevented the $E_2$-stimulated growth of human breast cancer xenografts, including an ER+ breast cancer line that had become resistant to tamoxifen during chronic exposure to this drug in culture. This acquired resistance is similar to what happens in patients whose cancers become resistant to tamoxifen during chronic treatment with this drug (Norris et al. 1999). The peptide had no effect on the growth of ER-breast cancer, which is consistent with the activity found with its parent protein, AFP (Bennett et al. 1998)

TABLE I

Effect of urea on the biological activity of stored peptide.

| Test Agent | Storage Time | % Inhibition of E2-Stimulated Growth of Immature Mouse Uterus ± SE[b] |
|---|---|---|
| I Octapeptide SEQ ID NO: 2 QMTPVNPG | Fresh | 38 ± 3 |
| II Octapeptide SEQ ID NO: 2: QMTPVNPG | Stored over 1 year | 0 ± 2 |
| III II after Urea Treatment[a] | None | 34 ± 4 |
| IV Scrambled Octapeptide | Fresh | 2 ± 5 |
| V IV after Urea Treatment | None | 0 ± 4 |

[a]Peptide were dissolved in phosphate buffered saline ph 7.4 at a concentration of 200 ug/ml. They were then diluted so 20 μg/ml in 4 M urea and incubated at room temperature for one hour. After incubation they were diluted to 2 μg/ml in buffer and 0.5 ml of this preparation (1 μg) was injected into mice as described in legend to FIGS. 1a and 1b.
[b]Assessed as described in legend to FIGS. 1a and 1b.

EQUIVALENTS

Those skilled in the art will recognize, or be able to ascertain using no more than routine experimentation, numerous equivalents to the specific procedures described herein. Such equivalents are considered to be within the scope of the present invention and are covered by the following claims. The contents of all references, issued patents, and published patent applications cited throughout this application are hereby incorporated by reference. The appropriate components, processes, and methods of those patents, applications and other documents may be selected for the present invention and embodiments thereof.

What is claimed is:

1. A method of detecting a carcinoma in a patient, comprising the steps of:
   a) administering to the patient an effective amount of a labeled alpha-fetoprotein peptide consisting of an alpha-fetoprotein peptide sequence selected from the group consisting of: SEQ ID NOS: 1–9 and a metal ion;
   b) allowing for localization of said labeled peptide; and
   c) imaging said labeled peptide.

2. The method of claim 1, wherein said carcinoma is a primary and/or metastatic carcinoma.

3. The method of claim 1, wherein said labeled peptide further comprises a chelating agent, whereby said metal ion is bound to the peptide via the chelating agent.

4. The method of claim 3, wherein said chelating agent is a bifunctional agent.

5. The method of claim 1, wherein said administration is parenteral injection selected from the group consisting of intradermal, subcutaneous, intramuscular, intraperitoneal and intravenous injection.

6. The method of claim 1, wherein said labeled peptide consists of the sequence EKTOVNOGN (SEQ ID NO: 1) and further comprises a metal ion-binding domain, whereby said linked metal ion is bound to said peptide via said metal ion-binding domain.

7. The method of claim 6, wherein said metal ion-binding domain comprises at least one amino acid selected from the group consisting of cysteine, cystine, histidine, penicillamine, deacylated methionine, lysine, arginine, aspartic acid, glutamic acid and tyrosine.

8. The method of claim 1, wherein imaging is selected from the group consisting of gamma scintigraphy, specific photon emission computerized tomography, positron emission tomography and magnetic resonance imaging.

9. The method of claim 1, wherein said metal ion comprises at least one ionic element selected from the group consisting of iron, cobalt, nickel, copper, zinc, arsenic, selenium, gadolinium, molybdenum, technetium, ruthenium, palladium, silver, cadmium, indium, antimony, rhenium, osmium, iridium, platinum, gold, mercury, thallium, lead, bismuth, polonium and astatine.

10. The method of claim 1, wherein the metal ion comprises at least one property selected from the group consisting of radioactivity, paramagnetism and superparamagnetism.

11. A method of detecting a carcinoma in a patient, comprising the steps of:
   a) administering to the patient an effective amount of a labeled peptide which consists of a hydrophilic analog of an alpha-fetoprotein, having the structure $Xaa_1$-$Xaa_2$-$Xaa_3$-O-$Xaa_4$-N-$Xaa_5$-G-$Xaa_6$ (SEQ ID NO: 12) wherein
      i) $Xaa_1$ is selected from the group consisting of E, Q, and N;
      ii) $Xaa_2$ is selected from the group consisting of M and K;
      iii) $Xaa_3$ is selected from the group consisting of T and S;
      iv) $Xaa_4$ is selected from the group consisting of V, I, L, T;
      v) $Xaa_5$ is selected from the group consisting of P, O and S; and
      vi) $Xaa_6$ is an amino acid structure which may be present or absent and when present selected from the group consisting of E, Q, and N;
      and a metal ion;
   b) allowing for localization of said labeled peptide; and
   c) imaging said labeled peptide.

12. The method of claim 11, wherein said carcinoma is a primary and/or metastatic carcinoma.

13. The method of claim 11, wherein said labeled peptide further comprises a chelating agent, whereby said metal ion is bound to the peptide via the chelating agent.

14. The method of claim 13, wherein said chelating agent is a bifunctional agent.

15. The method of claim 11, wherein said administration is parenteral injection selected from the group consisting of intradermal, subcutaneous, intramuscular, intraperitoneal and intravenous injection.

16. A method of diagnosing a cell-proliferating disorder in a patient, comprising:
   a) providing a metal ion-labeled alpha-fetoprotein peptide consisting of an alpha-fetoprotein peptide sequence selected from the group consisting of: SEQ ID NOS: 1–9 and a metal ion;
   b) administering to the patient an effective amount of said metal ion-labeled alpha-fetoprotein peptide;
   c) allowing for localization of said metal ion-labeled alpha-fetoprotein peptide; and
   d) imaging said metal ion-labeled alpha-fetoprotein peptide.

17. The method of claim 16, wherein said cell-proliferating disorder is breast cancer.

18. The method of claim 16, wherein said labeled peptide further comprises a chelating agent, whereby said metal ion is bound to the peptide via the chelating agent.

19. The method of claim 16, wherein said chelating agent is a bifunctional agent.

20. The method of claim 16, wherein said administration is parenteral injection selected from the group consisting of intradermal, subcutaneous, intramuscular, intraperitoneal and intravenous injection.

21. The method of claim 16, wherein said labeled peptide consists of the sequence EKTOVNOGN (SEQ ID NO:1) and further comprises a metal ion-binding domain, whereby said linked metal ion is bound to said peptide via said metal ion-binding domain.

22. The method of claim 21, wherein said metal ion-binding domain comprises at least one amino acid selected from the group consisting of cysteine, cystine, histidine, penicillamine, deacylated methionine, lysine, arginine, aspartic acid, glutamic acid and tyrosine.

23. The method of claim 16, wherein imaging is selected from the group consisting of gamma scintigraphy, specific photon emission computerized tomography, positron emission tomography and magnetic resonance imaging.

24. The method of claim 16, wherein said metal ion comprises at least one ionic element selected from the group consisting of iron, cobalt, nickel, copper, zinc, arsenic, selenium, gadolinium, molybdenum, technetium, ruthenium, palladium, silver, cadmium, indium, antimony, rhenium, osmium, iridium, platinum, gold, mercury, thallium, lead, bismuth, polonium and astatine.

25. The method of claim 16, wherein the metal ion comprises at least one property selected from the group consisting of radioactivity, paramagnetism and superparamagnetism.

* * * * *

UNITED STATES PATENT AND TRADEMARK OFFICE
CERTIFICATE OF CORRECTION

PATENT NO. : 7,220,402 B1  Page 1 of 1
APPLICATION NO. : 10/300531
DATED : May 22, 2007
INVENTOR(S) : Thomas T. Andersen et al.

It is certified that error appears in the above-identified patent and that said Letters Patent is hereby corrected as shown below:

Title Page 1, (73), the Assignee should be: "Albany Medical College" (US)

Albany, NY (US)

Signed and Sealed this

Ninth Day of November, 2010

David J. Kappos
*Director of the United States Patent and Trademark Office*

SEQUENCE LISTING

```
<160> NUMBER OF SEQ ID NOS: 12

<210> SEQ ID NO 1
<211> LENGTH: 9
<212> TYPE: PRT
<213> ORGANISM: Homo sapiens
<220> FEATURE:
<221> NAME/KEY: MOD_RES
<222> LOCATION: (4)
<223> OTHER INFORMATION: 4Hyp
<220> FEATURE:
<221> NAME/KEY: MOD_RES
<222> LOCATION: (7)
<223> OTHER INFORMATION: 4Hyp

<400> SEQUENCE: 1

Glu Lys Thr Pro Val Asn Pro Gly Asn
  1               5

<210> SEQ ID NO 2
<211> LENGTH: 8
<212> TYPE: PRT
<213> ORGANISM: Homo sapiens

<400> SEQUENCE: 2

Gln Met Thr Pro Val Asn Pro Gly
  1               5

<210> SEQ ID NO 3
<211> LENGTH: 9
<212> TYPE: PRT
```

-continued

```
<213> ORGANISM: Homo sapiens

<400> SEQUENCE: 3

Gln Met Thr Pro Val Asn Pro Gly Glu
 1               5

<210> SEQ ID NO 4
<211> LENGTH: 8
<212> TYPE: PRT
<213> ORGANISM: Homo sapiens
<220> FEATURE:
<221> NAME/KEY: MOD_RES
<222> LOCATION: (4)
<223> OTHER INFORMATION: 4Hyp
<220> FEATURE:
<221> NAME/KEY: MOD_RES
<222> LOCATION: (7)
<223> OTHER INFORMATION: 4Hyp

<400> SEQUENCE: 4

Glu Met Thr Pro Val Asn Pro Gly
 1               5

<210> SEQ ID NO 5
<211> LENGTH: 9
<212> TYPE: PRT
<213> ORGANISM: Homo sapiens
<220> FEATURE:
<221> NAME/KEY: MOD_RES
<222> LOCATION: (4)
<223> OTHER INFORMATION: 4Hyp
<220> FEATURE:
<221> NAME/KEY: MOD_RES
<222> LOCATION: (7)
<223> OTHER INFORMATION: 4Hyp

<400> SEQUENCE: 5

Glu Met Thr Pro Val Asn Pro Gly Gln
 1               5

<210> SEQ ID NO 6
<211> LENGTH: 8
<212> TYPE: PRT
<213> ORGANISM: Homo sapiens

<400> SEQUENCE: 6

Glu Met Thr Pro Val Asn Pro Gly
 1               5

<210> SEQ ID NO 7
<211> LENGTH: 9
<212> TYPE: PRT
<213> ORGANISM: Homo sapiens

<400> SEQUENCE: 7

Glu Met Thr Pro Val Asn Pro Gly Gln
 1               5

<210> SEQ ID NO 8
<211> LENGTH: 9
<212> TYPE: PRT
<213> ORGANISM: Homo sapiens
<220> FEATURE:
<221> NAME/KEY: MOD_RES
<222> LOCATION: (4)
<223> OTHER INFORMATION: 4Hyp

<400> SEQUENCE: 8
```

```
Glu Met Thr Pro Val Asn Pro Gly Gln
 1               5

<210> SEQ ID NO 9
<211> LENGTH: 9
<212> TYPE: PRT
<213> ORGANISM: Homo sapiens
<220> FEATURE:
<221> NAME/KEY: MOD_RES
<222> LOCATION: (7)
<223> OTHER INFORMATION: 4Hyp

<400> SEQUENCE: 9

Glu Met Thr Pro Val Asn Pro Gly Gln
 1               5

<210> SEQ ID NO 10
<211> LENGTH: 8
<212> TYPE: PRT
<213> ORGANISM: human
<220> FEATURE:
<221> NAME/KEY: MOD_RES
<222> LOCATION: (7)
<223> OTHER INFORMATION: 4Hyp

<400> SEQUENCE: 10

Glu Met Thr Pro Val Asn Pro Gly
 1               5

<210> SEQ ID NO 11
<211> LENGTH: 8
<212> TYPE: PRT
<213> ORGANISM: Homo sapiens
<220> FEATURE:
<221> NAME/KEY: MOD_RES
<222> LOCATION: (4)
<223> OTHER INFORMATION: 4Hyp

<400> SEQUENCE: 11

Glu Met Thr Pro Val Asn Pro Gly
 1               5

<210> SEQ ID NO 12
<211> LENGTH: 9
<212> TYPE: PRT
<213> ORGANISM: Homo sapiens
<220> FEATURE:
<221> NAME/KEY: VARIANT
<222> LOCATION: (1)
<223> OTHER INFORMATION: Wherein "Xaa" is E or Q or N or an acetylated
      or acylated derivative thereof .
<220> FEATURE:
<221> NAME/KEY: VARIANT
<222> LOCATION: (2)
<223> OTHER INFORMATION: Wherein "Xaa" is M or K or an analogue thereof.
<220> FEATURE:
<221> NAME/KEY: VARIANT
<222> LOCATION: (3)
<223> OTHER INFORMATION: Wherein "Xaa" is T or S or an amino acid
      providing steric hinderance and hydrophilicity.
<220> FEATURE:
<221> NAME/KEY: MOD_RES
<222> LOCATION: (4)
<223> OTHER INFORMATION: 4Hyp
<220> FEATURE:
<221> NAME/KEY: VARIANT
<222> LOCATION: (5)
<223> OTHER INFORMATION: Wherein "Xaa" is V or I or L or T or a
      beta-branched amino acid or a hydrophobic amino
      acid structure.
<220> FEATURE:
<221> NAME/KEY: VARIANT
```

```
<222> LOCATION: (7)
<223> OTHER INFORMATION: Wherein "Xaa" is P or S.
<220> FEATURE:
<221> NAME/KEY: MOD_RES
<222> LOCATION: (7)
<223> OTHER INFORMATION: 4Hyp
<220> FEATURE:
<221> NAME/KEY: VARIANT
<222> LOCATION: (9)
<223> OTHER INFORMATION: Wherein "Xaa" is an amino acid structure that
      may be present or absent; when present it may be Q or N.

<400> SEQUENCE: 12

Xaa Xaa Xaa Pro Xaa Asn Xaa Gly Xaa
 1                   5
```